(12) United States Patent
Boggs, II et al.

(10) Patent No.: US 8,805,533 B2
(45) Date of Patent: Aug. 12, 2014

(54) SYSTEMS AND METHODS OF NEUROMODULATION STIMULATION FOR THE RESTORATION OF SEXUAL FUNCTION

(75) Inventors: Joseph W. Boggs, II, Carrboro, NC (US); Geoffrey B. Thrope, Shaker Heights, OH (US); Robert B. Strother, Willoughby Hills, OH (US); Joseph J. Mrva, Euclid, OH (US)

(73) Assignee: Medtronic, Inc., Minneapolis, MN (US)

( * ) Notice: Subject to any disclaimer, the term of this patent is extended or adjusted under 35 U.S.C. 154(b) by 118 days.

(21) Appl. No.: 13/031,482

(22) Filed: Feb. 21, 2011

(65) Prior Publication Data

US 2011/0144468 A1    Jun. 16, 2011

Related U.S. Application Data

(60) Division of application No. 11/891,074, filed on Aug. 9, 2007, now Pat. No. 7,894,913, which is a continuation-in-part of application No. 11/149,654, filed on Jun. 10, 2005, now Pat. No. 7,565,198, said application No. 11/891,074 is a continuation-in-part of application No. 11/150,418, filed on Jun. 10, 2005, now Pat. No. 7,239,918, said application No. 11/891,074 is a continuation-in-part of application No. 11/290,268, filed on Nov. 30, 2005, now abandoned, and a continuation-in-part of application No. 11/729,333, filed on Mar. 28, 2007.

(60) Provisional application No. 60/578,742, filed on Jun. 10, 2004, provisional application No. 60/599,193, filed on Aug. 5, 2004, provisional application No. 60/680,598, filed on May 13, 2005.

(51) Int. Cl.
*A61N 1/36* (2006.01)

(52) U.S. Cl.
USPC .......................................... 607/116; 607/40

(58) Field of Classification Search
USPC ................................ 607/116–119, 137
See application file for complete search history.

(56) References Cited

U.S. PATENT DOCUMENTS

| | | | |
|---|---|---|---|
| 5,454,840 A | 10/1995 | Krakovsky et al. | |
| 6,425,877 B1 * | 7/2002 | Edwards | 604/21 |
| 6,517,534 B1 * | 2/2003 | McGovern et al. | 606/41 |
| 6,735,474 B1 | 5/2004 | Loeb et al. | |
| 7,822,482 B2 * | 10/2010 | Gerber | 607/116 |

OTHER PUBLICATIONS

Extended Search Report from European application No. 05826316.1, dated Dec. 13, 2012, 11 pp.

* cited by examiner

*Primary Examiner* — Luther Behringer
(74) *Attorney, Agent, or Firm* — Shumaker & Sieffert, P.A.

(57) ABSTRACT

Systems and methods use an external and/or implantable pulse generator system for neuromodulation stimulation to treat sexual dysfunction by the unilateral or bilateral stimulation of a target nerve A and/or a target nerve B using one or more leads and electrodes implanted in tissue in the pelvic region. The electrical stimulation waveform may be conveyed to the target nerve A electrode for a first predetermined amount of time, and conveyed to the target nerve B electrode for a second predetermined amount of time.

26 Claims, 27 Drawing Sheets

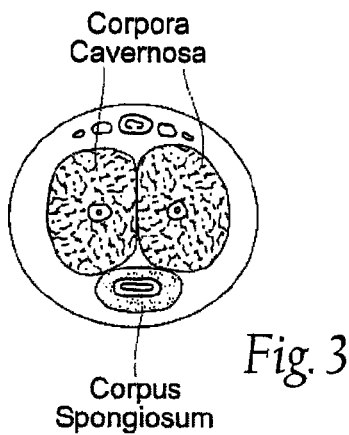
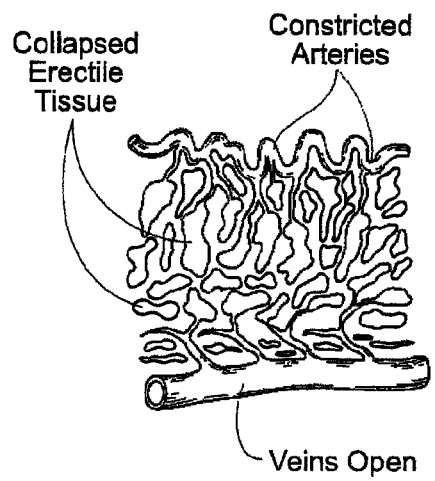
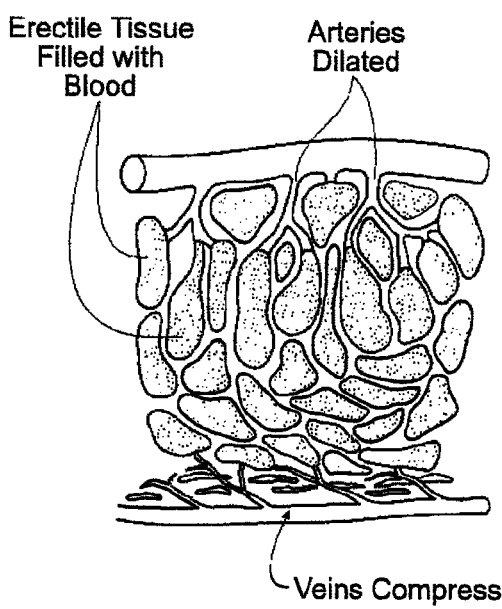
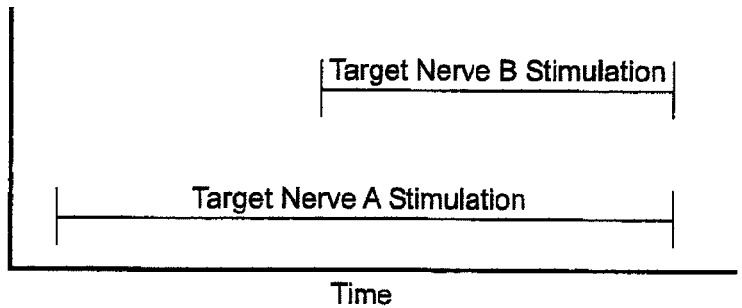
Fig. 3
Fig. 4
Fig. 5
Fig. 6

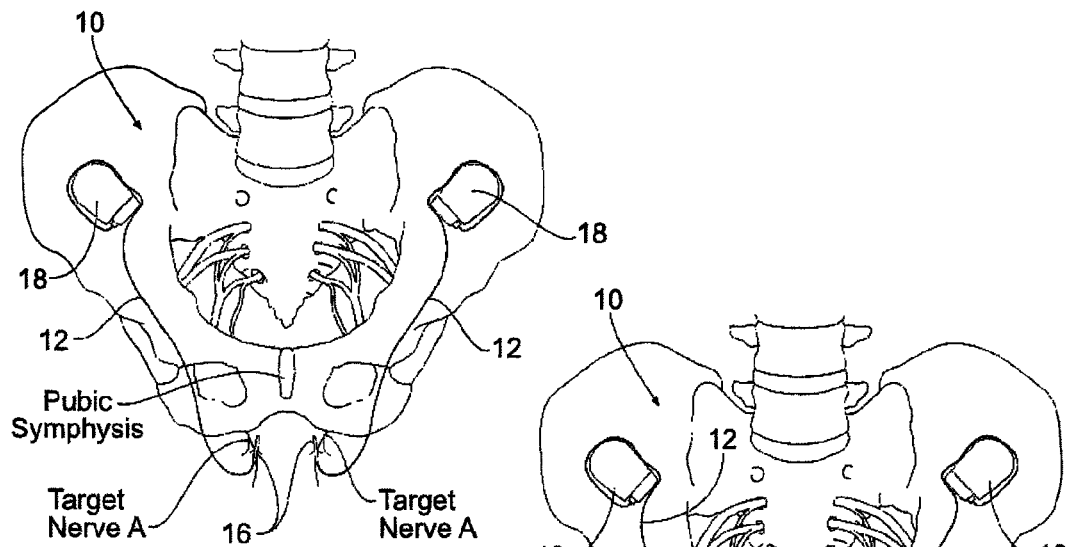
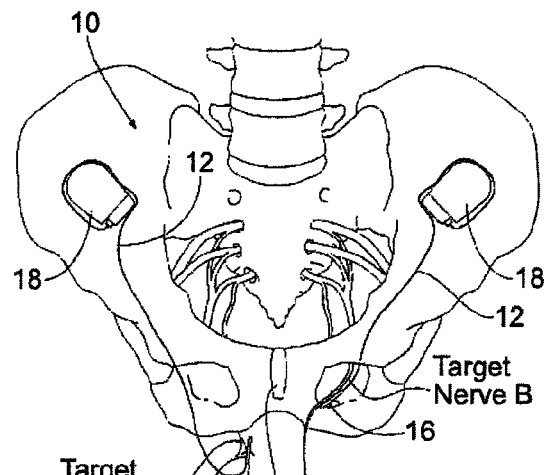
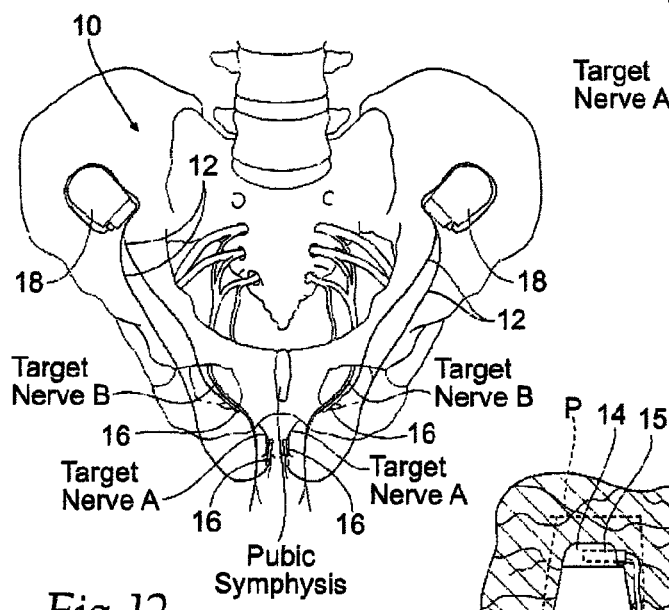
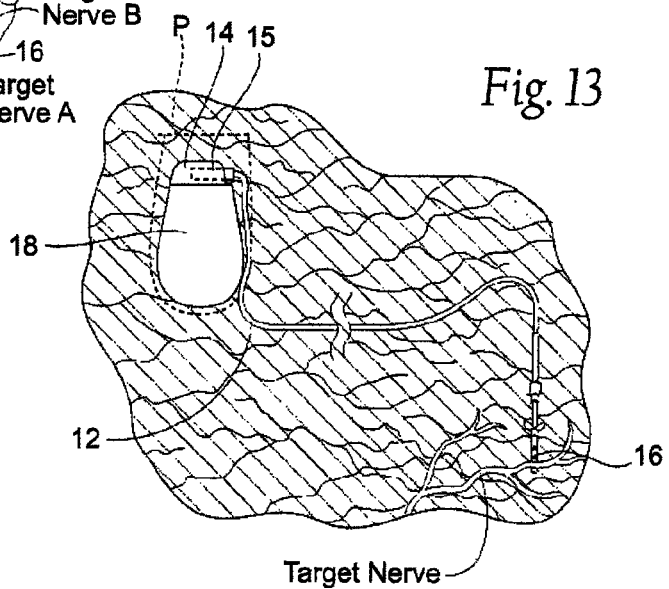

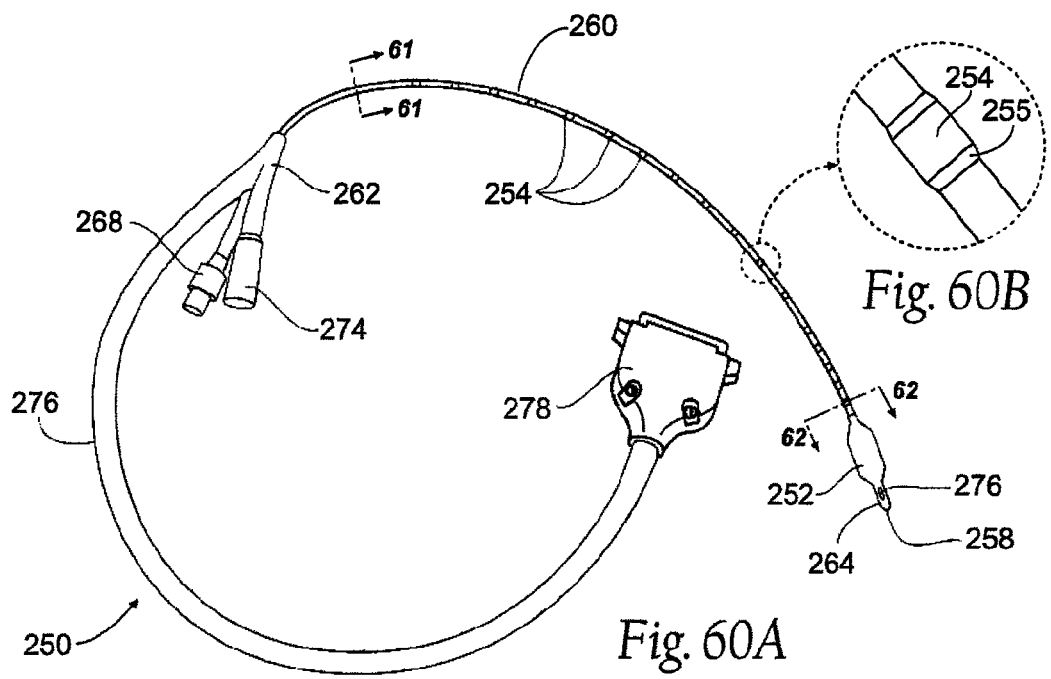
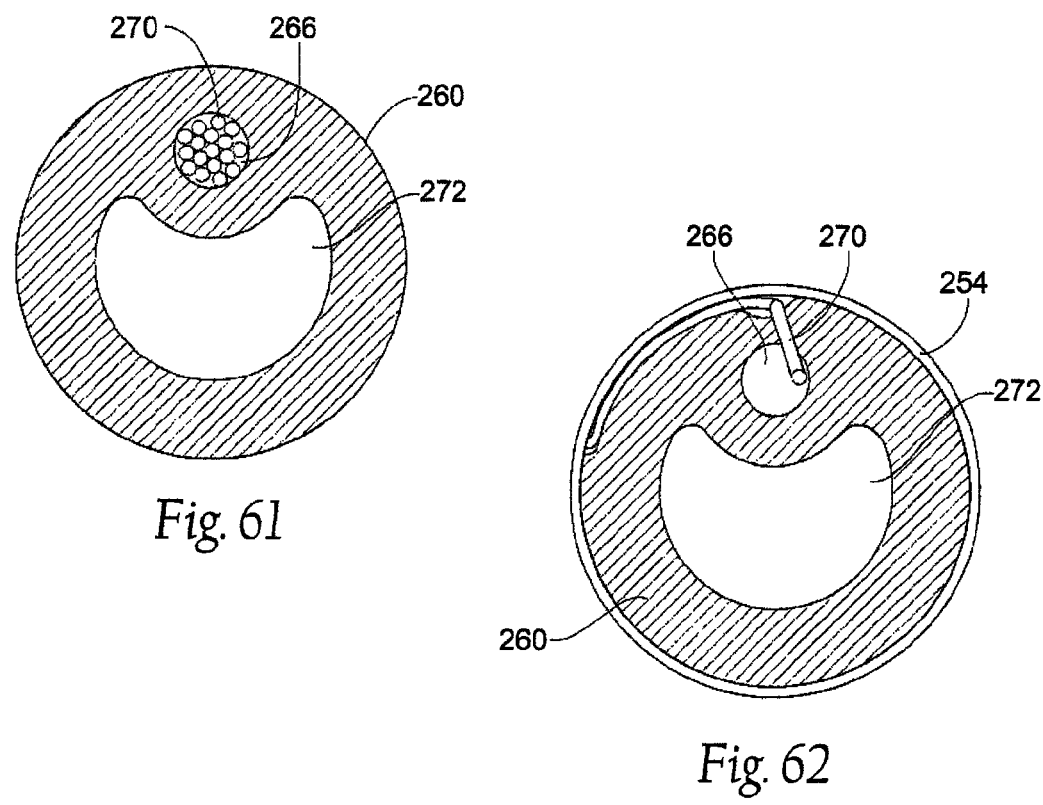

SYSTEMS AND METHODS OF NEUROMODULATION STIMULATION FOR THE RESTORATION OF SEXUAL FUNCTION

RELATED APPLICATIONS

This application is a divisional of U.S. patent application Ser. No. 11/891,074, filed Aug. 9, 2007, now U.S. Pat. No. 7,894,913, entitled "Systems and Methods of Neuromodulation Stimulation for the Restoration of Sexual Function", which is a continuation-in-part of U.S. patent application Ser. No. 11/149,654, filed Jun. 10, 2005, now U.S. Pat. No. 7,565,198, entitled "Systems and Methods for Bilateral Stimulation of Left and Right Branches of the Dorsal Genital Nerves to Treat Dysfunctions Such as Urinary Incontinence," which claims the benefit of U.S. Provisional Patent Application Ser. No. 60/578,742, filed Jun. 10, 2004, entitled "Systems and Methods for Bilateral Stimulation of Left and Right Branches of the Dorsal Genital Nerves to Treat Dysfunctions, Such as Urinary Incontinence," which are all incorporated herein by reference.

U.S. patent application Ser. No. 11/891,074, now U.S. Pat. No. 7,894,913, is also a continuation-in-part of U.S. patent application Ser. No. 11/150,418, filed Jun. 10, 2005, now U.S. Pat. No. 7,239,918, entitled "Implantable Pulse Generator for Providing Functional and/or Therapeutic Stimulation of Muscles and/or Nerves and/or Central Nervous System Tissue," which claims the benefit of U.S. Provisional Patent Application Ser. No. 60/578,742, filed Jun. 10, 2004, entitled "Systems and Methods for Bilateral Stimulation of Left and Right Branches of the Dorsal Genital Nerves to Treat Dysfunctions, Such as Urinary Incontinence," U.S. Provisional Patent Application Ser. No. 60/599,193, filed Aug. 5, 2004, entitled "Implantable Pulse Generator for Providing Functional and/or Therapeutic Stimulation of Muscles and/or Nerves," and U.S. Provisional Patent Application Ser. No. 60/680,598, filed May 13, 2005, entitled "Implantable Pulse Generator for Providing Functional and/or Therapeutic Stimulation of Muscles and/or Nerves and/or Central Nervous System Tissue," which are all incorporated herein by reference.

U.S. patent application Ser. No. 11/891,074, now U.S. Pat. No. 7,894,913, is also a continuation-in-part of U.S. patent application Ser. No. 11/290,268, filed Nov. 30, 2005 now abandoned, entitled "Neuromodulation Stimulation for the Restoration of Sexual Function," and a continuation-in-part of co-pending U.S. patent application Ser. No. 11/729,333, filed Mar. 28, 2007, entitled "Systems and Methods for Bilateral Stimulation of Left and Right Branches of the Dorsal Genital Nerves to Treat Urologic Dysfunctions," both of which are incorporated herein by reference.

STATEMENT REGARDING FEDERALLY SPONSORED RESEARCH

This invention was made with government support under grant number 1R43NS56623-01 awarded by the National Institutes of Health, through the National Institute of Neurological Disorders and Stroke. The Government may have certain rights in the invention.

FIELD OF THE INVENTION

This invention relates to systems and methods for neuromodulation stimulation for the restoration of sexual function in animals, including humans. The invention includes unique tools and methods to restore erectile function via electrical stimulation of peripheral nerves and/or spinal nerve roots.

BACKGROUND OF THE INVENTION

I. Neuromodulation Stimulation

Neuromodulation stimulation (the electrical excitation of nerves to indirectly affect the stability or performance of a physiological system) can provide functional and/or therapeutic outcomes. While existing systems and methods can provide remarkable benefits to individuals requiring neuromodulation stimulation, many limitations and issues still remain. For example, existing systems can often require the user to wear an external stimulator, which may provide a positive functional outcome, but may also negatively affect quality of life issues.

A variety of products and treatment methods are available for neuromodulation stimulation. As an example, neuromodulation stimulation has been used for the treatment of sexual dysfunction, which affects both men and women. A wide range of options exist for the restoration of sexual function. Treatments include everything from medications, simple mechanical devices, psychological counseling, external stimulators, and surgically implanted devices.

Both external and implantable devices have been described in the art for the purpose of neuromodulation stimulation for the restoration of sexual function. The operation of these devices typically includes the use of an electrode placed either on the external surface of the skin or a surgically implanted electrode. Although these modalities have shown the ability to provide a neuromodulation stimulation with some positive effects, they have received limited acceptance by patients because of their limitations of portability, limitations of treatment regimes, and limitations of ease of use and user control.

II. Sexual Dysfunction

One form of male sexual dysfunction is know as Erectile Dysfunction (ED), and is often referred to as "impotency." There are some common diseases such as diabetes, Peyronie's disease, heart disease, and prostate cancer that are associated with impotency or have treatments that may cause impotency. And in some cases the cause may be psychological.

Erectile Dysfunction is common problem affecting men and is defined as the inability to achieve or maintain a penile erection sufficient for sexual activity. It is estimated that 35% to 50% of all men aged 40 to 70 have some form of ED, nearly 46 million Americans have ED, and over 150 million men have ED worldwide. It is also estimated that sexual dysfunctions occur in 43 percent of women in the United States. It would cost $3.5 billion per year if only one fifth of Americans with ED were treated with the first line of treatment (oral therapy such as PDE-5 inhibitors), and the cost for the second line of treatment (such as injection or transurethral administration of alprostadil) is approximately twice as expensive. A cost-effective therapy is needed because the number of men seeking treatment tripled between 1997 and 2000 and is expected to increase as awareness of treatment options for ED becomes more widespread.

The severity of erectile dysfunction can range from 1) mild ED, in which a man is occasionally unable to achieve and sustain an erection sufficient for intercourse, to 2) frequent or moderate ED to 3) severe or complete ED, in which a man is never able to produce and sustain an erection sufficient for intercourse. The prevalence of moderate to complete ED increases with age. Approximately 20% of men aged 40 years have moderate to severe ED and approximately 70% of men aged 70 years have moderate to severe ED. Over 70% of men with ED report that their quality of life is moderately to severely reduced by ED, and over 70% of men with ED feel hurt by the response of their partner to their ED and feel "to some extent a failure" because of their ED. Thus, ED is often associated with poor self-image, depression, and it can affect interpersonal relationships and lead to increased mental stress.

ED is often a result of a combination of psychological and organic factors, but it is thought to be purely psychological in origin in less than 30% of the cases. Organic factors can include complications from neurologic diseases (stroke, multiple sclerosis, Alzheimer's disease, brain or spinal tumors), chronic renal failure, prostate cancer, diabetes, trauma, surgery, medications, and abnormal structure. However, most cases of ED are associated with vascular diseases. An erection cannot be sustained without sufficient blood flow into and entrapment within the erectile bodies of the penis, and vascular related ED can be due to a malfunction of either the arterial or the venous system.

In a healthy individual, increased blood low into the penis by means of arterial dilation and decreased blood flow from the penis via venous occlusion generates penile erection. Activation of a parasympathetic nerve such as the cavernous nerve, which causes relaxation of corporeal smooth muscle of the cavernosal and trabecular spaces, generates the arterial dilation. A normal reflex penile erection begins with the filling and expansion of the three erectile bodies: the corpus spongiosum and the two corpora cavernosa. This expansion compresses the venules against the tunica albuginea, preventing blood from leaving the penis and furthering the erection by way of intrinsic venous occlusion (within the penis). Extrinsic venous occlusion (outside the penis) is provided by activation of a somatic nerve such as the pudendal nerve, which causes contraction of the bulbospongiosus and ischiocavernosus muscles, trapping the blood in the penis erectile tissues and increasing tumescence (Schmidt and Schmidt, Sleep 1993; 16:171-183).

Persons with vasculogenic erectile dysfunction are unable to achieve penile erection due to either insufficient arterial blood flow or insufficient venous occlusion or both. Normal reflex erection coordinates dilation of penile blood vessels, augmenting vascular filling, and venous occlusion, preventing leakage and increasing penile stiffness.

In animal studies, it has been found that stimulation of the cavernous nerve (referenced as target nerve A) resulted in an increase of intracavernous pressure, and additional stimulation of the pudendal nerve (referenced as target nerve B) increased the intracavernous pressure to well above the systolic pressure, producing a reflex erection (see FIG. 1).

FIGS. 2 and 3 show a profile and cross-section of the penis, illustrating the anatomical relationship of the erectile tissue (corpora cavernosa and corpus spongiosum) inside the penis. FIGS. 4 and 5 show the physiological changes in the size of the penile arteries, erectile tissue, and veins during erection. FIG. 4 shows the penile arteries constricted, the erectile tissue collapsed, and the veins open prior to an erection. Arterial dilation leads to increased inflow of blood, which fills and expands the erectile tissue as the veins are compressed to decrease outflow of blood from the erectile tissue, as shown in FIG. 5.

III. Methods of Treatment For ED

Methods of treatment for erectile dysfunction are available but are either often discontinued due to loss of efficacy or side effects or reserved as a final recourse requiring irrevocable damage. Currently three lines of treatment exist for ED. Oral therapy (PDE-5 inhibitors) is usually the first line of treatment, and it can be effective in up to 70% of men when it is first administered, but half of the patients stop taking PDE-5 inhibitors because they lose their effectiveness within one to three years.

The second line of treatment is usually a minimally invasive therapy such as a vacuum device or direct administration of a vasoactive agent. The second-line treatments are usually effective in 33% to 70% of men, but they are also later discontinued by over half of the patients, often due to side effects such as pain or local damage at the site of administration. For the 30% to 65% of men who fail or discontinue oral therapy, the total cost for the second line of treatment (vacuum device or alprostadil, administered via injection or transurethrally) would be $1 to $6 billion. However, side effects of pain and local damage are associated with the second line of treatment, and at least half of the men discontinue this form of therapy.

If the men who failed or discontinued both the first and second lines of treatment chose to receive a penile prosthesis (the third line of treatment), the total cost would be over $20 billion. Yet, implantation of a penile prosthesis is reserved for the final method of treatment because the implantation causes permanent (irrevocable) damage to the erectile tissue resulting in the loss of any future erection if the implant is removed. Thus, an alternative approach is needed that can provide a multitude of advantages over the current therapies.

IV. Neuromodulation Stimulation

Neuromodulation stimulation provides a multitude of advantages over the three previously described forms of erectile dysfunction treatment. Systemic side effects (headache, flushing, dyspepsia, etc.) and permanent damage to the corpora cavernosa may be avoided by electrically stimulating one or more peripheral nerves to coordinate arterial dilation with venous occlusion, producing an erection.

An implantable stimulation system is needed that can provide an erection quickly and is acceptable to men who use or may need to use nitrates to treat cardiovascular disease because over 35% of men with cardiovascular disease develop ED. The loss of efficacy of oral therapy is likely due to the long duration (four to eighteen hours) of action, and the consistently elevated drug concentrations can reduce the response to the drug via tachyphylaxis or increased tolerance as seen with nitroglycerin tolerance. No loss of efficacy is expected with an implantable stimulation system that is adapted to be activated only minutes before (e.g., two to ten) and during erection, and it will provide controlled release of neurotransmitter via, activation of targeted peripheral nerves.

The implantable stimulation system may be activated by the movement of a magnet over a magnetic reed switch within an implantable pulse generator of the stimulation system, or the press of a remote button, for example. Unlike the second line of treatment, this approach will not require a constrictive ring, needle insertion, or urethral-suppository insertion, which can cause local injury prior to each erection and lead to discontinuation of treatment. In contrast to the penile implant, an implantable stimulation system approach will not damage the erectile tissue.

There remains a need for systems and methods that can effectively restore sexual function, in a straightforward manner, without requiring drug therapy and complicated (and in some instanced irrevocable) surgical procedures.

SUMMARY OF THE INVENTION

The stimulation system will use electrical stimulation (i.e., activation) of a target nerve A and/or a target nerve B of either the male or the female to provide a sexual restoration function on-demand with a simple surgical procedure that preserves the existing anatomy, wherein the sexual restoration may include erection, ejaculation, orgasm, vaginal lubrication, arousal (pleasure), and engorgement, as non-limiting examples.

One aspect of the invention provides systems and methods for the treatment of sexual dysfunction by the stimulation of a target nerve A and/or a target nerve B using one or more stimulation electrodes sized and configured to be implanted in tissue in a region at or near the target nerve(s), and one or more external or implantable pulse generators to convey electrical stimulation waveforms to the stimulation electrode(s) to stimulate the target nerve A and/or the target nerve B.

Another aspect of the invention provides systems and methods for a focused stimulation electrode assembly. The assembly comprises an elongated lead sized and configured to be implanted in tissue, an electrode array coupled to the lead, the electrode array including at least one conductive element and configured to be implanted in tissue and to apply electrical stimulation to a targeted tissue region, the electrode array including a distal end and a proximal end, and at least one fin extending axially along the electrode array and in a non-contact relationship with the at least one conductive element, the fin comprising a non-conductive material to focus the electrical stimulation toward the targeted tissue region and away from a non-targeted tissue region. The targeted tissue region comprises at least one of a target nerve A and a target nerve B.

The one or more fins may extend from the electrode array distal end to the electrode array proximal end, or the fin(s) may extend from beyond the electrode array distal end to beyond the electrode array proximal end, or any combination. The fin may be flexible or the fin may be rigid, depending on the application. The fin may be deployable between a collapsed condition along the electrode array and an expanded condition extending outward of the electrode array.

The target nerve A can include the cavernous nerve and/or spinal, sacral, lumbar, and/or thoracic roots and/or branches; the prostatic plexus and/or its spinal, sacral, lumbar, and/or thoracic roots and/or branches; the pelvic nerve and/or its spinal, sacral, lumbar, and/or thoracic roots and/or branches; the hypogastric nerve and/or its spinal, sacral, lumbar, and/or thoracic roots and/or branches; and the splanchnic nerve and/or its spinal, sacral, lumbar, and/or thoracic roots and/or branches.

The target nerve B can include the pudendal nerve and/or its spinal, sacral, lumbar, and/or thoracic roots and/or branches; the perineal nerve and/or its spinal, sacral, lumbar, and/or thoracic roots and/or branches; the nerves that innervate the ischiocavernosus, bulbocavernosus, and/or bulbospongiosus muscles and/or their spinal, sacral, lumbar, and/or thoracic roots and/or branches; and the nerves that innervate the transverse perineal muscles and/or their spinal, sacral, lumbar, and/or thoracic roots and/or branches.

In one aspect of the invention, the electrode array may be introduced to at least one of the target nerve A and the target nerve B via the perineum in males and/or females, for the restoration of sexual function.

In another aspect of the invention, the electrode array may be introduced to at least one of the target nerve A and the target nerve B via the anterior and/or posterior side of the pelvis in males and/or females for the restoration of sexual function.

In yet another aspect of the invention, the electrical stimulation conveyed to the electrode array affect efferent stimulation of at least one of the target nerve A and the target nerve B, to produce an erection.

In yet another aspect of the invention, the electrical stimulation conveyed to the electrode array affect afferent stimulation of at least one of the target nerve A and the target nerve B, the efferent stimulation activating central nervous system circuitry that coordinates and/or produces efferent activity in the at least one of the target nerve A and the target nerve B, to produce an erection.

One aspect of the invention provides a method of using a focused stimulation electrode assembly including the steps of providing a focused stimulation electrode assembly, the assembly including an elongated lead sized and configured to be implanted in tissue, an electrode array coupled to the lead, the electrode array including at least one conductive element and configured to be implanted in tissue and to apply electrical stimulation to a targeted tissue region, the electrode array including a distal end and a proximal end, and at least one fin extending axially along the electrode array and in a non-contact relationship with the at least one conductive element, the fin comprising a non-conductive material to focus the electrical stimulation toward the targeted tissue region and away from a non-targeted tissue region.

The method further includes implanting the focused stimulation electrode assembly at a targeted tissue region, and operating the focused stimulation electrode assembly to focus the electrical stimulation toward the targeted tissue region and away from a non-targeted tissue region.

The method may also include tuning the electrode array to focus the electrical stimulation toward the targeted tissue region and away from the non-targeted tissue region.

Yet another aspect of the invention provides systems and methods for a stimulating catheter adapted for use in diagnosing and/or treating a urologic function, the catheter including an elongated flexible body having a proximal end and a distal end and at least one lumen extending at least a portion of the body, an inflatable balloon disposed at or near the distal end, an electrode array disposed along the body and proximal to the inflatable balloon, and an electrical lead coupled to each electrode in the electrode array and extending through the body, the electrical lead adapted for external connection to an electrical source.

In one aspect of the invention, the flexible body is adapted to be positioned within the urethra or rectum of a male and/or female animal or human. The flexible body may be malleable, or it may be pre-bent in a desired configuration so as to maintain its shape throughout the insertion and stimulation process. The flexible body may also include a multi-lumen body, including a first lumen and a second lumen, the first lumen and the second lumen extending at least a portion of the catheter body. The first lumen may carry the electrical lead to each electrode in the electrode array, and may also be in fluid flow communication with the balloon and serves as a path for fluid flow to fill and drain the balloon.

In another aspect of the invention, the electrode array comprises a proximal portion and a distal portion, the electrodes of the proximal portion are spaced apart a first distance, and the electrodes of the distal portion are spaced apart less than the first distance. The electrical stimulation conveyed to the electrode array affect efferent stimulation of at least one of a target nerve A and a target nerve B, to produce an erection.

Another aspect of the invention provides a method of using a stimulating catheter including the steps of providing a stimulating catheter, inserting the stimulating catheter within one of the urethra and rectum of an animal, inflating the balloon to secure the stimulating catheter in position, and operating the stimulating catheter to convey electrical stimulation waveforms to the electrode array to stimulate at least one of a target nerve and a target muscle. In one embodiment the target nerve comprises at least one of a target nerve A and a target nerve B.

In one embodiment, the stimulating catheter comprises an elongated flexible body having a proximal end and a distal end and at least one lumen extending at least a portion of the body, an inflatable balloon disposed at or near the distal end, an electrode array disposed along the body and proximal to the inflatable balloon, and an electrical lead coupled to each electrode in the electrode array and extending through the body, the electrical lead adapted for external connection to an electrical source.

Yet another aspect of the invention provides a stimulation system for the treatment of sexual dysfunction comprising at least one elongated target nerve A lead sized and configured to be coupled to a pulse generator and implanted in tissue, the target nerve A lead including at least one target nerve A stimulation electrode array coupled to the lead, the electrode array including at least one conductive element and configured to be implanted in tissue and to apply electrical stimulation to a target nerve A, the electrode array including a distal end and a proximal end, at least one fin extending axially along the electrode array and in a non-contact relationship with the at least one conductive element, the fin comprising a non-conductive material to focus the electrical stimulation toward the a target nerve A and away from a non-targeted tissue region, and at least one pulse generator to convey electrical stimulation waveforms to the target nerve A stimulation electrode array to stimulate the target nerve A to treat sexual dysfunction.

In one embodiment, the pulse generator sized and configured to be positioned in subcutaneous tissue in an anterior pelvic region remote from the at least one target nerve A electrode array, the pulse generator comprising a case having a size between about 5 mm and about 10 mm thick, between about 15 mm and about 40 mm wide, and between about 40 mm and about 60 mm long, and the pulse generator comprising non-inductive wireless telemetry circuitry using VHF/UHF signals, the non-inductive wireless telemetry circuitry being functional at a distance as far as arm's reach away from the patient, and being adapted for programming and interrogation of the implantable pulse generator.

Another aspect of the invention provides stimulation systems and methods for the treatment of sexual dysfunction. The systems and methods comprise at least one elongated target nerve A lead sized and configured to be coupled to a pulse generator and implanted in tissue, the target nerve A lead including at least one target nerve A stimulation electrode sized and configured to be implanted in a tissue region at or near a target nerve A, at least one elongated target nerve B lead sized and configured to be coupled to a pulse generator and implanted in tissue, the target nerve B lead including at least one target nerve B stimulation electrode sized and configured to be implanted in a tissue region at or near a target nerve B, and at least one pulse generator to convey electrical stimulation waveforms to each of the target nerve A stimulation electrode and target nerve B stimulation electrode to stimulate the target nerve A and the target nerve B to treat sexual dysfunction.

The pulse generator may be an implantable pulse generator or the pulse generator may be an external pulse generator, or a combination of an implantable pulse generator and external pulse generator may be used. The target nerve A and the target nerve B to be stimulated may be efferent nerves.

In an additional aspect of the invention, the electrical stimulation waveform may be conveyed to the target nerve A electrode for a first predetermined amount of time, and then the stimulation waveform may be conveyed to both the target nerve A electrode and the target nerve B electrode for a second predetermined amount of time.

In yet an additional aspect of the invention, the electrical stimulation waveform may be conveyed to the target nerve A electrode for a first predetermined amount of time, and then the stimulation waveform may be conveyed to both the target nerve A electrode and the target nerve B electrode for a second predetermined amount of time, and then the stimulation waveform may be conveyed only to the target nerve A electrode for a third predetermined amount of time.

In yet an additional aspect of the invention, the electrical stimulation waveform may be conveyed to the target nerve A electrode for a first predetermined amount of time, and then the stimulation waveform may be conveyed to both the target nerve A electrode and the target nerve B electrode for a second predetermined amount of time, and then the stimulation waveform may be conveyed only to the target nerve B electrode for a third predetermined amount of time.

In one aspect of the invention, the electrical stimulation waveform conveyed to the target nerve A electrode comprises one or more waveform parameters that are different than the electrical stimulation waveform conveyed to the target nerve B electrode. The electrical stimulation waveform parameters may include amplitude; frequency; pulse width; pulse shape; pulse phase; stimulus on time; stimulus off time; ramp up; ramp down; amplitude modulation; frequency modulation; pulse modulation; variability; and delay, or any combination.

The electrical stimulation waveform may also comprise one or more variable stimulus parameters to improve and/or optimize the desired response. The variable stimulus parameters may include a variable frequency component; a variable duty cycle component; a variable amplitude component; a variable pulse width component; a variable pulse shape component; variable pulse phase component; a variable stimulus on time component; a variable stimulus off time component; a variable ramp up component; a variable ramp down component; a variable amplitude modulation component; a variable frequency modulation component; a variable pulse modulation component; a variable sequence component; and a variable delay component, or any combination.

Other features and advantages of the inventions are set forth in the following specification and attached drawings.

BRIEF DESCRIPTION OF THE DRAWINGS

FIG. 3 is an end section view of the penis taken generally along line 3-3 of FIG. 2.

FIG. 4 is a side sectional view of penile tissue prior to an erection.

FIG. 5 is a side sectional view of penile tissue as shown in FIG. 4, showing the changes in the penile tissue causing an erection.

FIG. 6 is a timing chart showing one possible timing scheme for stimulation of a target nerve A and a target nerve B for restoration of sexual functions.

FIGS. 7 through 12 are anterior anatomic views of multiple embodiments of the system after implantation in a pelvic region for restoration of sexual functions.

FIG. 13 is a plane view of an implant system for treating sexual dysfunction in humans and animals.

FIG. 60A is a perspective view of a stimulating catheter adapted for stimulation of target nerves near the urethra for both males and females.

FIG. 60B is a detailed plan view of an electrode secured to the catheter body of the stimulating catheter shown in FIG. 60A.

FIG. 61 is a cross-sectional view taken along lines 61-61 of FIG. 60A, showing a two lumen configuration used in conjunction with the stimulating catheter.

FIG. 62 is a cross-sectional view taken along lines 62-62 of FIG. 60A, showing an electrode used in conjunction with the stimulating catheter.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with the restoration of sexual function (e.g., erection, ejaculation, orgasm, vaginal lubrication, arousal, and engorgement) by the unilateral or bilateral stimulation of a target nerve A and/or a target nerve B of either the male or the female animal, including humans, using one or more leads implanted in tissue in a region at or near the target nerve(s). That is because the features and advantages of the invention are well suited for this purpose. Still, it should be appreciated that the various aspects of the invention can be applied in other forms and in other locations in the body to achieve other objectives as well. These objectives pertain to both male and female, human and animal, and may include, but are not limited to, erection, ejaculation, orgasm, vaginal lubrication, arousal, and engorgement.

I. System Overview

A. Neuromodulation Stimulation

Figure 1:
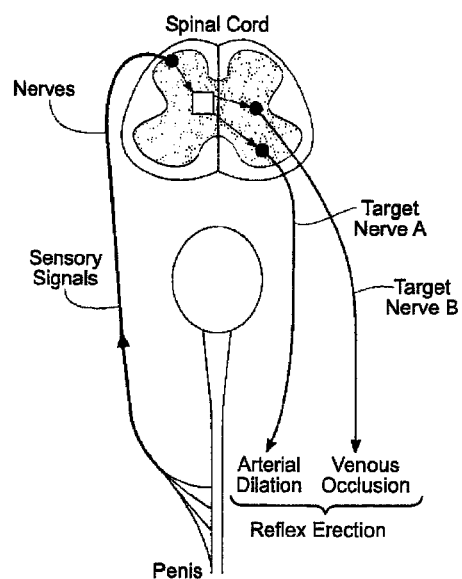
FIG. 1 is a schematic view of sensory signals and the spinal circuitry activity that coordinates efferent nerve activity for restoration of sexual functions.
Figure 2:
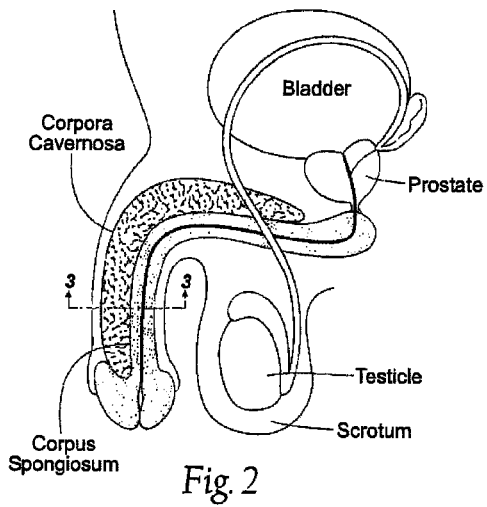
FIG. 2 is a lateral cross-sectional view of a penis, showing the relationship of the erectile tissue inside the penis.
Figure 7:
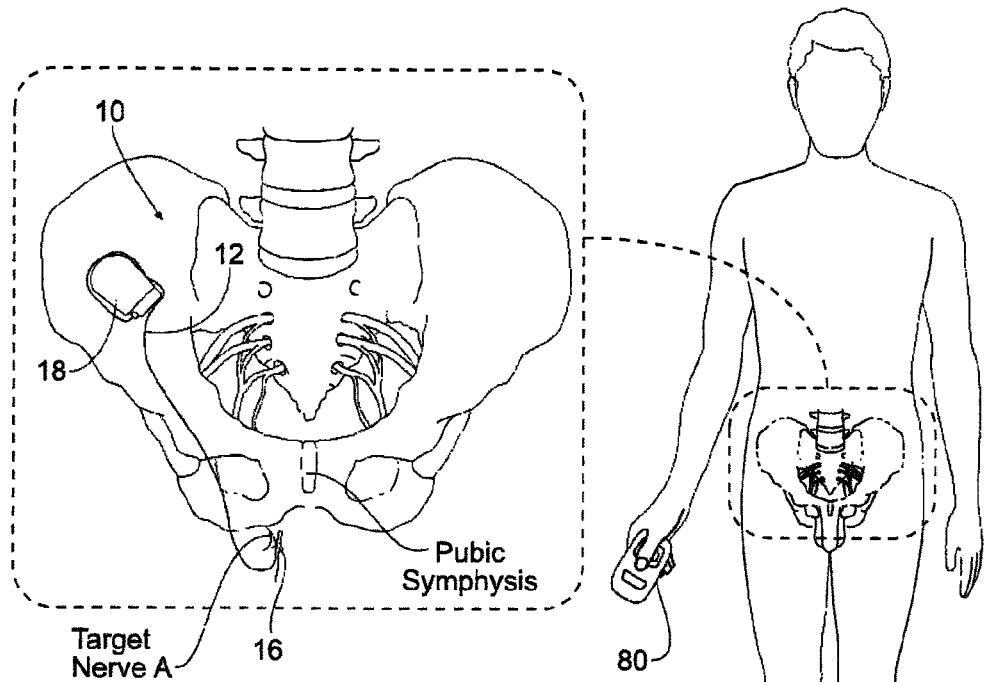
Figure 8:
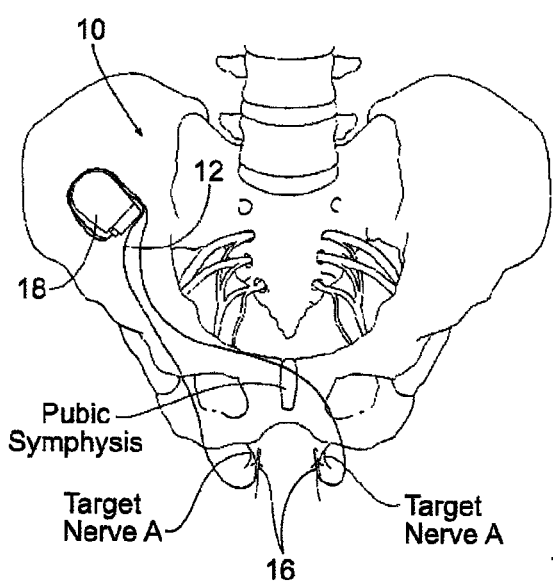
Figure 9:
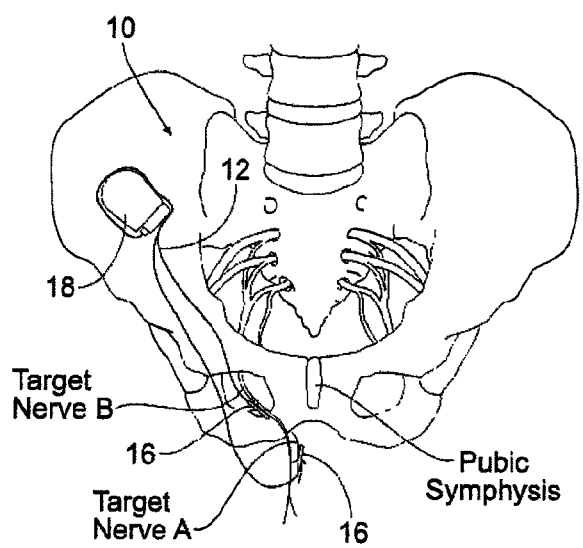

In a healthy individual, sensory signals are sent to reflex circuitry during coitus. The reflex circuitry then coordinates the 1) increase in blood flow into the penis via dilation of penile arteries with the 2) decrease in blood flow exiting the penis via occlusion of penile veins (see FIG. 1).

As previously described, activation of efferent fibers of the cavernous nerve (a parasympathetic nerve) causes relaxation of corporeal smooth muscle of the cavernosal and trabecular spaces and generates the arterial dilation. Penile erection begins with the filling and expansion of the three erectile bodies: the corpus spongiosum and the two corpora cavernosa. This expansion compresses the venules against the tunica albuginea, preventing blood from leaving the penis and furthering the erection by way of intrinsic venous occlusion (within the penis). Extrinsic venous occlusion (outside the penis) is provided by activation of the pudendal nerve (a somatic nerve), which causes contraction of the bulbospongiosus and ischiocavernosus muscles, trapping the blood in the penis erectile tissues and increasing tumescence.

Target nerve A will be used herein to describe one or more efferent nerve pathways that may be electrically activated or stimulated to initiate, increase, and/or sustain arterial dilation to produce an erection response. The efferent fibers or pathways may be activated by stimulation of any nerve(s) of the pelvis including the cavernous nerve; the prostatic plexus; the pelvic nerve (also known as nervus erigens, nervi erigentes, and nervus erigentes); hypogastric nerve; and the splanchnic nerve (pelvic splanchnic nerve), for example. In the female, these nerves may be called something else, but the mechanism is the same. These pathways may also be activated by stimulation of any sacral, or lumbar root which supplies any of these nerves of the pelvis, and/or any branch of any of these nerves. Any combination of these genital nerves and/or their spinal, sacral, lumbar, and/or thoracic roots and/or branches will be referred to as the target nerve A.

Target nerve B be used herein to describe one or more efferent nerve pathways that may be electrically activated or stimulated to initiate, increase, and/or sustain venous occlusion to enhance the erection response. The efferent fibers or pathways may be activated by stimulation of any nerve(s) of the pelvis including the pudendal nerve and/or the perineal nerve, for example, and/or the nerves that innervate the ischiocavernosus, bulbocavernosus, and/or bulbospongiosus muscles and the transverse perineal muscle(s). In the female, these nerves may be called something else, but the mechanism is the same. These pathways may also be activated by stimulation of any spinal, sacral, or lumbar root which supplies any of these nerves of the pelvis, and/or any branch of any of these nerves. Any combination of these genital nerves and/or their spinal, sacral, lumbar, and/or thoracic roots and/or branches will be referred to as the target nerve B.

The erection may be enhanced by stimulation of afferent pathway(s), which may be activated by stimulation of any nerve(s) of the pelvis including the dorsal penile nerve; the medial, lateral, and posterior scrotal branches of the perineal nerve; the ilioinguinal nerve; the rectal nerve; and the perineal branch of the posterior femoral cutaneous nerve. These pathways may also be activated by stimulation of any spinal, sacral, or lumbar root which supplies any of these nerve(s) and/or by any branch of any of these nerve(s).

The erectile function may be activated or enhanced with neuromodulation (i.e., electrical) stimulation. For example, a target nerve A may be electrically stimulated, either continuous or intermittent, and either unilateral or bilateral, to increase blood flow into and/or decrease blood flow out of the penis and/or the erectile tissue. This may increase pressure in the erectile bodies, and cause an erection sufficient for intercourse.

In addition, a target nerve B may be electrically stimulated, either continuous or intermittent, and either unilateral or bilateral, to increase blood flow into and/or decrease blood flow out of the penis and/or the erectile tissue. Stimulation of a target nerve B may also increase pressure in the erectile bodies, and cause an erection sufficient for intercourse.

As an additional option, both a target nerve A and a target nerve B may be electrically stimulated, either continuous or intermittent, and either unilateral or bilateral, or one unilateral and the other bilateral, to increase blood flow into and/or decrease blood flow out of the penis and/or the erectile tissue. The electrical stimulation of a target nerve B may be applied after target nerve A stimulation has started, or target nerve B stimulation may be applied prior to target nerve A stimulation, or simultaneously with target nerve A stimulation, but a desired method is to start with target nerve A stimulation and then follow with target nerve B stimulation. Target nerve A stimulation may be able to evoke full erection, and when target nerve B stimulation is included (possibly with target nerve A stimulation still on), penile rigidity may be increased even further to produce a more rigid erection.

For example, stimulation may be applied to target nerve A for a predetermined period, and then stimulation may also be applied to target nerve B. Thus stimulation would initially be applied only to target nerve A and then stimulation would be applied simultaneously to both target nerves A and B (see FIG. 6).

In a desired embodiment, the predetermined time for stimulation of target nerve A prior to stimulation of a target nerve B may be about 30 seconds to about 2 minutes, or to about 5 or 10 minutes. This timing may be adjustable in order to produce the most desired result.

One possible advantage of intermittent target nerve B stimulation is to reduce the risk of ischemia (local deficiency of blood supply produced by vasoconstriction or local obstacles to the arterial flow) or tissue damage that can result from the nearly complete venous occlusion produced by target nerve B stimulation.

In general, target nerve A stimulation may increase tumescence, and target nerve B stimulation may also increase tumescence. Combining target nerve A stimulation with target nerve B stimulation may produce tumescence that is superior to the tumescence produced by either target nerve A stimulation alone or by target nerve B stimulation alone. The term "superior" may define an erection that occurs quicker, lasts longer, is more rigid, is more reliable (e.g., a greater number of attempts at intercourse result in success or penetration), remains rigid more consistently for the duration of stimulation (i.e., erection is less likely to be lost while stimulation is on), appears to be more natural (e.g., looks and/or feels more like the erections the user may have experienced prior to erectile dysfunction), and/or is perceived as more satisfactory by the user and/or the partner(s) of the user and/or the user's healthcare provider(s) and/or clinician(s).

The target nerve B stimulation may decrease venous outflow of blood from the penis and/or force more blood into the penis and/or erectile tissue. Target nerve B stimulation may increase the rigidity of the erection and/or extend the duration of the erection and/or quicken the rise in pressure in the erectile bodies and/or hasten the onset of erection. Target nerve B stimulation may also transform partial erections or erections unsuitable for intercourse (e.g., vaginal, anal, and/or oral intercourse) into erections that are sufficient for intercourse.

An implant system will be used to provide electrical stimulation of a target nerve A and/or a target nerve B to provide sustainable erections on-demand with a simple surgical procedure that preserves the existing anatomy.

As used in this disclosure, it is to be appreciated that at least the terms "nerve", "lead", "electrode", and "IPG" can include both the singular or plural meaning.

The electrical stimulation may be applied with any type of electrical contact such as one or more leads having one or more electrodes placed in, on, around, or near (i.e., within activation range) any of the target nerves A and/or target nerves B named above. The lead may also include the ability to deliver medications or drugs as an adjunct to electrical stimulation. Note that the electrode may be in contact with the target nerve, or it may be some distance (on the order of centimeters) away because it does not have to be in contact with the target nerve to activate it.

Stimulation may be applied through a lead/electrode, such as a fine wire electrode, paddle electrode, intramuscular electrode, or general purpose electrode, inserted via a needle introducer or surgically implanted in proximity of the target nerve. Proper placement may be confirmed by any of a variety of indications including patient sensation; transduction and/or measurement of one or more physiological event(s) or property(ies), such as electromyogram (EMG), local or systemic blood pressure (venous and/or arterial), pressure in related tissues or structures (e.g., the corpus cavernosum and/or corpus spongiosum), genital diameter, girth, length, rigidity, engorgement, temperature, and/or color; or visible movement of related organ(s) such as the penis, scrotum, perineal perineal skin, and/or anal sphincter, (or clitoris for women). Once proper placement is confirmed, the needle may be withdrawn, leaving the electrode in place. Stimulation may also be applied through a penetrating electrode, such as an electrode array comprised of any number one or more) of needle-like electrodes that are inserted into the target nerve. In both cases, the lead may placed using a needle-like introducer, allowing the lead/electrode placement to be minimally invasive.

Alternatively, or in combination, stimulation may be applied through any type of nerve cuff (spiral, helical, cylindrical, book, flat interface nerve electrode (FINE), slowly closing FINE, etc.) that is surgically placed on or around a target nerve.

In all cases, the lead may exit through the skin and connect with one or more external stimulators, or the lead(s) may be routed subcutaneously to one or more implanted pulse generators (IPG), or they may be connected as needed to internal and external coils. The IPG may be located some distance (remote) from the electrode, or the IPG may be integrated with the electrode, eliminating the need to route the lead subcutaneously to the IPG.

Control of the stimulator and stimulation parameters may be provided by one or more external controllers. In the case of an external stimulator, the controller may be integrated with the external stimulator. The IPG external controller (i.e., clinical programmer) may be a remote unit that uses RE (Radio Frequency) wireless telemetry communications (rather than an inductively coupled telemetry) to control the IPG. The external or implantable pulse generator may use regulated voltage (e.g., 10 mV to 20 V), regulated current (e.g., about 10 µA to about 50 mA), and/or passive charge recovery to generate the stimulation waveform.

The pulse may by monophasic, biphasic, and/or multiphasic. In the case of the biphasic or multi-phasic pulse, the pulse may be symmetrical or asymmetrical. Its shape may be rectangular or exponential or a combination of rectangular and exponential waveforms. The pulse width of each phase may range between e.g., about 0.1 µsec. to about 1.0 sec.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from e.g., about 1 Hz to about 300 Hz, and the frequency of stimulation may be constant or varying. In the case of applying stimulation with varying frequencies, the frequencies may vary in a consistent and repeatable pattern or in a random (or pseudo random) fashion or a combination of repeatable and random patterns.

The stimulation pulses could be applied to a left target nerve and a right target nerve with different parameters, or the stimulation pulses could be applied to different branches of the same target nerve at different parameters, such as different frequencies, to provide the best response. For example, the left target nerve A could be stimulated at three Hz, and the right target nerve A could be stimulated at five Hz.

B. The Implant System

FIGS. 7 through 12 show multiple embodiments of an implant system 10 for the restoration of sexual function in animals, including humans. As shown, multiple implant system configurations are possible. As non-limiting examples, a single IPO 18 may be coupled to a single lead 12 to unilaterally stimulate a single target nerve (either A or B) (see FIG. 7); or a single IPG may be coupled to two leads to bilaterally stimulate a single target nerve (either A or B) (see FIG. 8); or a single IPG may be coupled to two leads to unilaterally stimulate a target nerve A and target nerve B (see FIG. 9); or two IPGs may be implanted, each being coupled to a single lead to bilaterally stimulate a single target nerve (either A or B) (see FIG. 10); or two IPGs may be implanted, each being coupled to a single lead to unilaterally stimulate a target nerve A and target nerve B (see FIG. 11); or two IPCs may be implanted, each being coupled to two leads to bilaterally stimulate a target nerve A and a target nerve B (see FIG. 12). It is to be appreciated that additional system configurations exist.

Referring to FIG. 13, the system 10 includes at least one implantable lead 12 having a proximal end and a distal end, the distal end being coupled to an implantable pulse generator or IPG 18. The lead 12 and the implantable pulse generator 18 are shown implanted within a pelvic region of a human or animal body, although other implant sites are possible.

In the embodiment shown, the distal end of the lead 12 includes at least one electrically conductive surface, which will in shorthand be called an electrode array or electrode 16. The electrode 16 is implanted in electrical conductive contact with at least a target nerve A and/or a target nerve B. The implantable pulse generator 18 includes a connection header 14 that desirably carries a ping-in receptacle 15 (connector) for the distal end of the lead 12. In this way, the lead 12 electrically connects the electrode 16 to the implantable pulse generator 18.

The lead 12 and electrode 16 are sized and configured to be implanted percutaneously in tissue, and to be tolerated by an individual during extended use without pain or discomfort. The comfort is both in terms of the individual's sensory perception of the electrical waveforms that the electrode applies, as well as the individual's sensory perception of the physical or mechanical presence of the electrode and lead. In the case of the mechanical presence, the lead 12 and electrode 16 are desirably "imperceptible."

In particular, the lead 12 and electrode 16 are sized and configured to reside with stability in the lower pelvic region of the body (see FIGS. 7 through 12). It has been discovered that, when properly placed in this region, one or more lead/electrode(s) are uniquely able to deliver electrical stimulation current to a target nerve A and/or a target nerve B to treat sexual dysfunction.

FIGS. 14A and 14B, and 15A and 15B, show multiple embodiments of an implantable pulse generator 18 of the present invention, and will be described in greater detail later. The implantable pulse generator 18 includes a circuit 20 that generates electrical stimulation waveforms. An on-board, primary or rechargeable battery 22 desirably provides the power. The implantable pulse generator 18 also desirably includes an on-board, programmable microcontroller 24, which carries embedded code. The code expresses pre-programmed rules or algorithms under which the desired electrical stimulation waveforms are generated by the circuit 20. The implantable pulse generator 18 may also include an electrically conductive case 26, which can also serve as the return electrode for the stimulus current introduced by the lead/electrode when operated in a monopolar configuration.

The pulse generator 18 is sized and configured to be implanted subcutaneously in tissue at an implant depth of between about five millimeters and about twenty millimeters, desirably in a subcutaneous pocket remote from the electrode 16 (see FIG. 16) and using a minimally invasive surgical procedure. This implant depth may change due to the particular application, or the implant depth may change over time based on physical conditions of the patient. As shown in FIGS. 7 through 12, the implantation site can comprise a generally medial tissue region in the lower abdomen. There, the pulse generator 18 can reside for extended use without causing pain and/or discomfort and/or without effecting body image. Alternatively, the implantation site can comprise a tissue region on the posterior hip, for example.

The implant system 10 may include an external patient controller 80 (or controller-charger when a rechargeable battery is used). The patient controller 80 is sized and configured to be held or worn by the individual to transcutaneously activate and deactivate and/or modify the output of the pulse generator 18 (see FIGS. 16 and 17). The patient controller 80 may, e.g., be a simple magnet that, when placed near the site where the pulse generator 18 is implanted, toggles a magnetic switch within the implantable pulse generator 18 between an on condition and an off condition, or advances through a sequence of alternative stimulus modes pre-programmed by the clinician into the implantable pulse generator 18.

Alternatively, the patient controller 80 may comprise more sophisticated circuitry that would allow the individual to make these selections through RF (Radio Frequency) wireless telemetry communications (rather that an inductively coupled telemetry) that passes through the skin and tissue within an arm's length distance from the implanted pulse generator, e.g., the controller 80 is capable of communicating with the pulse generator 18 approximately three to six feet away from the implanted pulse generator (and the pulse generator is able to communicate with the controller).

The wireless telemetry 82 provides reliable, bidirectional communications with a patient controller-charger and a clinical programmer, for example via an RF link in the 402 MHz to 405 MHz Medical Implant Communications Service (MICS) band per FCC 47 CFR Part 95, or other VHF/UHF low power, unlicensed bands.

With the use of the patient controller 80 (see FIGS. 16 and 17), the wireless link 82 allows a patient to control certain parameters of the implantable pulse generator within a predefined limited range. The parameters may include the operating modes/states, increasing/decreasing or optimizing stimulus patterns, or providing open or closed loop feedback from one or more internal and/or external sensors and/or control source. The wireless telemetry 82 also desirably allows the user to interrogate the implantable pulse generator 18 as to the status of its internal battery 22 (either primary or rechargeable). The full ranges within these parameters may be controlled, adjusted, and limited by a clinician, so the user may not be allowed the full range of possible adjustments.

In one embodiment, the patient controller 80 is sized and configured to couple to a key chain. It is to be appreciated that the patient controller 80 may take on any convenient shape, such as a ring on a finger, or a watch on a wrist, or an attachment to a belt or keychain, for example. The patient controller may also use a magnetic switch to enable the user to turn the IPG on/off.

The clinical programmer 52 (described in greater detail in section "III. Clinical Tools") is used by a clinician to program the pulse generator 18 with a range of preset stimulus parameters. The user will then turn the implant system On/Off using the wireless patient controller 80. The controller 80 is then programmed by the pulse generator, i.e., the range of or a subset of the preset stimulus parameters previously downloaded by the clinical programmer 52 is uploaded to the controller 80. This range of preset stimulus parameters allows the user to make adjustments to the stimulus strength within the preset range. Stimulation will be delivered at a level that is initially set at or above the sensory threshold of the user, but is not uncomfortable. The user may get accustomed to the stimulation level, and may adjust the stimulation up or down within the preset range.

According to its programmed rules, when switched on, the implantable pulse generator 18 generates prescribed stimulation waveforms through the lead 12 and to the electrode 16. These waveforms stimulate a target nerve A and/or a target nerve B in a manner that achieves the desired physiologic response.

Using the controller 80, the individual may turn on or turn off the sexual restoration control waveforms at will or adjust the waveforms to achieve the desired functional restoration result. As previously discussed, erectile restoration is just one example of a functional restoration result. Additional examples of desirable therapeutic (treatment) or functional restoration indications will be described in section "XI. Representative Indications."

The system 10 desirably includes means for selectively varying the frequency or range of frequencies for a variable duration at which the stimulation waveforms are applied by the one or more electrodes 16. By modulating the frequency and/or duration of the stimulation waveform, the same system components and placement of electrodes can serve to achieve markedly different physiologic responses, and in addition, reduce habituation.

The shape of the waveform can vary as well. It can, e.g., be a typical square pulse, or possess a ramped shape. The pulse, or the rising or falling edges of the pulse, can present various linear, exponential, hyperbolic, or quasi-trapezoidal shapes. The stimulation waveform can be continuous, or it can be variable and change cyclically or in step fashion in magnitude and waveform over time.

In a non-limiting exemplary embodiment, the stimulus waveforms may include a variable frequency for a variable duration (e.g., a first stimulation at 5 Hz for 2 seconds, then 7 Hz for 3 seconds, then 6 Hz for 1 second, and so on), intermittent stimulation (apply stimulation in bursts separated by pauses in stimulation (e.g., stimulation for 3 seconds, rest for 2 seconds, repeat, and so on). The stimulus waveforms may also include a continuously or intermittently applied duty cycle of pulses. This may be considered the same as changing the frequency but it also refers to: 1) the duration of bursts of stimulation, and 2) the duration of pauses between the bursts. For example, a variable duty cycle for intermittent pulses may include stimulation with 10 pulses, then off for 500 milliseconds, stimulation with 15 pulses, then off for 750 milliseconds, stimulation with 5 pulses, then off for 2 seconds, and it could keep going in this variable pattern.

The stimulus waveforms may also include stimulation at different amplitudes and different frequencies. This may be beneficial because increasing the amplitude may increase penile tumescence to a certain degree, and then increasing the amplitude further may be used to cause ejaculation. Thus, amplitude and/or frequency modulation may be used to control the response varying the amplitude and/or frequency may also provide another form of anti-habituation control, allowing a sexual function erection) to remain more robust than if a target nerve was stimulated at a constant amplitude. Amplitude and/or frequency modulation may also more realistically recreate the varying level of fiber activation that occurs during coitus.

The patient controller 80 and/or the clinical programmer 52, for example, may include a manual-actuated switch or control knob which an operator operates or tunes to acquire a desired waveform amplitude and/or frequency, given the desired physiologic response.

C. Conditions Required to Evoke Erection

Erection is a complex process involving control from the autonomic and somatic nervous systems. There are two peripheral neural pathways that control erection in cats and dogs. The parasympathetic pathway (S2-S5) mediates tactile, as well as psychically induced erection, while the sympathetic pathway (T10-L2) mediates psychically induced erection. These neural pathways are believed to be generally reflective of human neural pathways as well, although variations of these neural pathways may exist. Although erection involves many central and psychogenic factors, reflex erections are mediated by a spinal mechanism, and do not require participation of supraspinal structures.

The implant system 10 will focus on efferent stimulation, but afferent stimulation may also evoke or enhance the response. The afferents of the erection reflex arises primarily from the dorsal nerve of the penis, while the efferent side includes both target nerves A and target nerves B (see FIG. 1). A target nerve A mediates engorgement of the penis as a result of dilation of penile blood vessels (mediated by a non-adrenergic non-cholinergic mechanism, putatively nitric oxide), and venous occlusion may also play a role in engorgement. A target nerve B carries the somatic innervation of the bulbospongiosus which serves to further increase cavernous pressure and penile stiffness, and the ischiocavernosus which can also augment stiffness of the penis. Present stimulation methods do not stimulate both a target nerve A and a target nerve B (or their respective nerve branches).

Stimulation of a target nerve A and/or a target nerve B to generate a desired efferent response (such as increase arterial inflow or increase venous occlusion to the penis) may also generate an unwanted afferent signal that could trigger an unwanted response such as pain. If a stimulation signal configuration causes a pain sensation, the unwanted afferent signal may be blocked to prevent the perception of pain. To prevent the perception of pain, a blocking stimulus, such as high frequency block, may be used. One aspect of the invention includes lead/electrode array configurations adapted to provide high frequency block with one (or more) electrode to prevent the unwanted afferent response, and a second (or more) electrode to provide the stimulation that evokes the desired efferent response (to be discussed in greater detail in section "E. Stimulating and Blocking Electrodes").

The implant system 10 is sized and configured to evoke a rigid erection and sustain an erection for about 30 minutes that is comparable in both 1) corpus cavernous pressure (CCP) and 2) CCP/BP (blood pressure) to the erection produced by intracavernous injection of alprostadil. A rigid erection is defined by CCP≥BP and a functional score of 4 or 5 (sufficient for sexual intercourse or full erection) on the Schramek grading system. The time to erection once the implant system 10 is turned on may be in the range of less than a minute to about ten minutes, for example. When the implant system is turned off, the erection will subside comparable to a normal a healthy response.

II. The Implantable Pulse Generator

As previously described, FIGS. 7 through 12 show embodiments of a system 10 adapted for the functional restoration of sexual function. The assembly includes at least one implantable lead 12 and electrode array 16 coupled to at least one implantable pulse generator or IPG 18. The lead 12 and the implantable pulse generator 18 are shown implanted within a pelvic region of a human or animal body.

Certain components of the implantable pulse generator 18 may be expected to change as the indication changes. For example, due to differences in leads and electrodes, the connection header 14 and associated receptacle(s) for the lead may be configured differently for different indications. Other aspects of the circuit 20 may also be modified to accommodate a different indication; for example, the stimulator output stage(s), sensor(s) and/or sensor interface circuitry. In addition, the case size may change due to a different header configuration and/or a desire to increase or decrease the battery size or capacity (compare FIGS. 14A and 14B to 15A and 15B).

The implantable pulse generator 18 may be of the type described in commonly owned U.S. Patent Publication No. 2007-0060955, published Mar. 15, 2007, entitled "Implantable Pulse Generator Systems and Methods for Providing Functional and/or Therapeutic Stimulation of Muscles and/or Nerves and/or Central Nervous System Tissue," which is incorporated herein by reference. The pulse generator 18 includes a circuit that generates electrical stimulation waveforms. An on-board battery 22 (primary or rechargeable) provides the power. The pulse generator 18 also includes an on-board, programmable microcontroller 24, which carries embedded code. The code expresses pre-programmed rules or algorithms under which the desired electrical stimulation waveforms are generated by the circuit. The small metal case (e.g., titanium) of the pulse generator may also serve as the return electrode for the stimulus current introduced by the lead/electrode when operated in a monopolar configuration.

Figure 14A:
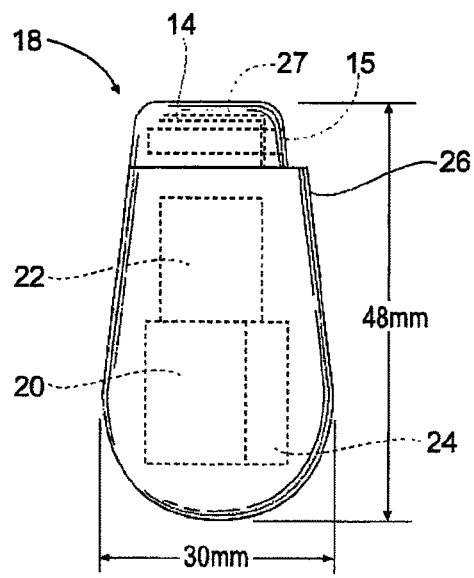
FIGS. 14A and 14B are front and side views of one embodiment of the general purpose implantable pulse generator shown in FIG. 13, which may be powered by a primary or rechargeable battery.
Figure 14B:
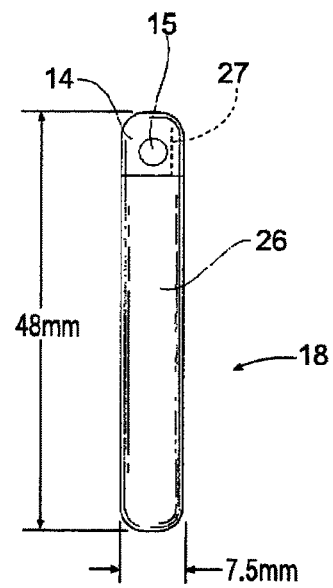

The functional elements of the implantable pulse generator 18 (e.g., circuit 20, the microcontroller 24, the battery 22, and the connection header 14) are integrated into a small, composite case 26. Referring to FIGS. 14A and 14B, the case of the pulse generator 18 defines a small cross section; e.g., desirably about (5 mm to 10 mm thick).times.(15 mm to 40 mm wide).times.(40 mm to 60 mm long), and more desirably about (7 mm to 8 min thick).times.(25 mm to 35 mm wide).times.(45 mm to 55 mm long). The pulse generator also defines a generally pear-shaped case. The generally pear-shaped case can be described as including a bottom portion defining a curved surface having a radius, inwardly tapering sides, and a top portion being generally flat, as shown in FIGS. 14A and 14B. This geometry provides a case including a larger end (bottom portion) and a smaller end (top portion) and allows the smaller end of the case to be placed into the skin pocket first, with the larger end being pushed in last. The shape and dimensions of the pulse generator 18 produce a volume of approximately seven to nine cubic centimeters, and more desirably about eight cubic centimeters, and a weight of approximately seventeen grams.

Figure 15A:
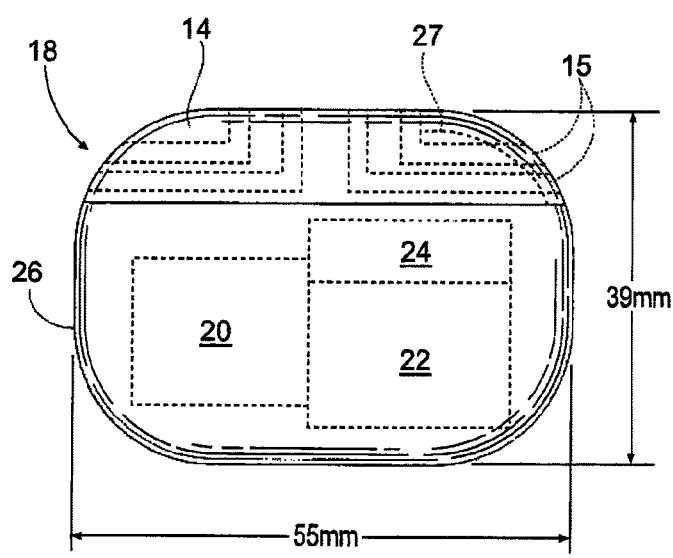
FIGS. 15A and 15B are front and side views of an alternative embodiment of the general purpose implantable pulse generator as shown in FIG. 13, which may be powered by a primary or rechargeable battery.
Figure 15B:
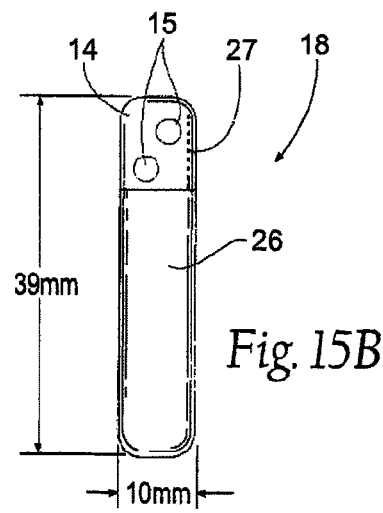

In an alternative embodiment seen in FIGS. 15A and 15B, the case of the pulse generator 18 defines a small cross section; e.g., desirably about (7 mm to 13 mm thick).times.(45 mm to 65 mm wide).times.(30 mm to 50 mm long), and more desirably about (9 mm to 11 mm thick).times.(50 mm to 60 mm wide).times.(35 mm to 45 mm long). The pulse generator also defines a generally oval-shaped case. The generally oval-shaped case can be described as consisting generally of two congruent semicircles and two equal and parallel lines. The shape and dimensions of the pulse generator 18 produce a volume of approximately fifteen to nineteen cubic centimeters, and more desirably about seventeen cubic centimeters, and a weight of approximately twenty-seven grams.

Figure 18:
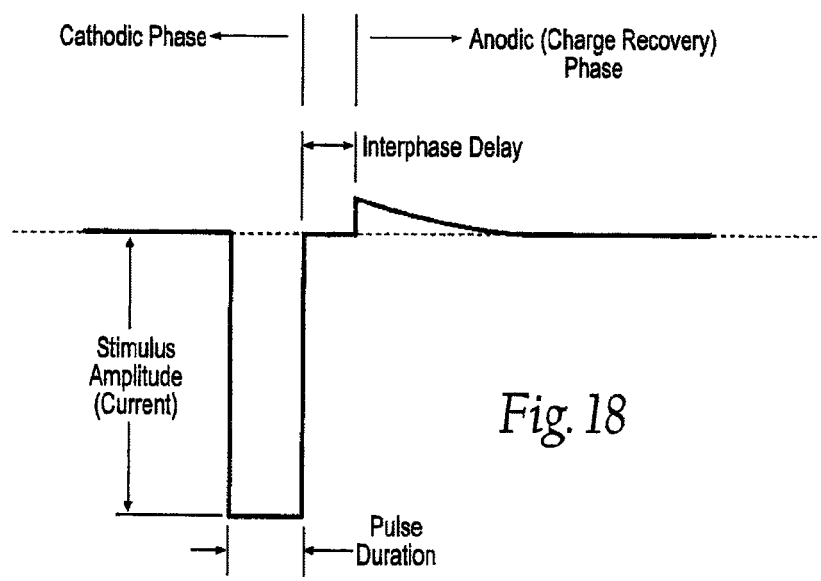
FIG. 18 is a graphical view of a desirable biphasic stimulus pulse output of the implantable pulse generator for use with the system shown in FIG. 1.

The pulse generator 18 can deliver a range of stimulation parameters to the lead 12 and electrode 16, e.g., output current ranges of about 10 µA to about 50 mA, pulse width ranges of about 0.1 µsec. to about 1.0 sec., frequency ranges of about 1 Hz to about 300 Hz, and duty cycle ranges from about zero to about 100 percent. In one embodiment, the delivered stimulus may be an asymmetric biphasic waveform with zero net DC (direct current). A typical, biphasic stimulus pulse is shown in FIG. 18.

The implantable pulse generator 18 desirably incorporates circuitry and/or programming to assure that the implantable pulse generator 18 will suspend stimulation, and perhaps fall-back to only very low rate telemetry, and eventually suspends all operations when the battery 22 has discharged the majority of its capacity (i.e., only a safety margin charge remains). Once in this dormant mode, the implantable pulse generator may provide limited communications and is in condition for replacement if a primary battery is used, or it must be recharged. When a primary (non-rechargeable) battery is used, the battery may have a capacity as small as about 0.5 A-hr and up to about 1.0 A-hr or more.

When a rechargeable battery is used, the battery may have a capacity as small as about 30 mA-hr and up to about 120 mA-hr or more, and recharging of the rechargeable battery is required less than weekly. When the rechargeable battery has only a safety margin charge remaining, it can be recharged in a time period of not more than six hours.

The patient controller 80 may also be belt or clothing worn and used to charge the rechargeable batteries of the pulse generator 18 as needed. Charging is achieved via an inductive RF link using a charge coil on or near the skin in close proximity to the IPG. The patient controller 80 may also be configured to provide the user with information on pulse generator battery status and stimulus levels.

The implantable pulse generator 18 desirably includes a lead connection header 14 (see FIGS. 14A to 15B), for connecting the lead(s) 12 that will enable reliable and easy replacement of the lead/electrode, and includes a small antenna 27 for use with the wireless telemetry feature. Metal-ceramic or metal-glass feed-thrus maintain the hermetic seal of the titanium capsule while providing electrical contact to the electrical contacts of the lead 12/electrode 16.

The standard implantable connectors may be similar in design and construction to the low-profile IS-1 connector system (per ISO 5841-3). Full compatibility with the IS-1 standard, and mating with pacemaker leads, is not a requirement for the implantable pulse generator.

The implantable pulse generator connection system may include a modification of the IS-1 connector system, which shrinks the axial length dimensions while keeping the format and radial dimensions of the IS-1. For application with more than two electrode conductors, the top header 14 may incorporate one or more connection receptacles each of which accommodate leads with typically four conductors. When two or more leads are accommodated by the header, these leads may exit the connection header in opposite directions (i.e., from opposite sides of the header), as seen in FIGS. 15A and 15B.

These connectors can be similar to the banded axial connectors used by other multi-polar implantable pulse generators or may follow the guidance of the draft IS-4 implantable connector standard. The design of the implantable pulse generator housing and header 14 preferably includes provisions for adding the additional feed-thrus and larger headers for such indications.

The inclusion of the antenna 27 for the wireless telemetry inside the connection header 14 is necessary as the shielding offered by the titanium case will severely limit (effectively eliminate) radio wave propagation through the case. The antenna 27 connection will be made through a feed-thru similar to that used for the electrode connections. Alternatively, the wireless telemetry signal 82 may be coupled inside the implantable pulse generator onto a stimulus output channel and coupled to the antenna 27 with passive filtering/coupling elements/methods in the connection header 14.

III. Clinical Tools

A clinical tool system 50 is desirably provided to condition the implanted pulse generator 18 to perform in the intended manner.

Figure 19:
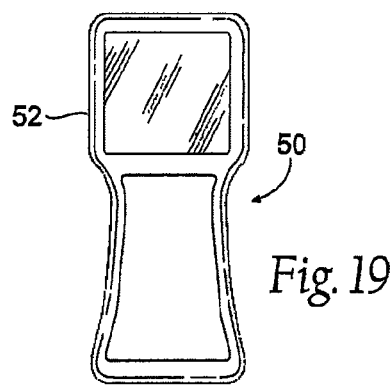
FIG. 19 is a plane view of a clinical programmer that can be used in conjunction with the system shown in FIG. 13.

In the embodiment shown in FIG. 19, the clinical tool system 50 includes a clinical programmer 52 of the type described in commonly owned U.S. Pat. No. 7,761,167, issued Jul. 20, 2010, entitled "Systems and Methods for Clinician Control of Stimulation Systems," which is incorporated herein by reference. The clinical programmer 52 can be placed into transcutaneous communication with an implanted pulse generator 18 (either inside or outside the sterile field) through wireless telemetry that provides reliable, bidirectional communications via an RF link in the 402 MHz to 405 MHz Medical Implant Communications Service (MICS) band per FCC 47 CFR Part 95, or other VHF/UHF low power, unlicensed bands (see FIG. 47), The clinical programmer 52 may incorporate a custom program operating on a handheld computer or other personal digital appliance (PDA), The clinical programmer 52 or PDA includes an on-board microprocessor powered by a rechargeable, on-board battery (not shown). The microprocessor carries embedded code which may include pre-programmed rules or algorithms that allow a clinician to remotely (i.e., wirelessly) download program stimulus parameters and stimulus sequences parameters into the pulse generator. The microprocessor of the clinical programmer 52 is also desirably able to interrogate the pulse generator and upload operational data from the implanted pulse generator.

IV. The Anatomic Landmarks

Figure 20:
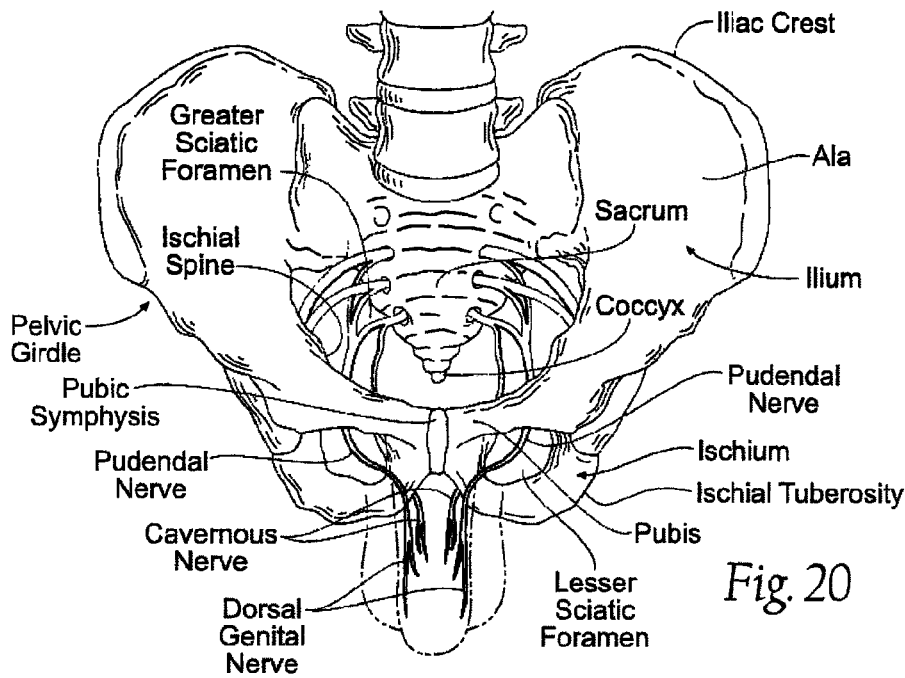
FIG. 20 is an anterior anatomic view of the pelvic girdle in a human.
Figure 21:
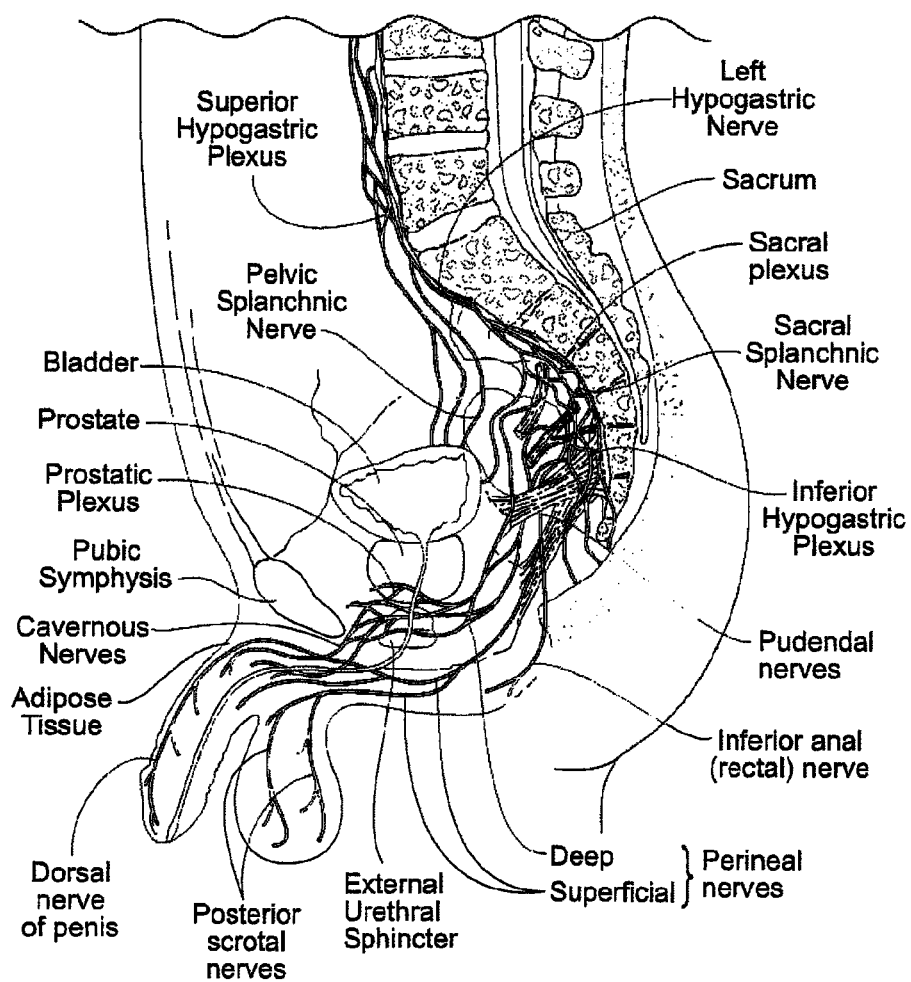
FIG. 21 is a lateral section view of the pelvic girdle region shown in FIG. 20.

As already described, certain components of the implant system 10 are sized and configured to be implanted in the lower pelvic region. As FIG. 20 shows, the hip bones are two large, irregularly shaped bones, each of which develops from the fusion of three bones, the ilium, ischium, and pubis. The ilium is the superior, fan-shaped part of the hip bone. The ala of the ilium represents the spread of the fan. The iliac crest represents the rim of the fan. It has a curve that follows the contour of the ala between the anterior and posterior superior iliac spines.

The sacrum is formed by the fusion of five originally separate sacral vertebrae. The hip bones are joined at the pubic symphysis anteriorly and to the sacrum posteriorly to form the pelvic girdle. The pelvic girdle is attached to the lower limbs. Located within the pelvic girdle are the abdominal viscera (e.g., the ileum and sigmoid colon) and the pelvic viscera (e.g., the urinary bladder and prostate gland for males, and the urinary bladder and reproductive organs such as the uterus and ovaries for females).

Within this bony frame, the cavernous nerves are either of two nerves, designated as major and minor, that extends bilaterally, in separate branches on left and right sides of the pelvic girdle. The cavernous nerves are derived from the inferior hypogastric plexus and include fibers that course through the prostatic plexus, and supply the sympathetic and the parasympathetic fibers to the corpus cavernosum. The cavernous nerves convey parasympathetic fibers out of the pelvic region. They terminate on the arteriovenous anastomoses and helicine arteries.

The pudendal nerve is derived at the sacral plexus from the anterior divisions of the ventral rami of S2 through S5 and carries afferent (sensory) and efferent (motor) nerve components that innervate muscles and organs in the lower abdomen. The pudendal nerve extends bilaterally, in separate branches on left and right sides of the pelvic girdle. Each branch accompanies the interior pudendal artery and leaves the pelvis through the left and right greater sciatic foramens between the piriformis and coccygeus muscles. The branches hook around the ischial spine and sacrospinous ligament and enter the skin and muscles of the perineum through the left and right lesser sciatic foramen.

The simpler anterior and/or perineal and/or posterior surgical implantation procedure of the present invention avoids risk of injury to the spine associated with sacral nerve stimulation. If the physician chooses to not use fluoroscopy, the patient's report of sensation, measurements of girth and/or length, the degree of erection estimated by the physician (e.g., using a grading scale such as Schramek's 1-5 grading scale and the anatomical landmarks could be used to guide placement. Other means for guidance of the placement of one or more leads may also be used, either alone or in combination with the means described above, including ultrasound, transduction, and/or measurement of one or more physiological event(s) or property(ies), such as electromyogram (EMG), local or systemic blood pressure (venous and/or arterial), pressure in related tissues or structures (e.g., the corpus cavernosum and/or corpus spongiosum), genital diameter, girth, length, rigidity, engorgement, temperature, and/or color; or visible movement of related organ(s) such as the penis, scrotum, perineal muscle, perineal skin, and/or anal sphincter, (or clitoris for women); or any diagnostic tool(s) commonly found in the suite of diagnostic tools. Implantations in the described regions are in areas in which urologists commonly operate.

Present methods of accessing target nerves A and/or B for stimulation require an open surgical procedure, but the described method is adapted to access a target nerve through a needle introducer. This procedure is less invasive than present methods, allowing it to be performed in an outpatient setting with a reduced recovery time for the patient.

V. Physician Surgical Tools

The implant system 10 shown in FIGS. 7 to 12 makes desirable a system of physician surgical tools (shown in FIGS. 22 through 24) to facilitate implantation of the implant system 10 in the intended way, desirably on an outpatient basis.

Figure 22:
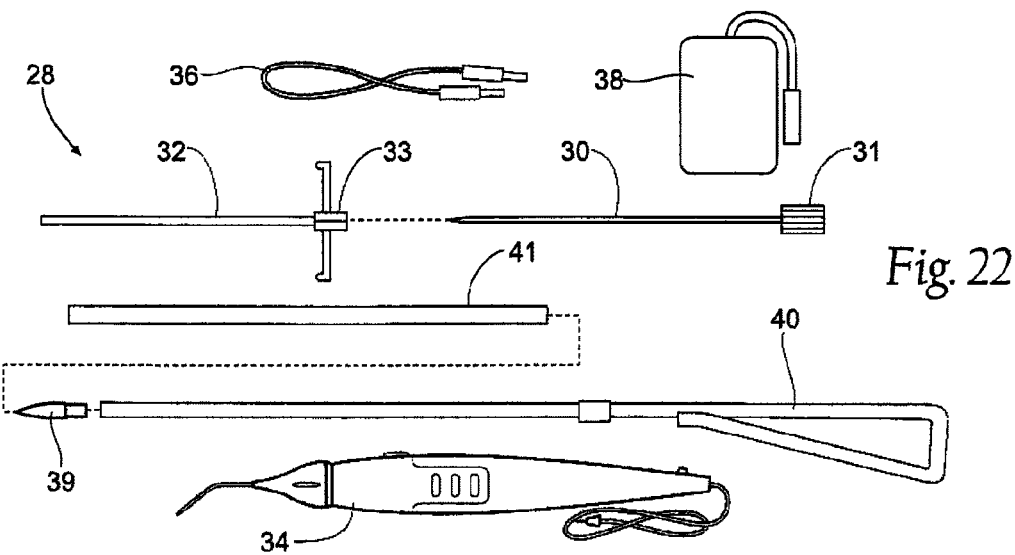
FIG. 22 is a plane view of a system of surgical tools that can be use to implant the system shown in FIG. 16.

The surgical tool system 28 shown in FIG. 22 includes tools necessary for a single stage surgical procedure (i.e., without a test screening phase), including the implantation of one or more IPGs and one or more lead/electrodes (not shown as part of the tool system 28) to stimulate a target nerve A and/or a target nerve B. The tool system 28 includes a needle 30 (or trocar) and a companion introducer sleeve 32. The needle 30 may include a luer fitting 31 to secure to a hub 33 on the introducer sleeve 32.

When the needle 30 is secured inside the sleeve 32, about one cm of the needle 30 is exposed near the hub 33 of the sleeve for connection to a test stimulator 34, and about one cm is exposed at the distal tip of the sleeve 32 to deliver test stimulation to tissue. The sleeve 32 is electrically insulated or insulated except at its tip. The needle 30 is also electrically insulated, except at its tip.

The tool system 28 also includes a test stimulator 34 of the type described in U.S. Pat. No. 7,878,981, issued Feb. 1, 2011, entitled "Systems and Methods for Intra-Operative Stimulation," which is incorporated herein by reference. The test stimulator operates to generate stimulation wave pulses of the same type as the implanted pulse generator 18. The test stimulator may be a hand-held, single use, sterile, and disposable device to be used in the sterile field, and includes a battery sized to keep the test stimulator operational for a predetermined time, e.g., at least about seven hours. The test stimulator 34 includes a connector cable 36 to couple the test stimulator 34 to the needle 30. A sterile patch electrode 38 is also included, which is to be placed on the skin of the individual and coupled to the test stimulator 34, to serve as a return path for the stimulation waveforms.

In an exemplary embodiment shown in FIGS. 48 to 51, two electrodes 16 are included with the lead 12, although more or less are possible. In order to determine the most efficient and effective configuration, the physician may tune the electrode array by first applying stimulation to the distal (or proximal) electrode and asking for the patient's response, then the proximal for distal) electrode, again asking for the patient's response, and then both electrodes together as one monopolar electrode, along with again asking for the patient's response. The clinical programmer 52 is capable of configuring the pulse generator 18 to apply stimulation to the electrode(s) 16 in at least the configurations described above.

The tool system 28 also includes a tunneling tool 40 and a companion introducer sleeve 41. The tunneling tool 40 is used to pass the implantable lead 12 subcutaneously from a needle incision site to a pulse generator pocket.

The tunneling tool 40 comprises a stainless steel shaft positioned inside a TEFLON® introducer sleeve 41. The shaft, which may be bendable to allow for physical contours, includes a handle to aid the physician in delivering the tunneling tool to the desired location, and a detachable tip 39 that allows the tunneling tool to cut through tissue.

VI. Test Screening Tools

In the above description, the surgical tool system 28 is used to implant the implant system 10 in a single surgical procedure. Alternatively, a two-stage surgical procedure can be used.

The first stage comprises a screening phase that performs test stimulation using a temporary external pulse generator to evaluate if an individual is a suitable candidate for extended placement of the implantable pulse generator. The first stage can be conducted, e.g., during a nominal two week to two month period. If the patient is a suitable candidate, the second stage can be scheduled, which includes the removal of the external pulse generator, and implantation of the pulse generator 18.

A test screening system 42 (shown in FIG. 23) can be provided to facilitate the two stage procedure, including the implantation of one or more lead/electrodes (not shown as part of the test screening system 42). In one embodiment, the test screening system 42 includes a percutaneous extension cable 44, which is sized and configured to be tunneled subcutaneously from the IPG pocket site to a remote site about 10 cm to about 20 cm medially) where it exits the skin. The length of the percutaneous extension cable can vary depending on the anatomy of the patient. The percutaneous extension cable has a proximal and distal portion. The proximal portion carries a standard female IS-1 receptacle 46 for connection to the industry-standard size plug on the end of the lead 12. The distal portion of the percutaneous extension cable 44 carries a plug 48 that couples, e.g., screws, snaps, pressure fits, to an intermediate external extension cable 88, which itself is coupled to an external pulse generator 35 included with the test screening system 42. An organizer 69 may also be included that can take the form of a daily pill case that includes one or more compartments to hold one or more disposable power sources 68 for the external pulse generator 35. A power source 68 is adapted to provide power for each day or period of a prescribed power source replacement regime.

The test screening system 42 also includes the intermediate external extension cable 88. One end of the external extension cable 88 carries a plug 90 to connect to the external pulse generator 35. The other end of the external extension cable 88 includes a connector 92 to receive the plug 48 of the percutaneous extension cable 44. This end of the external extension cable 88 can also be sized and configured to connect directly to the optional surface patch electrode 38.

In one embodiment, the external pulse generator 35 includes an integral return electrode on its tissue facing side. In an alternative embodiment, the patch return electrode 38 is included, or is otherwise available, to be coupled to the external pulse generator 35.

Figure 24:
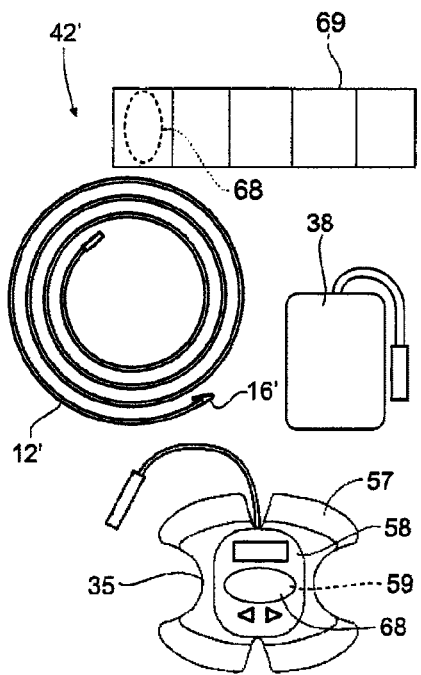
FIG. 24 is a plane view of an alternative test screening system that can used when the system shown in FIG. 13 is implanted in a two stage surgical procedure, the alternative test screening system including one or more leads that are not tunneled to a remote site.
Figure 44:
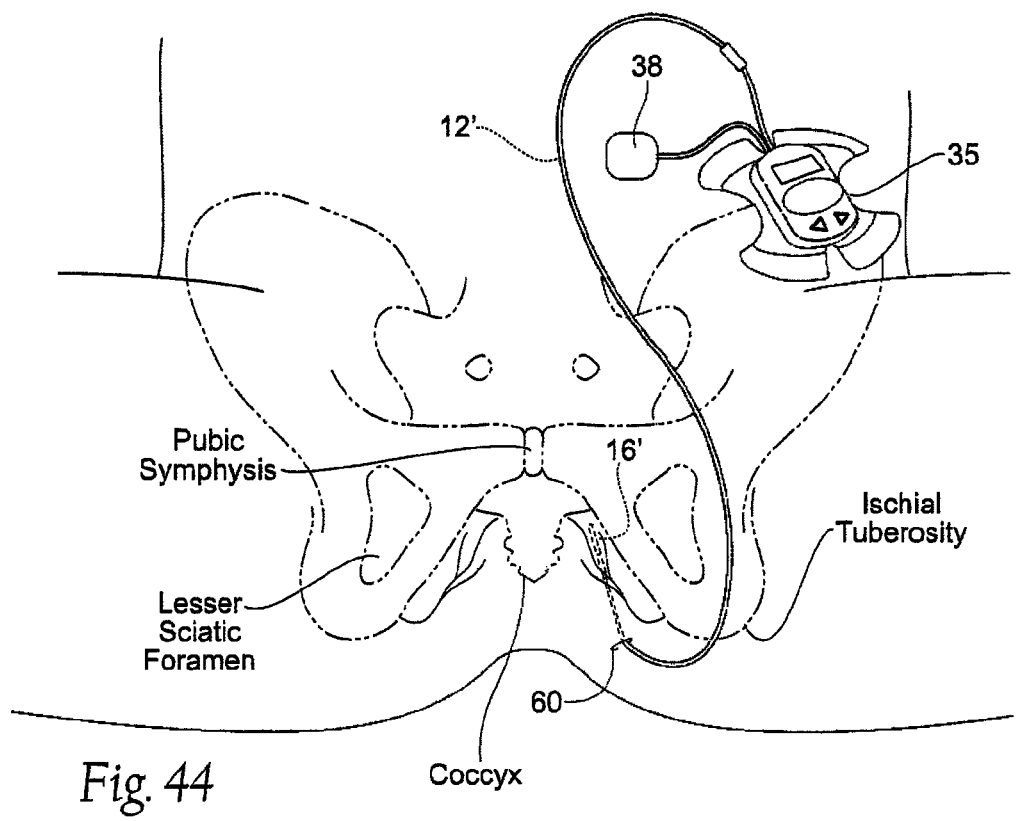

An alternative test screening system 42' may be used and includes a percutaneous EMG style lead 12' and electrode 16' (e.g., fine wire, needle), the external pulse generator 35, and the organizer 69 with one or more disposable power sources 68 (see FIG. 24). Instead of tunneling the lead IT as described below, the lead 12' and electrode 16' are positioned for target nerve stimulation (as described below) and extend through the skin at the insertion site. The lead 12' is then coupled to the external pulse generator 35, as seen in FIG. 44.

VII. Implantation Methodology

Representative surgical tools and techniques will now be described to place the system 10 in a desired location. The use of an IPG connected to one or more leads but located some distance away enables the lead(s) to be placed with a minimally invasive needle-like introducer.

The described novel systems and methods of stimulation are advantageous over pharmaceutical methods because the present invention is specific to its aim of sexual restoration, e.g., generating erection, and does not have the side effects associated with the drugs prescribed for erectile restoration. Furthermore, it does not produce erection by blocking degradation of cGMP, and cGMP tolerance due to consistently raised levels of cGMP has been implicated with the long-term loss of efficacy of oral therapy such as sildenafil (VIAGRA®).

The surgery may have the sole purpose of implanting one or more lead/electrodes for restoration of sexual function, or the surgery may have also been performed for another purpose, related or unrelated, such as surgery related to prostate, urethra, sphincter, colon, tumor (malignant or benign), fistula, abscess, obstruction, and/or any other pelvic surgery.

The lead 12 and electrode 16 (or more than one lead/electrode) are placed at one or more targeted tissue sites at a target nerve A and/or a target nerve B), and at least one IPG 18 is placed remote from the targeted tissue site. It is this desired placement of at least one lead 12 and electrode 16 that makes possible the stimulation of at least one target nerve to provide sexual restoration (e.g., erectile restoration).

These representative surgical implantation methods for implanting at least one lead 12 and electrode 16, and pulse generator 18, of the present invention allows for more rapid placement of these components for the treatment of sexual dysfunctions whereby the electrode 16 is placed so as to achieve stimulation (either unilateral or bilateral) of a target nerve A and/or a target nerve B.

Implanting the lead 12 and electrode 16 near a target nerve can be easily achieved without fluoroscopy, and because of the readily accessible locations, implantation times are reduced from current procedures for existing medical electrical leads stimulating the sacral nerve fibers, in the two-stage procedure described below, the first stage may be completed in approximately 30 to 60 minutes, or less, and the second stage may be completed in approximately less than 30 minutes.

Before implantation, and at the physician's discretion, an oral broad spectrum antibiotic may be given and continued for five days. With the patient in a supine or lateral decubitus position with their back, hips, and legs flexed, the perineum (from at least the anus to the scrotum, or vulva, in females, including the scrotum and penis) is prepped with Betadine (or Hibiclens Solutions for cases of Betadine allergy).

As before generally described, implantation of the implant system 10 shown in FIGS. 7 to 12 can entail a two-stage surgical procedure, including a test screening phase, or a single stage surgical procedure in which the pulse generator is implanted without a screening phase. Each will now be described.

Two-Stage Surgical Procedure

FIGS. 25 to 47 illustrate steps of implanting an implant system 10 in a two-stage surgical procedure. The Figs. show methods of implanting two leads 12A and 12B and one IPG 18 adapted to unilaterally stimulate a target nerve A (e.g., the cavernous nerve), and a target nerve B (e.g., the pudendal nerve). The procedure would be repeated for additional leads to be implanted on, in, or near one or more target nerves for bilateral stimulation, and for an additional IPG to be implanted at a desired remote site.

The first stage (test screening stage) installs one or more leads and electrode arrays and connects the lead to a temporary external pulse generator 35. If the use of the external pulse generator 35 achieves the desired results, an implantable pulse generator 18 is implanted in a second stage.

a.) The First Stage: Test Screening Phase

The patient may undergo monitored anesthesia care (MAC); which is a planned procedure during which the patient undergoes local anesthesia together with sedation and analgesia. During MAC, the patient is sedated and amnestic but always remains responsive when stimulated to do so. Local anesthesia—e.g., 1% Lidocaine (2-5 ccs) or equivalent—may be injected prior to making the anticipated needle incision site 60.

Locating the Lead/Electrode For Target Nerve A Stimulation

Figure 25:
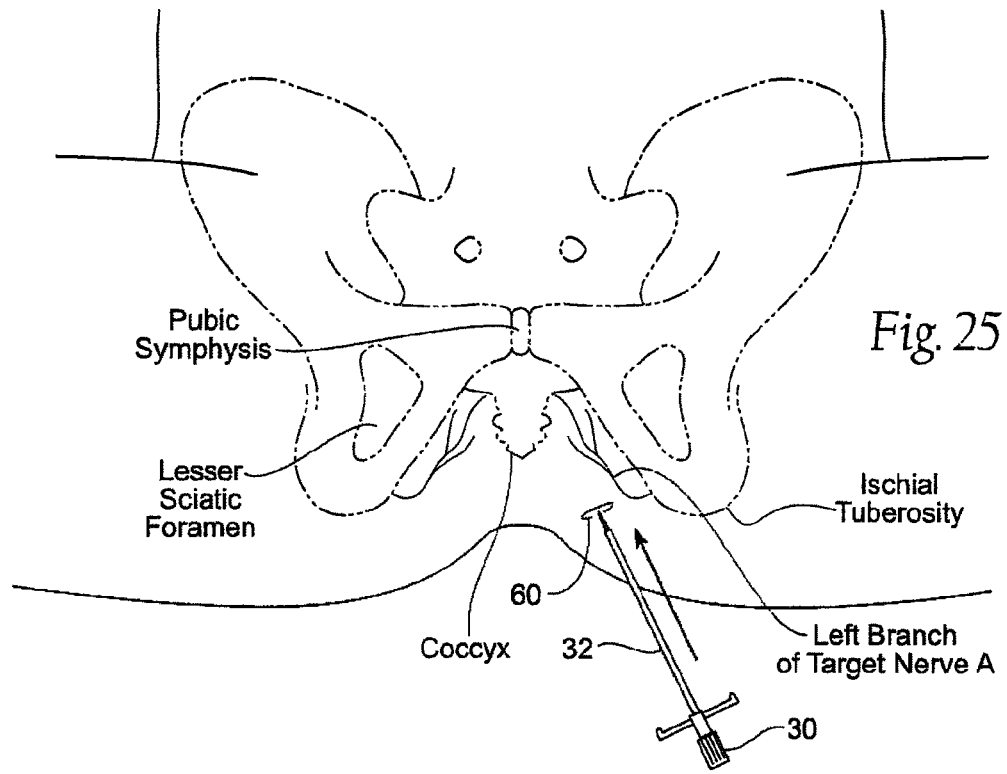
FIGS. 25 to 47 illustrate exemplary steps of implanting a sexual restoration system in a two-stage surgical procedure, such as those shown in FIGS. 7 through 12.
Figure 26:
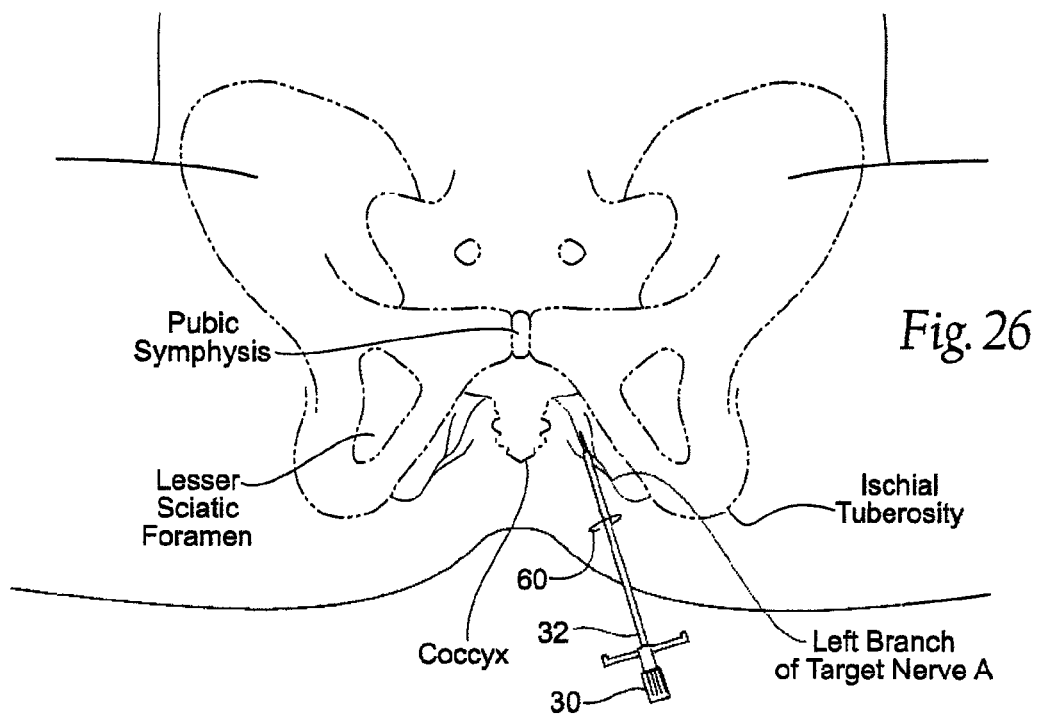
Figure 27:
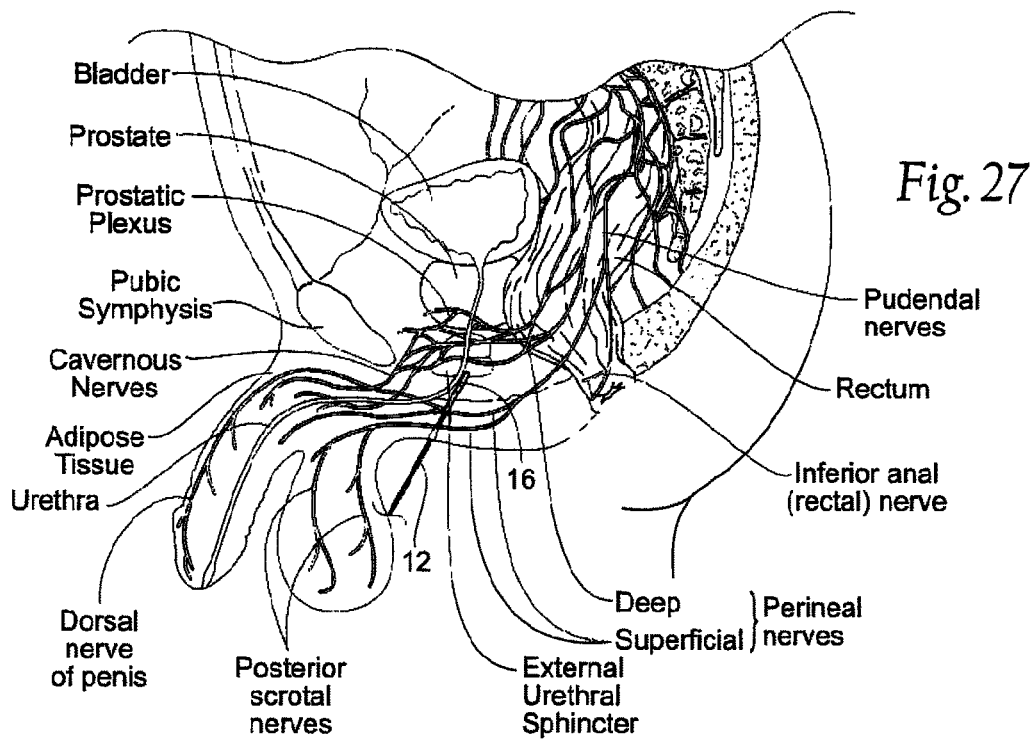
Figure 28:
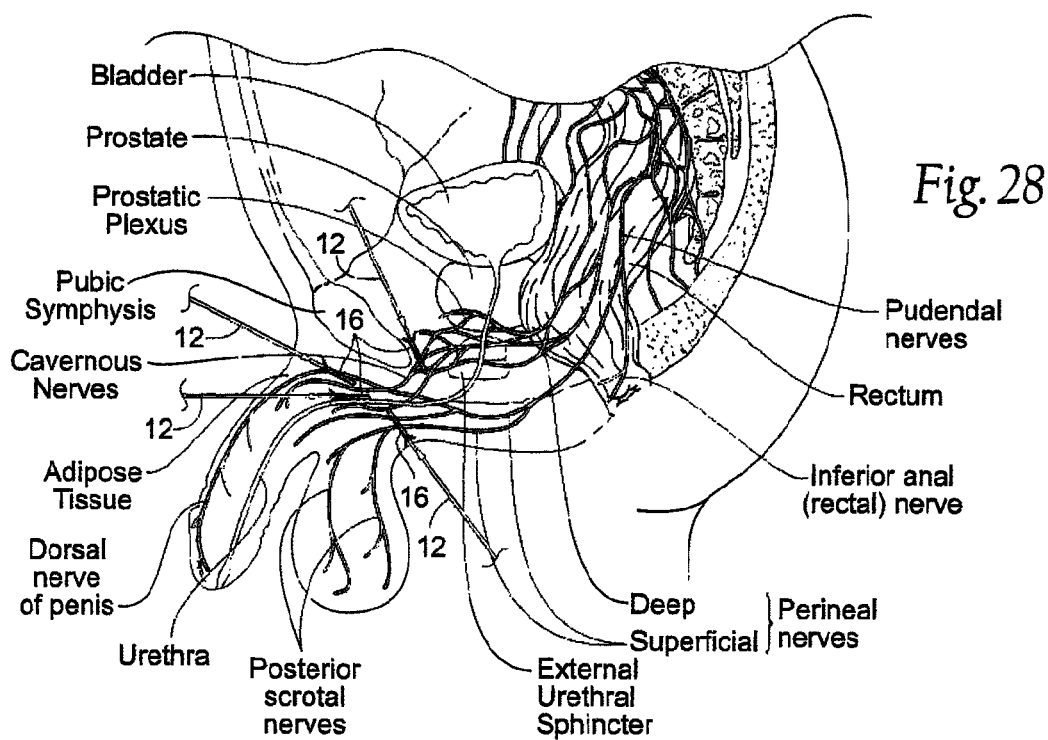

For a target nerve A lead implantation, the site for the needle puncture 60 may be located approximately zero cm to about 6 cm lateral and approximately zero cm to about 6 cm anterior or posterior to the midpoint of a line defined between the posterior superior iliac spine and the ischical tuberosity. Once local anesthesia is established, and as shown in FIGS. 25 and 26, the needle 30 and sleeve 32 may be advanced (the sleeve 32 being pre-loaded over the needle 30) toward target nerve A through the skin into the anesthetized site 60 to a depth of about 0.1-30 cm, or about 1-10 cm (preferred), or 2-7 cm (most preferred) necessary to reach the target site between the urethra and the rectum or between the midline and the ischial tuberosity or between the coccyx and the pubic symphysis. FIG. 27 shows the lead 12 and electrode 16 positioned at a target site to stimulate a target nerve A. It is to be appreciated that the insertion site, the angle of insertion, the approximate insertion depths, and the target nerve desired may vary depending on the particular anatomy of the patient (especially body mass). It is also to be appreciated that additional sites are possible for access to the target nerve A, and positioning of the lead 12 and electrode 16, as can be seen in FIG. 28.

Locating the Lead/Electrode For Target Nerve B Stimulation

Figure 29:
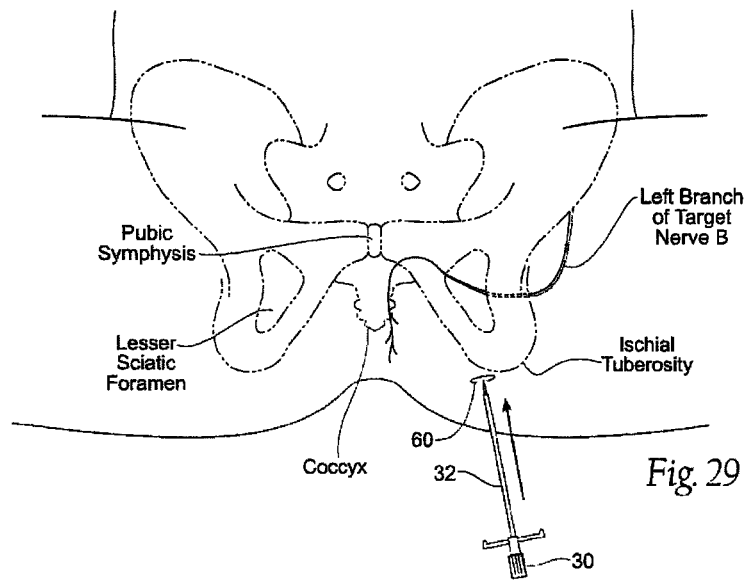
Figure 30:
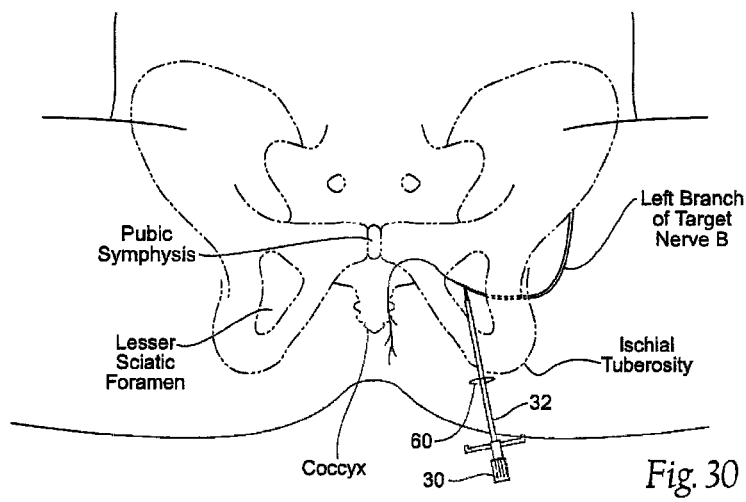
Figure 31:
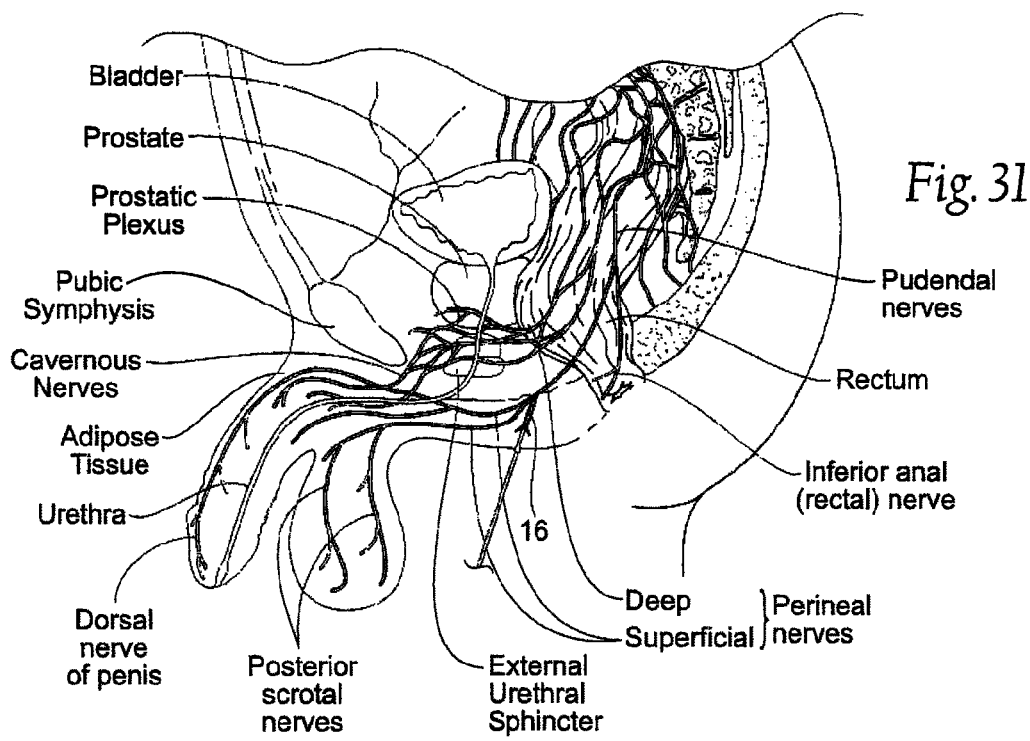
Figure 32:
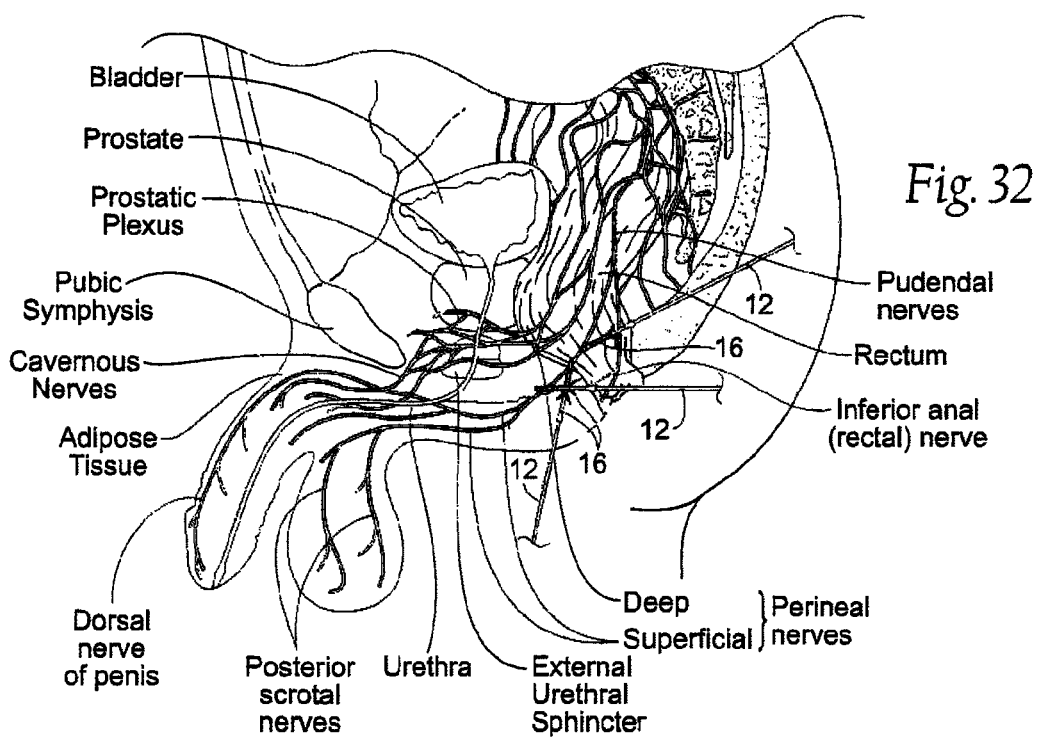

For a target nerve B lead implantation, the site for the needle puncture 60 may be located approximately zero cm to about 6 cm lateral and approximately zero cm to about 6 cm anterior or posterior to the midpoint of a line defined between the posterior superior iliac spine and the ischical tuberosity. As previously described for target nerve A, once local anesthesia is established, and as shown in FIGS. 29 and 30, the needle 30 and sleeve 32 may be advanced (the sleeve 32 being pre-loaded over the needle 30) toward target nerve B through the skin into the anesthetized site 60 to a depth of about 0.1-30 cm, or about 0.5-15 cm (preferred), or 1-6 cm (most preferred) necessary to reach the target site between the midline and the ischial tuberosity or between the coccyx and the pubic symphysis or lateral to the penis/scrotum and rostral to the perineum or in the region of the buttocks. FIG. 31 shows the lead 12 and electrode 16 positioned at a target site to stimulate a target nerve B. It is to be appreciated that the insertion site, the angle of insertion, the approximate insertion depths, and the target nerve desired may vary depending on the particular anatomy of the patient (especially body mass). It is also to be appreciated that additional sites are possible for access to the target nerve B, and positioning of the lead 12 and electrode 16, as can be seen in FIG. 32.

Figure 33:
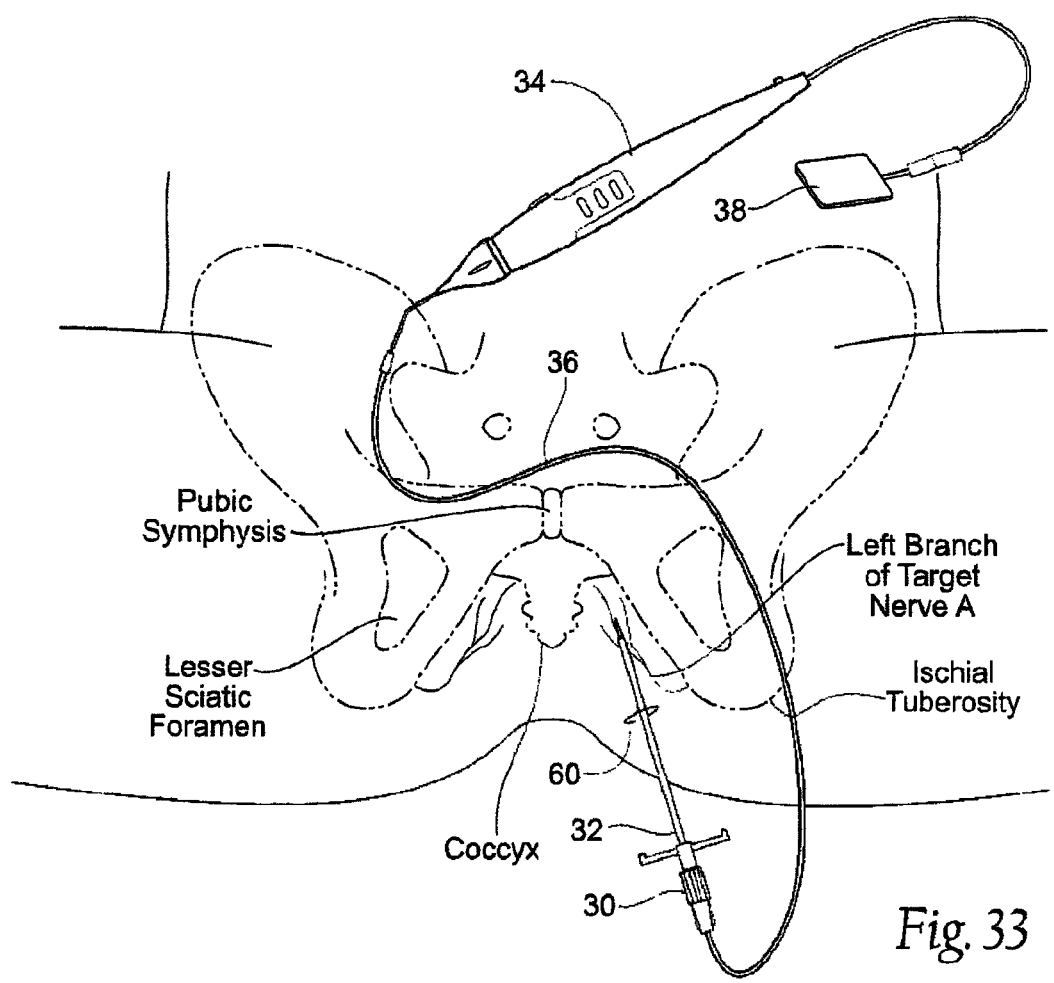

The physician may use one hand to guide the needle 30 and the other hand to stabilize the surrounding tissue. As FIG. 33 shows, once the needle 30 is positioned for target nerve A stimulation, it is coupled to the test stimulator 34 (via the cable 36), to apply stimulation waveforms through the needle tip concurrent with positioning of the needle 30. A patch electrode 38 placed on the skin near the hip of the individual is also coupled to the test stimulator 34 to serve as a return path for the stimulation waveforms.

The test stimulator 34 will be used by the physician in the sterile field. The physician slowly turns up the stimulus on the test stimulator 34 and asks the patient a number of questions to elicit feedback on what they feel and where they feel the stimulation sensations. Proper placement may be confirmed by any of a variety of indications including patient sensation; transduction and/or measurement of one or more physiological event(s) or property(ies), such as electromyogram (EMG), local or systemic blood pressure (venous and/or arterial), pressure in related tissues or structures the corpus cavernosum and/or corpus spongiosum), genital diameter, girth, length, rigidity, engorgement, temperature, and/or color; or visible movement of related organ(s) such as the penis, scrotum, perineal muscle, perineal skin, and/or anal sphincter, (or clitoris for women). The physician monitors any or all of the above indications in concert with applying stimulation waveforms through the needle tip, penetrating and withdrawing the needle 30 and sleeve 32 as necessary in a minimally invasive way, until a subcutaneous location where optimal intended stimulation results are realized. Once this location is found, the test stimulator 34 is disconnected from the needle 30 and the needle is withdrawn from the sleeve 32. These same procedures may also be used for a target nerve B.

Implanting the Lead/Electrode

Figure 34:
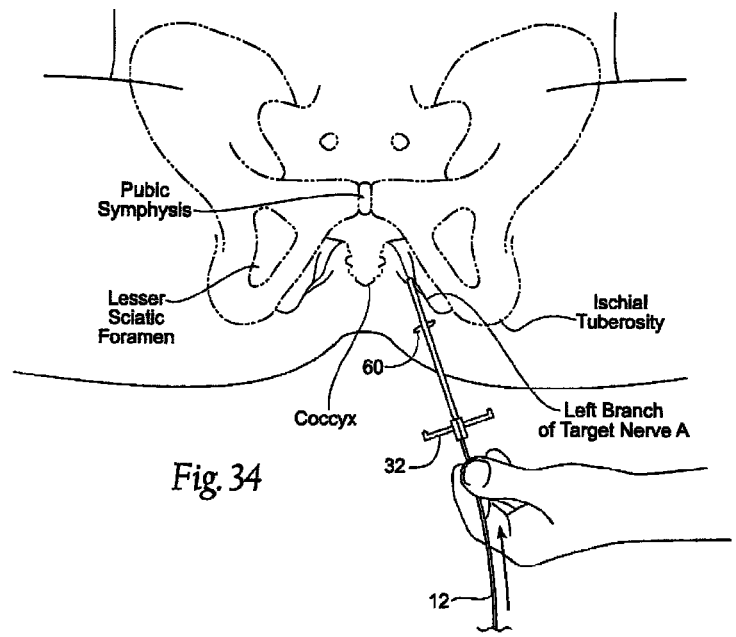
Figure 35:
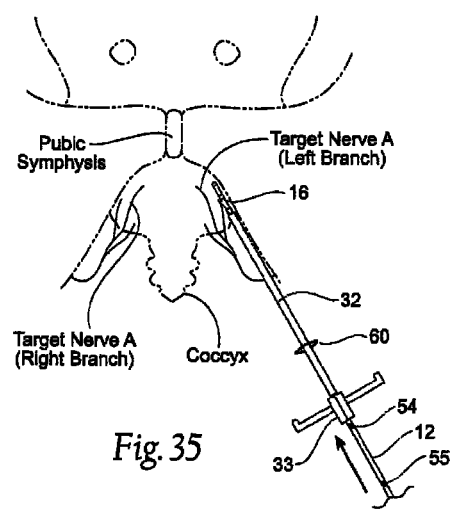
Figure 36:
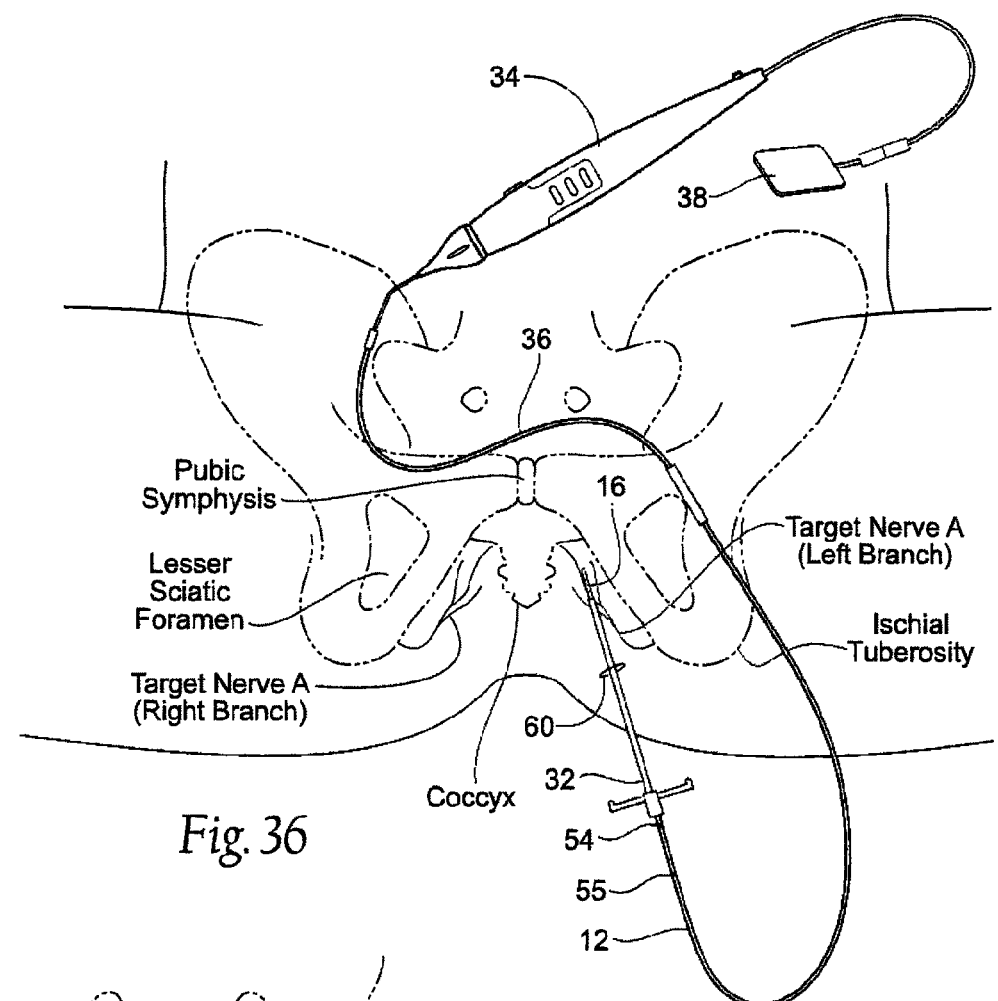

As FIGS. 34 and 35 show, the lead 12, electrode-first, is passed through the sleeve 32. Desirably, a guide wire 94 may be preloaded into a lumen 13 in the lead 12 to provide temporary stiffening during insertion. As FIG. 35 shows, the lead is inserted into the sleeve 32 until a first visual marker 54 on the distal portion of lead 12 indicates that the electrode 16 has been exposed out of the distal end of the sleeve (without exposing tines 76, if used). The lead 12 is now coupled to the test stimulator 34 (via the cable 36), to again apply stimulation waveforms through the electrode 16 concurrent with positioning of the electrode (see FIG. 36). Again, the physician slowly adjusts the stimulation via the test stimulator 34 and asks for the patient feedback of sensation. Based on the patient feedback and/or indications as described above, the physician repositions the lead/electrode if necessary.

Once the optimal location is found, the physician removes the cable 36 from the lead 12, and applies pressure on the skin over top where the electrode 16 is positioned. The guide wire 94 may be withdrawn. This applied pressure helps to secure the lead in place while the sleeve 32 is being removed.

Figure 37:
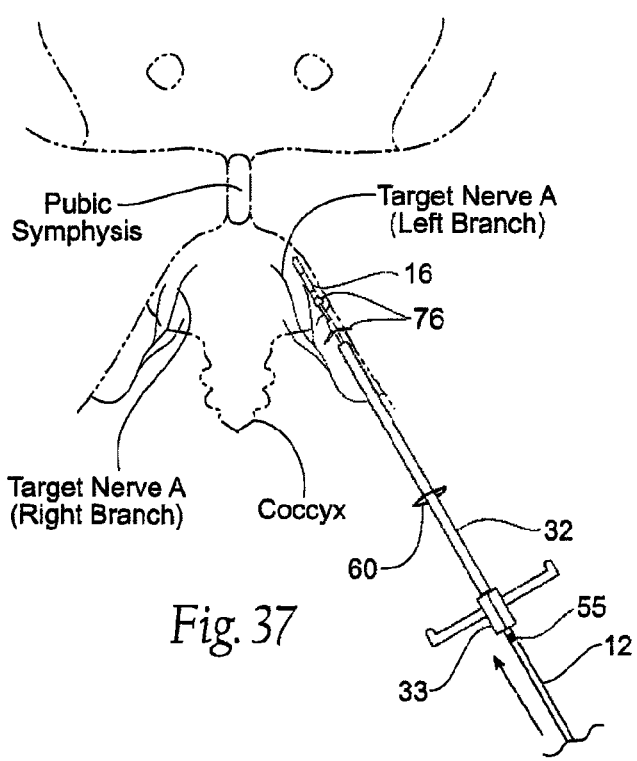
Figure 38:
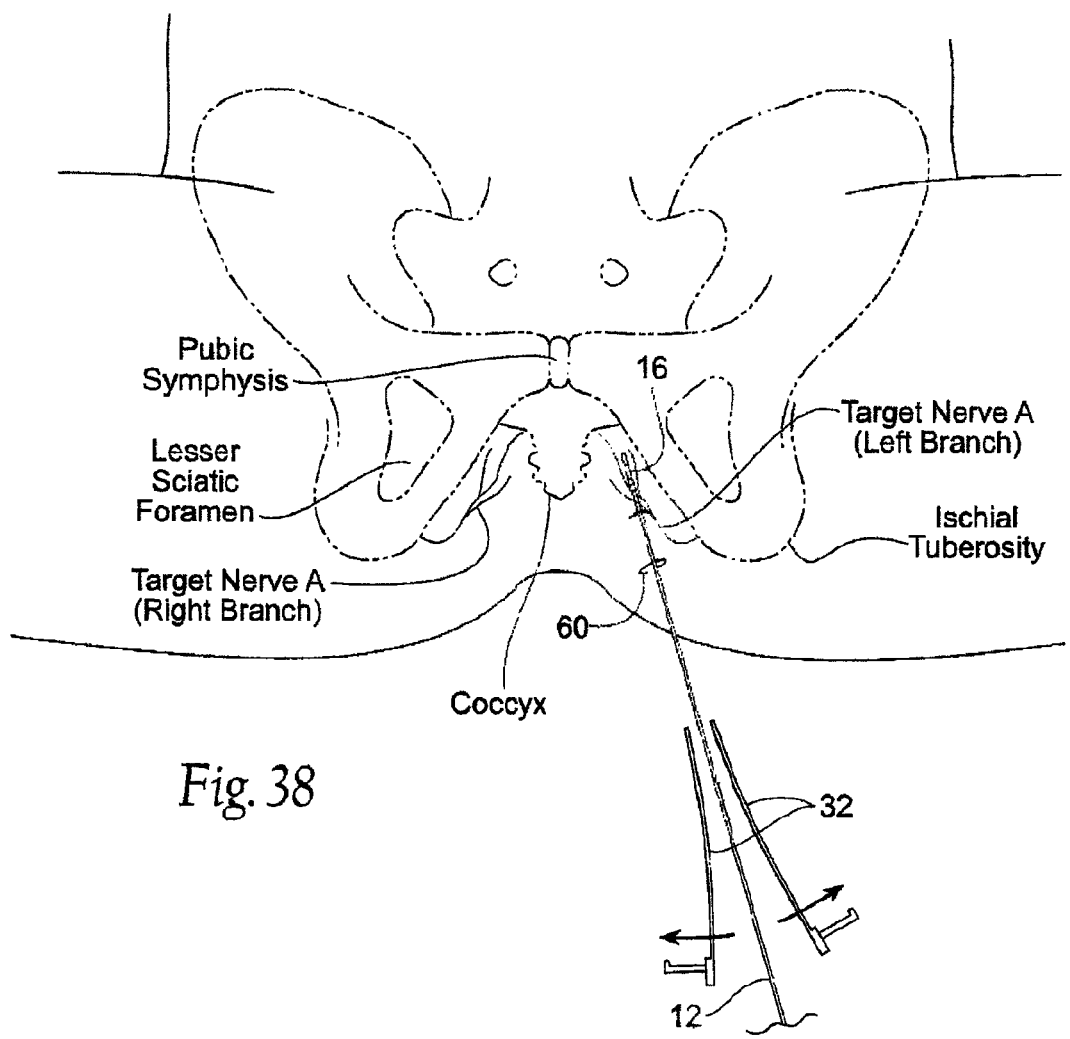

As FIG. 37 shows, the introducing sleeve 32 is withdrawn at least until the second visual lead marker 55 is aligned with the hub 33 on the sleeve. If the lead 12 includes tines 76, the second visual lead marker 55 indicates that the tines 76 on the lead 12 have been deployed, which fixes the location of the electrode 16 in the tissue region. With the physician applying pressure, the sleeve 32 can now be pulled back out of the body. Once the introducing sleeve 32 is completely out of the body and toward the proximal end of the lead 12, the physician separates or peels apart the sleeve 32 into two pieces, as shown in FIG. 38, allowing the sleeve 32 to be removed from the lead.

Optionally, the test stimulator 34 may again be coupled to the lead 12 via the cable 36 to apply stimulation pulses through the electrode 16, to confirm that the electrode 16 resides in the location previously found.

If the alternative lead 12' and electrode 16' are used, the steps as described above would also be used.

Tunneling the Lead and Percutaneous Extension Cable

The physician makes use of the tunneling tool 40 to tunnel the lead 12 and percutaneous extension cable 44 to the desired location(s).

Having implanted one or more leads/electrodes, a subcutaneous tunnel is formed for connecting the lead 12/electrode 16 to the percutaneous extension cable 44. Next, the tunneling tool 40 with sharp tip 39 and sleeve 41 is introduced through the needle incision site 60 (see FIG. 39) and pushed toward the pulse generator pocket site 56. Once the tip 39 of the tunneling tool 40 is in a desired position (identified by the physician through sight and feel), a pocket incision 64 is made for forming the subcutaneous pocket 56 for the pulse generator (to be formed in the second stage), followed by passing the tip 39 of the tunneling tool 40 through the newly formed incision 64.

Figure 40:
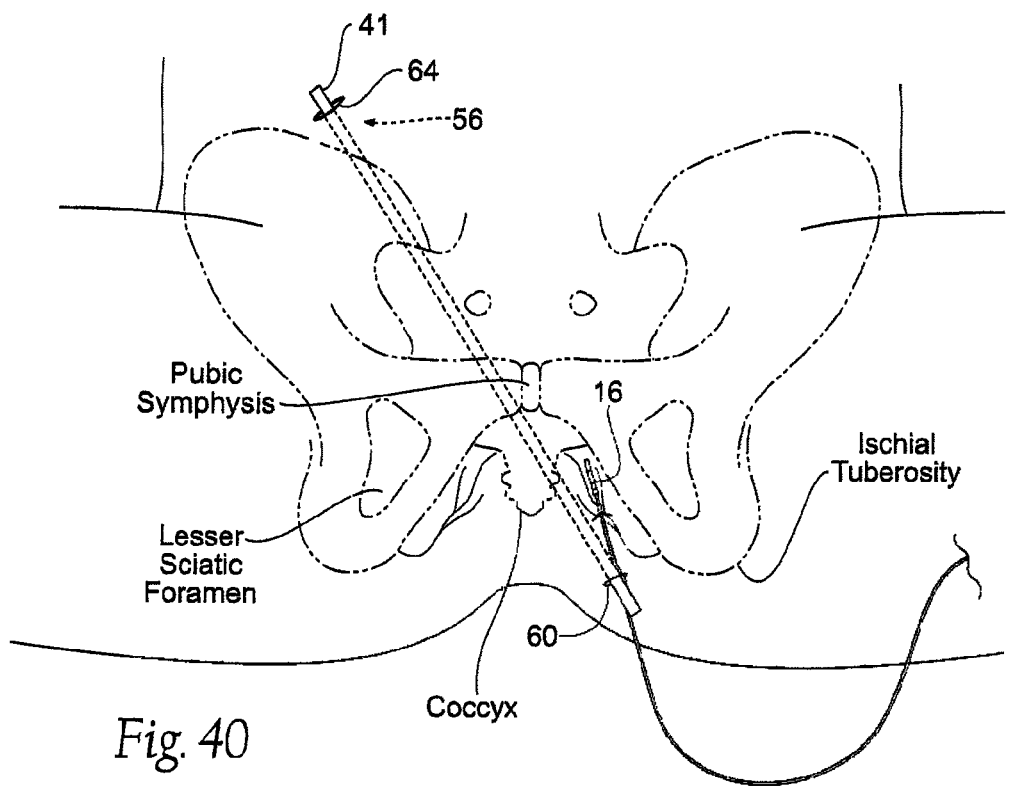
Figure 41:
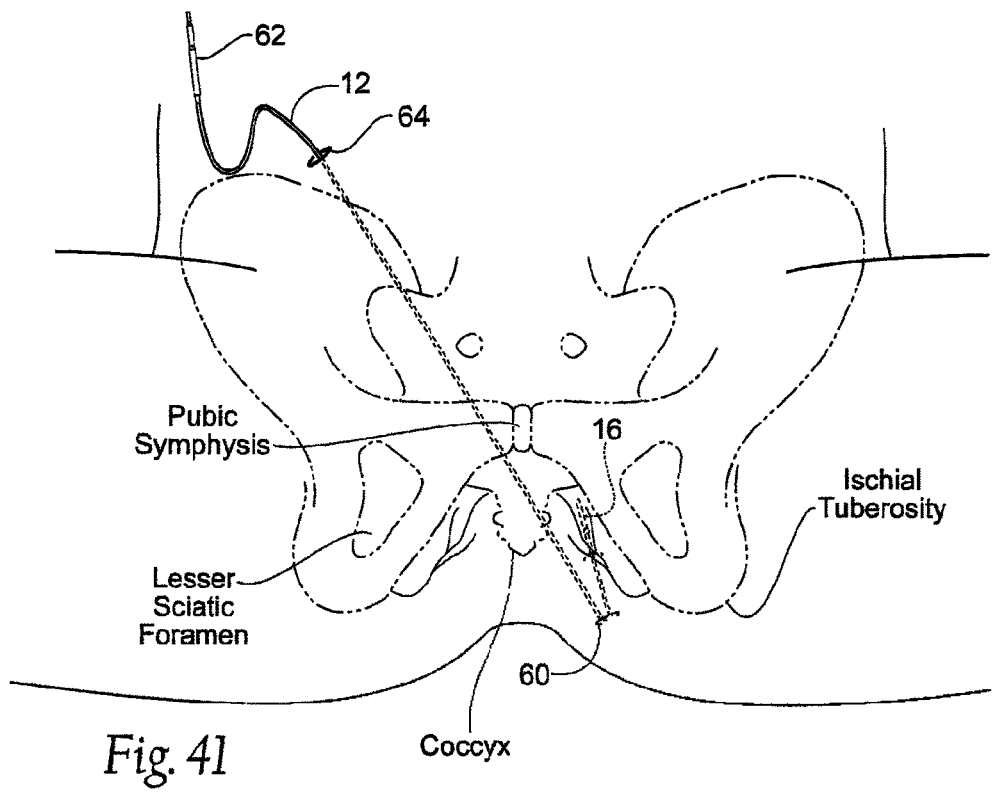
Figure 42:
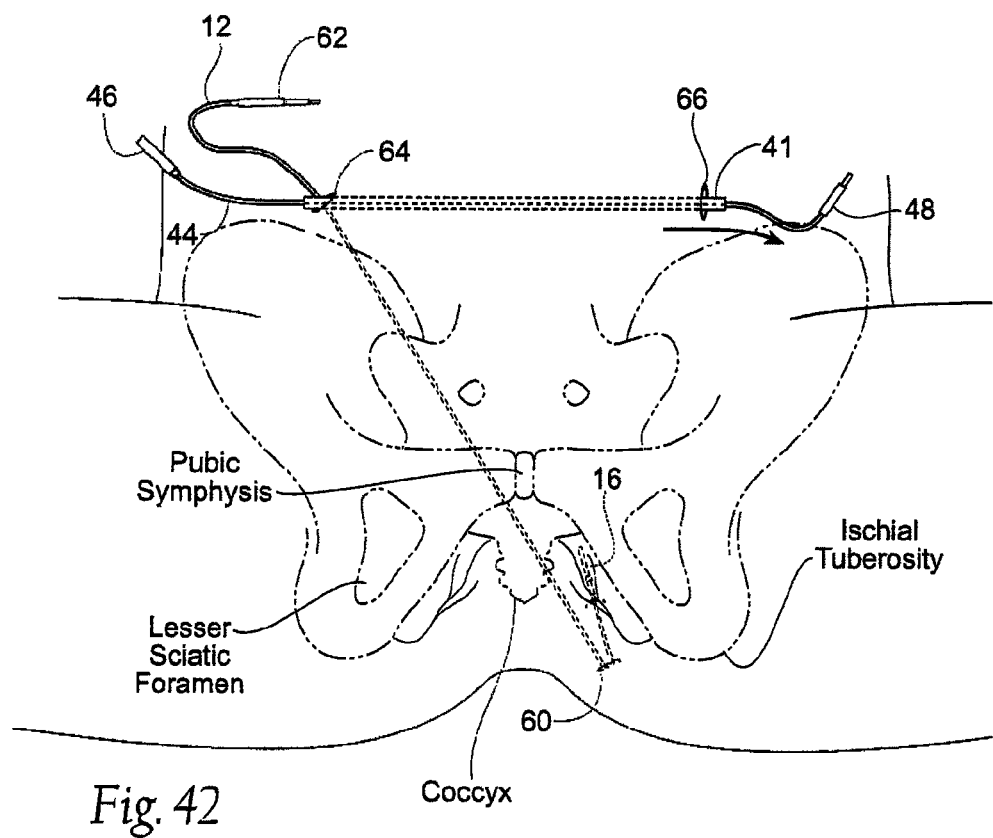

Removal of the tunneling tool 40 leaves the sleeve 41 in place (see FIG. 40), and allows the physician to pass the lead 12 from the needle incision site 60 through the sleeve 41 and to the pocket incision site 64, followed by removal of the sleeve (see FIG. 41).

It should also be appreciated that the directions described above and below for the tunneling tool 40 may be reversed, i.e., instead of tunneling from the needle incision site 60 to the pocket incision site 64, the tunneling may be done from the pocket incision site to the needle incision site.

Similar to the procedure described above for tunneling the lead 12, a tunnel is created to extend a percutaneous extension cable 44 from the pocket incision site 64 to a second incision site 66.

Using the tunneling tool 40 of the surgical tool system 28, the physician subcutaneously creates a tunnel to a suitable exit site, which is desirably remote from the site where the pocket for the implanted pulse generator is to be created in the second phase. The tunneling tool 40 is removed, leaving the sleeve 41 in place. The percutaneous extension cable 44 is then slid through the sleeve 41 and the sleeve is removed (see FIG. 42).

A short length of the percutaneous extension cable 44 that carries the plug 48 extends outside the exit site, for coupling the electrode 16 to the external pulse generator 35 via the intermediate external extension cable 88. The return patch electrode 38 (if used) is also coupled to the external pulse generator 35.

In this configuration, should infection occur in the region where the percutaneous extension cable 44 extends from the skin (second incision site 66), the infection occurs away from the region where the pocket 56 for the implanted pulse generator 18 is to be formed (i.e., at the pocket incision site 64). The pocket incision site 64 and the lead tunnel all the way to the electrode 16 are thereby shielded from channel infection during the first stage, in anticipation of forming a sterile pocket 56 for the implantable generator in the second stage.

Connecting the Lead to the External Pulse Generator

Figure 43:
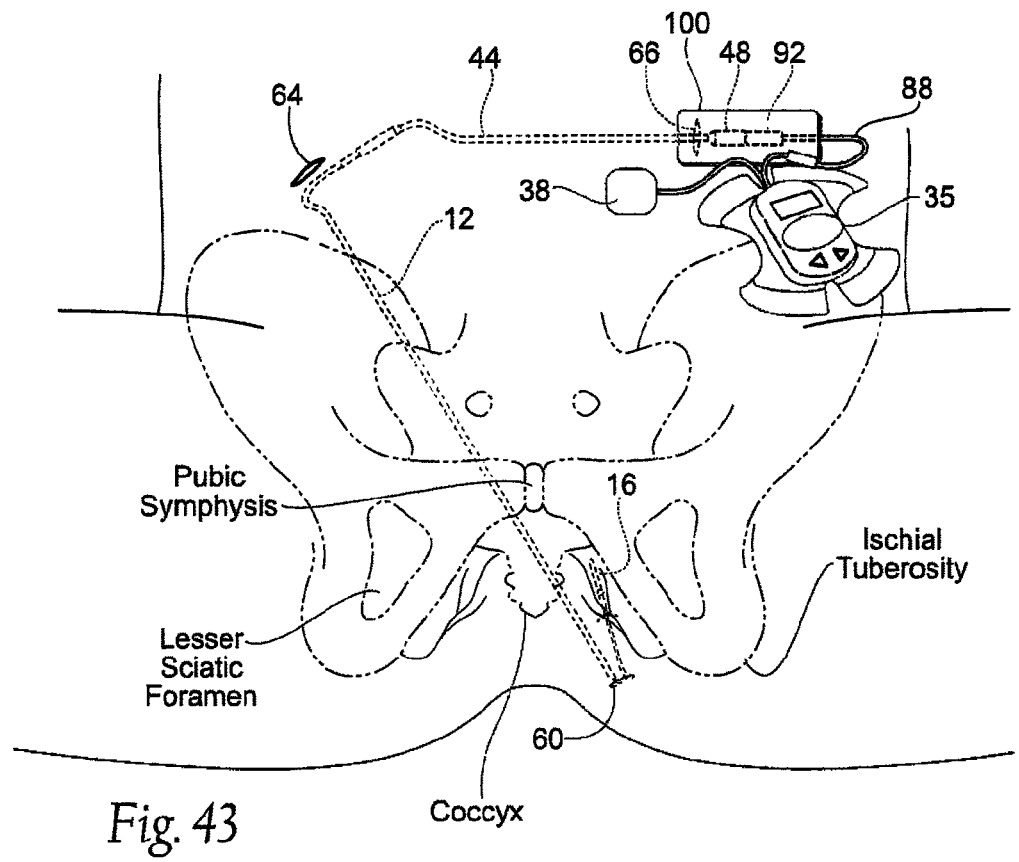

Once the plug 48 of the percutaneous extension cable 44 extends out of the second incision 66, the plug 48 is connected to the external extension cable 88 (as FIG. 43 shows). The connection is then secured externally to the skin with a piece of TEGADERM.™ dressing or sterile tape 100, for example, which may also cover the incision site 66. Additional pieces may be used as necessary. The remainder of the percutaneous cable 44 is located under the skin and is free of exposure to outside contamination. The sterile tape 100 covering the exit site and the re-growth of tissue maintains this sterile barrier.

At the physician's discretion, some or all of the wound sites may be irrigated with irrigation solutions and dosed using DERMABOND™ glue, STERI-STRIP™ material, or stitches of 4-0 VICRYL™, for example.

The individual patient wears the external pulse generator 35 and return patch electrode 38 (if used) for the prescribed test period. The external pulse generator 35 supplies the prescribed stimulation regime. If an improvement in sexual function is achieved, the second phase is warranted. In the second phase, the percutaneous extension cable 44 is removed and discarded, and one or more implantable pulse generators are connected to the one or more leads 12 and installed in a pocket(s) remote from the electrodes 16 in the manner previously described.

For this first stage, an external pulse generator 35 can be used of the type described in U.S. Pat. No. 7,120,499, issued Oct. 10, 2006, entitled "Portable Percutaneous Assemblies, Systems, and Methods for Providing Highly Selective Functional or Therapeutic Neurostimulation," which is incorporated herein by reference. Optionally, an external pulse generator 35 can be used of the type described in co-pending U.S. patent application Ser. No. 11/595,556, filed Nov. 10, 2006, entitled "Portable Assemblies, Systems, and Methods for Providing Functional or Therapeutic Neurostimulation," which is also incorporated herein by reference.

Figure 23:
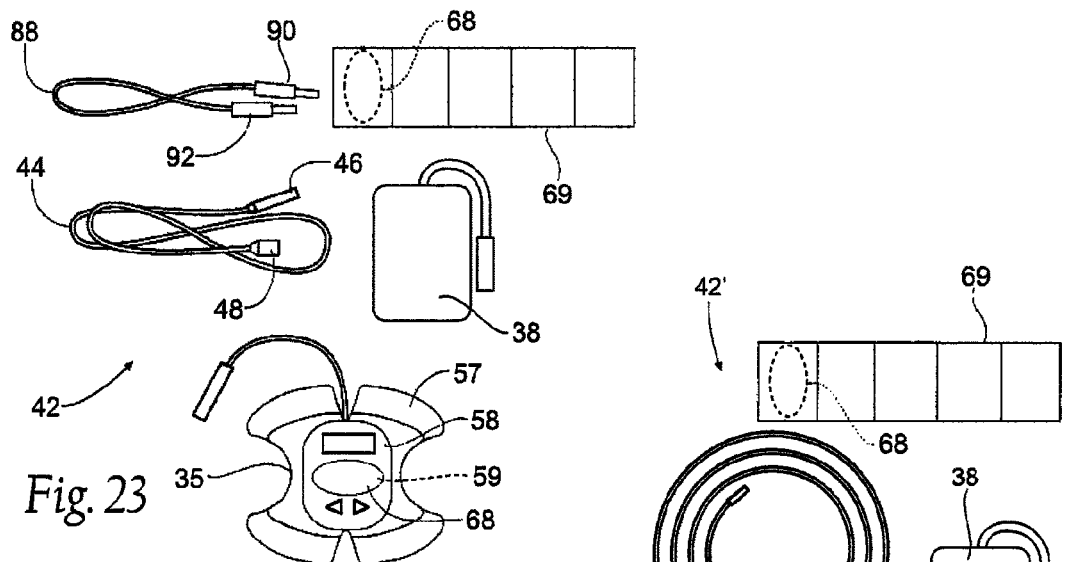
FIG. 23 is a plane view of test screening system that can used when the system shown in FIG. 13 is implanted in a two stage surgical procedure.

As shown in FIG. 43, the device 35 may be electrically coupled to the percutaneous extension cable 44 through the extension cable 88. Referring to FIG. 23, the external pulse generator 34 comprises a skin-worn patch or carrier 57. The carrier 57 can be readily carried, e.g., by use of a pressure-sensitive adhesive, without discomfort and without affecting body image on, for example, an arm, a leg, or torso of an individual. In place of worn on the skin, the patch or carrier may also be carried by the patient, or secured to clothing, a bed, or to movable devices to allow for patient mobility.

The carrier 57 may include a return electrode on its tissue facing surface, and carries a removable and replaceable electronics pod 58, which generates the desired electrical current patterns. The pod 58 houses microprocessor-based, programmable circuitry that generates stimulus currents, time or sequence stimulation pulses, monitors system status, and logs and monitors usage. The electronics pod 58 may be configured, if desired, to accept wireless RF based commands for both wireless programming and wireless patient control.

The electronics pod 58 also includes an electrode connection region (not shown), to physically and electrically couple the lead 12 to the circuitry of the electronics pod. The electronics pod 58 further includes a power input bay 59, to receive a small, lightweight, disposable power source 68, which can be released and replaced as needed. The power source 68 provides power to the electronics pod 58. An organizer 69 may also be included that can take the form of a daily pill case that includes one or more compartments to hold one or more disposable power sources 68.

It is contemplated that, in a typical application for the external pulse generator 35 in the test screening phase, an individual will be instructed to remove and discard a used power source 68 (e.g., after each erectile restoration application, or as necessary), replacing it with a fresh power source. This arrangement simplifies meeting the power demands of the electronics pod 58.

As previously described, the external pulse generator is coupled to the exposed plug 48 of the percutaneous extension cable through the external extension cable 88, as FIG. 43 shows. Optionally, a return patch electrode 38 may be placed on the skin and likewise coupled to the external pulse generator 35. The individual wears the external pulse generator 35 (e.g., in a belt holster or taped to the skin) and return patch electrode 38 (on the skin) for the prescribed test period. The external pulse generator 35 supplies the prescribed stimulation regime. If erectile function is achieved during the test phase, the second phase of the surgical procedure is scheduled to proceed.

b) Alternative First Stage

In an alternative first stage procedure, the lead 12 and electrode 16 comprise a percutaneous EMG style lead 12 and electrode 16' (e.g., fine wire, needle). Instead of tunneling the lead 12' as described above, the lead 12' and electrode 16' are positioned for target nerve stimulation as described above and extend through the skin at the insertion site 60. The lead 12' is then coupled to the external pulse generator 35, as seen in FIG. 44. Optionally, a return patch electrode 38 may be placed on the skin and likewise coupled to the external pulse generator 35.

As previously described, the individual wears the external pulse generator 35 for the prescribed test period. The external pulse generator 35 supplies the prescribed stimulation regime. If erectile function is achieved during the test phase, the second phase of the surgical procedure is scheduled to proceed.

The second phase would include the removal of the percutaneous lead 12 and electrode 16', placing the lead 12 and electrode 16, and tunneling the lead 12 to the pulse generator pocket site 56, as described above. The percutaneous extension cable 44 would not be used in this alternative first stage.

c) The Second Stage: Removing the Percutaneous Extension Cable and Implanting the Pulse Generator The same preoperative antibiotics and skin prep as previously described may be performed, again at the physician's discretion. In the second stage, the external pulse generator 35, return patch electrode 38 (if used), and external extension cable 88 (if used) are disconnected from the percutaneous extension cable 44 (if used), and may be discarded. Under MAC and/or local anesthesia, the incision 64 is reopened. The connection between the percutaneous extension cable 44 and lead 12 is removed from the pocket incision 64 and disconnected.

Forming the Pulse Generator Pocket

Figure 46:
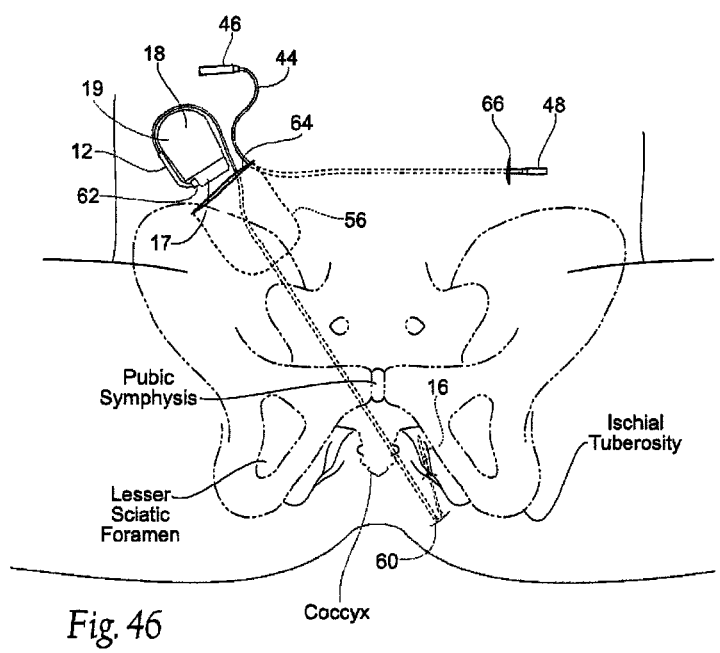

The pocket incision 64 may need to be enlarged to form a subcutaneous pocket 56 to accept the pulse generator 18. The incision 64 is made large enough to accept the index or dissecting finger of the implant physician. As FIG. 46 shows, the subcutaneous pocket 56 is made to accept the pulse generator 18 using blunt dissection techniques of the subcutaneous tissues. The axis of the pocket 56 may follow the direction of the dermatomal skin line and the entrance site of the lead 12/electrode 16.

Connecting the Lead to the Pulse Generator

Prior to removing the pulse generator 18 from its sterile package 110, the clinical programmer 52 is used to turn the puke generator on and wirelessly communicate with the pulse generator to confirm proper operation. Once operation of the pulse generator is confirmed, and the lead 12 has been disconnected from the percutaneous extension cable 44, the plug 62 can be connected to the connector 15 on the pulse generator 18. A set screw 86 is provided on the pulse generator 18 to positively secure the plug 62 within the connector 15. The physician inserts the plug 62 into the connector 15, and then, using the torque tool 87 provided, tightens the set screw 23 to secure the lead 12 to the pulse generator 18 (see FIGS. 45 and 46).

If the alternative lead 12' was used in the test screening phase, the lead 12' would be removed from the targeted tissue region by purposefully pulling the lead 12' until it exits the body. The lead 12 would then be positioned for target nerve stimulation, as previously described. The lead would be tunneled, and a pulse generator pocket formed, as previously described. The lead 12 would then be coupled to the pulse generator 18.

Implanting the Pulse Generator

Once the lead 12 has been connected to the pulse generator 18, the lead 12 and pulse generator can be placed into the pocket 56. In one embodiment, the pulse generator 18 is pear or tear-drop shaped with a small Or narrow end 17 and a larger or wider end 19, with the header 14 coupled to the narrow end 17. As FIGS. 46 and 47 show, this geometry allows the narrow end 17 of the pulse generator 18 (including the header 14), to be placed into the skin pocket 56 first, with the wider end 19 being pushed in last.

Either prior to or after placing the pulse generator 18 into the pocket 56, the receptacle 46 on the proximal end of the percutaneous extension cable 44 may be cut off to allow the percutaneous extension cable 44 to be removed by pulling the cable 44 through the second incision 66. The percutaneous extension cable may be discarded.

Figure 16:
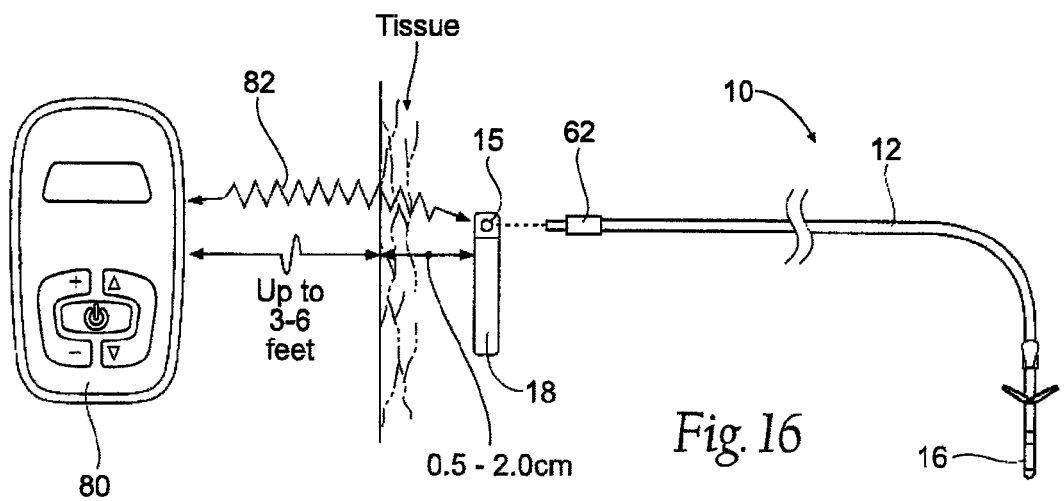
FIG. 16 is a side view showing a representative implant depth of the implantable pulse generator in tissue.
Figure 17:
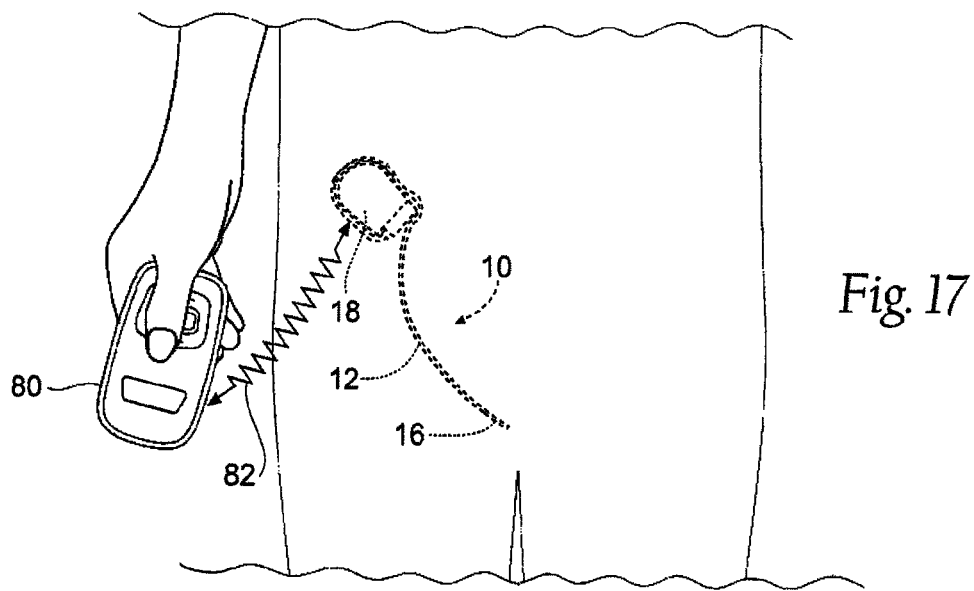
FIG. 17 is an anterior anatomical view of the implant system shown in FIG. 16, and showing the use of a patient controller to operate the system.
Figure 47:
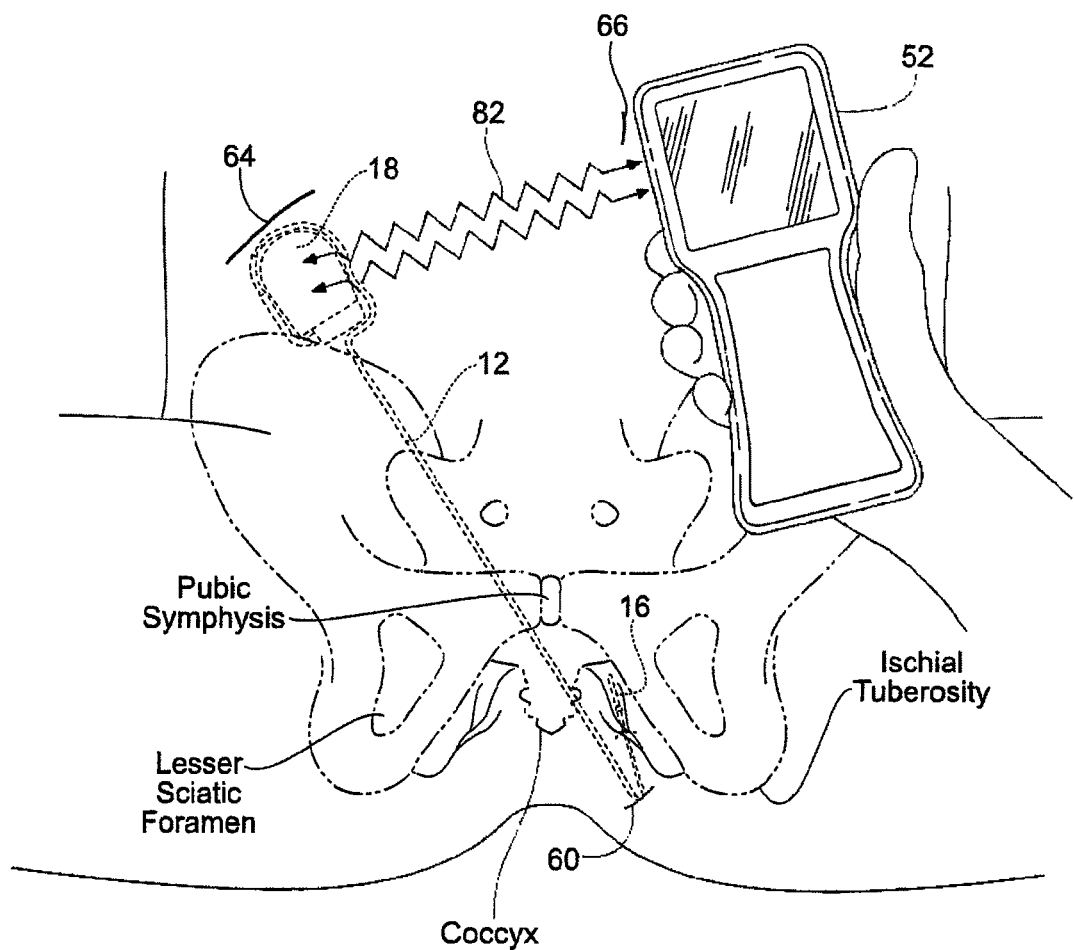

The external fixing surface of the implanted pulse generator 18 is desirably located about 0.5 cm to about 2.0 cm from the external surface of the skin (as can be seen in FIG. 16), and more desirably about 1.0 cm from the external surface of the skin, The cable is oriented with an open loop of cable around the pulse generator (not across the pulse generator) to allow for motion of the abdominal contents without transmitting forces along the cable and lead (see FIGS. 46 and 47). The external facing surface may include etching to help the physician identify which side is the intended external facing surface. The patient may be asked to move, i.e., sit up and lay back down, to be certain that the pulse generator 18 is properly positioned within the pocket 56 and at the desired implant depth.

As can be seen in FIG. 47, the clinical programmer 52 is again used to turn on the pulse generator 18 and to program and/or test the system and/or stimulus response. The clinical programmer would use wireless telemetry and may be located either inside or outside of the surgical field, e.g., up to about three to six feet away from the implanted pulse generator 18.

Once proper pulse generator operation is confirmed, the incision site 64 is closed. At the physician's discretion, the incision site 64 may be irrigated with irrigation solutions (e.g., ½ strength betadine or Hibiclens solution), and closed using DERMABOND™ glue, STERI-STRIP™ material, or stitches of 4-0 VICRYL™, for example. Dressing is desirably applied for about twenty-four hours. The incisions are desirably kept dry for forty-eight hours.

2. Single Stage Surgical Procedure

The figures used to illustrate the steps of implanting the implant system 10 in a two stage surgical procedure will also be used to illustrate the steps of implanting the implant system 110 in a single stage surgical procedure. The single stage surgical procedure eliminates the test screening phase temporary use of the external pulse generator 35 and percutaneous extension cable 44), and in the single surgical procedure implants the pulse generator 18 in the pulse generator pocket 56.

Locating the Lead/Electrode

The same preoperative antibiotics and skin prep as previously described are performed. Under MAC and/or local anesthesia, the electrode 16/lead 12 is located as previously described for the first stage of the two stage procedure, and as shown in FIGS. 25 through 38.

Tunneling the Lead

Figure 39:
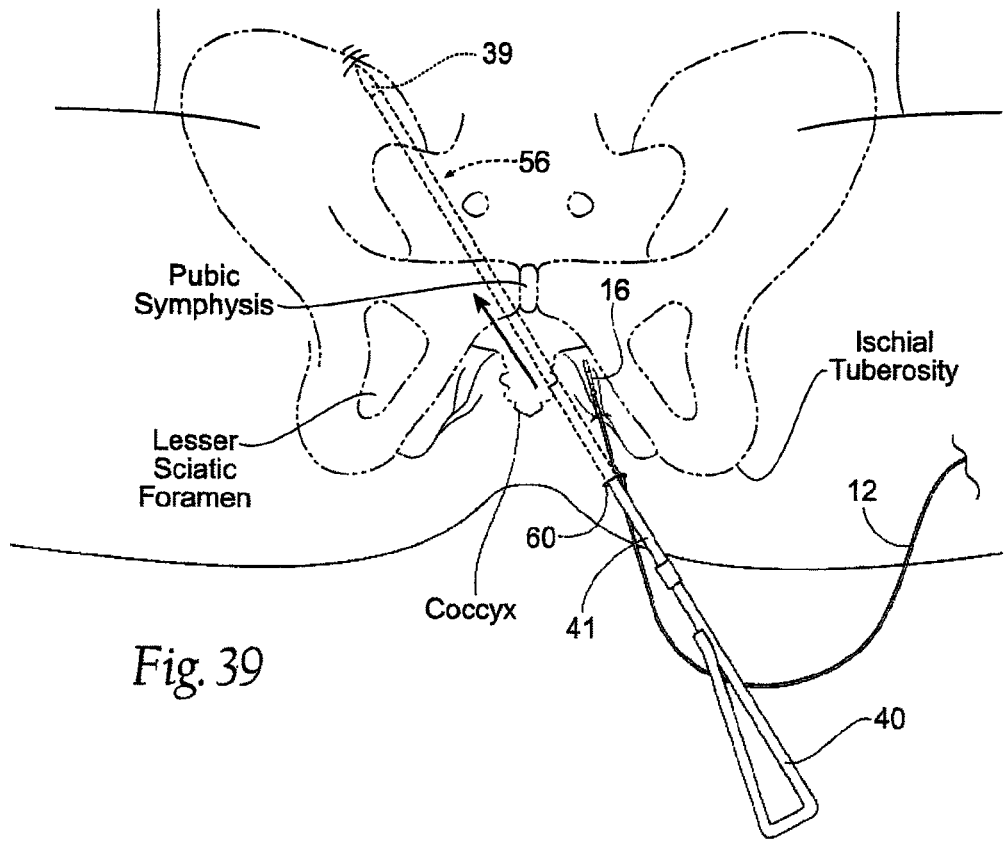

Having implanted the lead/electrode, a subcutaneous tunnel is formed for connecting the lead 12 to the pulse generator 18. The tunneling tool 40 is manipulated by the physician to route the lead 12 subcutaneously to the pocket site 56 where the pulse generator 18 is to be implanted. The lead 12 is tunneled as previously described for the first stage of the two stage procedure, and as shown in FIGS. 39 through 41.

Forming the Pulse Generator Pocket

After placement of the lead 12 as FIG. 41 shows, the pocket incision 64 is enlarged to form a subcutaneous pocket 56 to accept the pulse generator 18 using blunt dissection techniques of the subcutaneous tissues, as previously described for the second stage of the two stage procedure, and as shown in FIG. 46.

Connecting the Lead to the Pulse Generator

Figure 45:
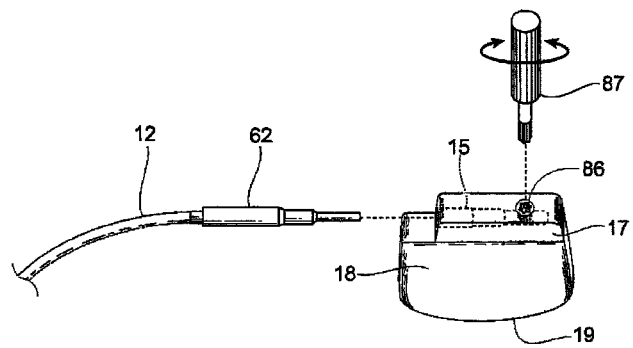

With the pocket 56 formed, and the lead 12 and plug 62 delivered into the procedural field, the lead can now be connected to the pulse generator 18. The lead 12 is connected to the pulse generator 18 as previously described for the second stage of the two stage procedure, and as shown in FIGS. 45 and 46.

Implanting the Pulse Generator

Once the lead 12 has been connected to the pulse generator 18, the lead 12 and pulse generator can be placed into the pocket 56 as previously described for the second stage of the two stage procedure, and as shown in FIGS. 46 and 47.

At the physician's discretion, some or all of the wound sites may be irrigated with irrigation solutions (e.g., ½ strength betadine or Hibiclens solution), and closed using DERMA-BOND™ glue, STERI-STRIP™ material, or stitches of 4-0 VICRYL™, for example. Dressing is desirably applied for about twenty-four hours. The incisions are desirably kept dry for forty-eight hours.

Using the surgical tool system 28, the implant system 10 can be implanted in the manner shown in FIGS. 7 through 12. The steps as described may be repeated as necessary for more than one lead/electrode and/or more than one IPG, to stimulate a target nerve A and/or a target nerve B.

VIII. Features of the Lead and Electrode
  A. Implantation in Pelvic Region

The lead 12 and electrode 16 are sized and configured to be inserted into and to rest in the targeted tissue region in the lower pelvic region without causing pain or discomfort or impact body image. Desirably, the lead 12 and electrode 16 can be inserted using the small (e.g., smaller than 16 gauge) introducer sleeve 32 with minimal tissue trauma. The lead 12 and electrode 16 are formed from a biocompatible and electrochemically suitable material and possess no sharp features that can irritate tissue during extended use. Furthermore, the lead 12 and electrode 16 possess mechanical characteristics including mechanical compliance (flexibility) along their axis (axially), as well as perpendicular to their axis (radially), and unable to transmit torque, to flexibly respond to dynamic stretching, bending, and crushing forces that can be encountered in this body region without damage or breakage, and to accommodate relative movement of the pulse generator coupled to the lead 12 without imposing force or torque to the electrode 16 which tends to dislodge the electrode.

Figure 48:
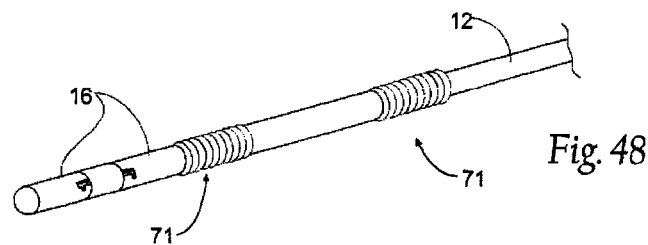
FIG. 48 is a perspective view of one embodiment of the lead and electrode associated with the system shown in FIGS. 7 through 12, including stabilization means.
Figure 49:
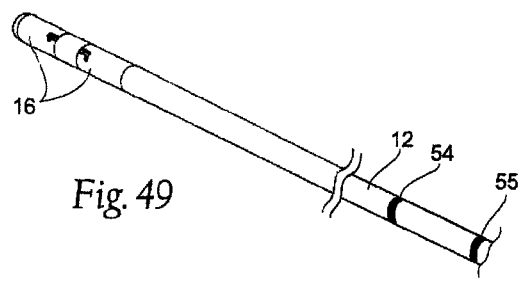
FIG. 49 is a perspective view of an alternative embodiment of the lead and electrode associated with the system shown in FIGS. 7 through 12, without stabilization means or anchoring means.

One embodiment of the lead 12 and electrode 16 may include stabilization means to help stabilize the position of the electrode 16 from migration within or extrusion from the targeted nerve area in response to force conditions normally encountered during periods of extended use. As shown in FIG. 48, the lead 12 includes at least one ribbed portion 71 to help maintain the position of the electrode. FIG. 49 shows the lead 12 without stabilization means or anchoring means.

Figure 50:
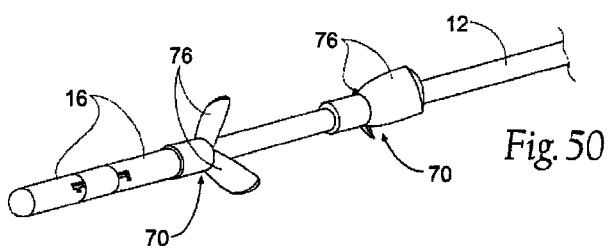
FIGS. 50 and 51 are perspective views of an additional alternative embodiment of the lead and electrode associated with the system shown in FIGS. 7 through 12, the lead including anchoring means.
Figure 51:
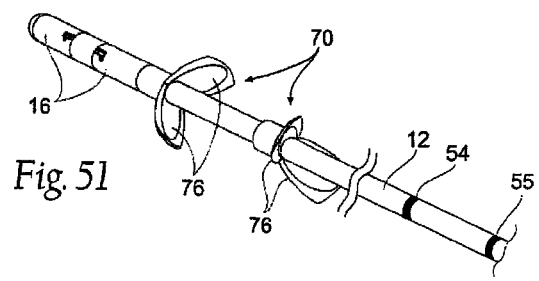

In an alternative embodiment, the lead 12 and electrode 16 may include anchoring means 70 for providing retention strength to resist migration within or extrusion from the targeted tissue region (see FIGS. 50 and 51). In addition, the anchoring means 70 is desirably sized and configured to permit the electrode 16 position to be adjusted easily during insertion, allowing placement at the optimal location where unilateral or bilateral stimulation of a target nerve A and/or a target nerve B occurs. The anchoring means 70 functions to hold the electrode at the implanted location despite the motion of the tissue and small forces transmitted by the lead due to relative motion of the connected pulse generator due to changes in body posture or external forces applied to the abdomen. However, the anchoring means 70 should allow reliable release of the electrode 16 at higher force levels, to permit withdrawal of the implanted electrode 16 by purposeful pulling on the lead 12 at such higher force levels, without breaking or leaving fragments, should removal of the implanted electrode 16 be desired.

It is to be appreciated that stabilization means and/or anchoring means are not a requirement for the present invention.

B. The Lead

Figure 52:
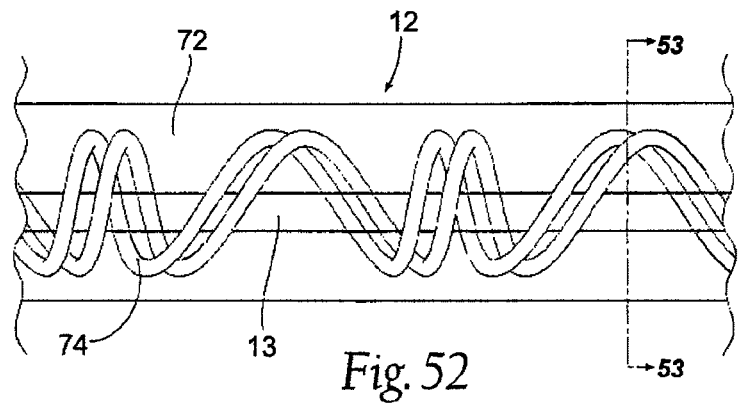
FIG. 52 is a side interior view of a representative embodiment of a lead of the type shown in FIGS. 48 through 51.
Figure 53:
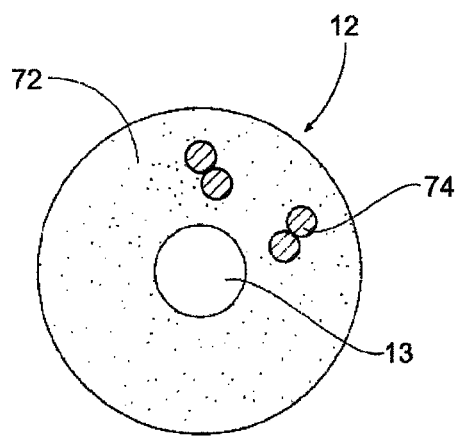
FIG. 53 is an end section view of the lead taken generally along line 53-53 in FIG. 52.
Figure 54:
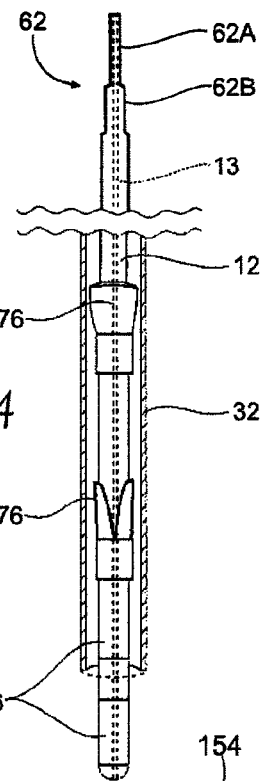
FIG. 54 is an elevation view, in section, of a lead and electrode of the type shown in FIGS. 50 and 51 residing within an introducer sleeve for implantation in a targeted tissue region, the anchoring members being shown retracted within the sheath.

FIGS. 52 through 54 show a representative embodiment of a lead 12 that provide the foregoing features. The implantable lead 12 comprises a molded or extruded component 72, which encapsulates one or more stranded or solid wire elements 74, and includes the connector 62 (shown in FIG. 54). The wire element may be bifilar, and may be constructed of coiled MP35N nickel-cobalt wire or wires that have been coated in polyurethane. In a representative embodiment with two electrically conductive surfaces 16 (as described below), one wire element 74 is coupled to the distal electrode 16 and the pin 62A of the connector 62. A second wire element 74 is coupled to the proximal electrode 16 and the ring 62B on the connector 62. The molded or extruded lead 12 can have an outside diameter ranging between about 0.05 mm to about 5.0 mm, and as small as about one (1) mm, and desirably about 1.9 mm. The lead 12 may also include an inner lumen 13 having a diameter about 0.2 millimeters to about 0.5 millimeters, and desirably about 0.35 millimeters. The lead 12 may be approximately 10 cm to 40 cm in length, although the lead may be shorter or longer, depending on the target nerve to be stimulated and the anatomy of the patient. The lead 12 provides electrical continuity between the connector 62 and the electrode 16.

The coil's pitch can be constant or, as FIG. 52 shows, the coil's pitch can alternate from high to low spacing to allow for flexibility in both compression and tension. The tight pitch will allow for movement in tension, while the open pitch will allow for movement in compression.

A standard IS-1 or similar type connector 62 at the proximal end provides electrical continuity and mechanical attachment to the pulse generator 18. The lead 12 and connector 62 all may include provisions (e.g., lumen 13) for a guidewire that passes through these components and the length of the lead 12 to the conductive electrode 16 at the distal end.

C. The Electrode

The electrode 16 may comprise an array of one or more electrically conductive surfaces. Two conductive surfaces are show in FIGS. 48 through 51, although more or less are possible. The two conductive surfaces can be used in three configurations; i) as one two individual stimulating (cathodic) electrodes in a monopolar configuration using the metal case of the pulse generator 18 as the return (anodic) electrode, or ii) either the distal or proximal conductive surface as a individual stimulating (cathodic) electrode in a monopolar configuration using the metal case of the pulse generator 18 as the return (anodic) electrode, or iii) in bipolar configuration with one electrode functioning as the stimulating (cathodic) electrode and the other as the return (anodic) electrode.

In general, bipolar stimulation is more specific than monopolar stimulation—the area of stimulation is much smaller—which is good if the electrode 16 is close to the target nerve. But if the electrode 16 is farther from the target nerve, then a monopolar configuration could be used because with the pulse generator 18 acting as the return electrode, activation of the nerve is less sensitive to exact placement than with a bipolar configuration.

In use, a physician may first attempt to place the electrode 16 close to the target nerve so that it could be used in a bipolar configuration, but if bipolar stimulation failed to activate the target nerve, then the electrode 16 could be tuned by switching to a monopolar configuration. Two separate conductive surfaces on the electrode array 16 provide an advantage to allow for tuning because if one conductive surface fails to activate the target nerve because it is too far from the nerve, then stimulation with the second conductive surface could be tried, which might be closer to the target nerve. Without the two or more conductive surfaces, a physician would have to reposition the electrode to try to get closer to the target nerve.

The electrode 16, or electrically conductive surface or surfaces, can be formed from PtIr (platinum-iridium) or, alternatively, 316L: stainless steel. Each electrode 16 possess a conductive surface of approximately 10 mm$^2$-20 mm$^2$ and desirably about 16.5 mm$^2$. This surface area provides current densities up to 2 mA/mm$^2$ with per pulse charge densities less than about 0.5 μC/mm$^2$. These dimensions and materials deliver a charge safely within the stimulation levels supplied by the pulse generator 18.

Each conductive surface has an axial length in the range of about three to five millimeters in length and desirably about four millimeters. When two or more conductive surfaces are used, either in the monopolar or bipolar configurations as described, there will be an axial spacing between the conductive surfaces in the range of approximately one to five millimeters, and desirably about two millimeters.

D. The Anchoring Means

In the embodiment shown in FIGS. 50 and 51, the lead is anchored by anchoring means 70 specifically designed to secure the electrode 16 in tissue in electrical proximity to the target nerve, with or without the support of muscle tissue. The anchoring means 70 takes the form of an array of shovel-like paddles or scallops 76 proximal to the proximal-most electrode 16 (although a paddle 76 or paddles could also be proximal to the distal most electrode 16, or could also be distal to the distal most electrode 16). The paddles 76 as shown and described are sized and configured so they will not cut or score the surrounding tissue.

The paddles 76 are desirably present relatively large, generally planar surfaces, and are placed in multiple rows axially along the distal portion of lead 12. The paddles 76 may also be somewhat arcuate as well, or a combination of arcuate and planar surfaces. A row of paddles 76 comprises two paddles 76 spaced 180 degrees apart. The paddles 76 may have an axial spacing between rows of paddles in the range of six to fourteen millimeters, with the most distal row of paddles 76 adjacent to the proximal electrode, and each row may be spaced apart 90 degrees. The paddles 76 are normally biased toward a radially outward condition into tissue. In the radially deployed condition, the paddles have a diameter (fully opened) of about four millimeters to about six millimeters, and desirably about 4.8 millimeters.

The paddles 76 are not stiff, i.e., they are generally pliant, and can be deflected toward a distal direction in response to exerting a pulling force on the lead 12 at a threshold axial force level, which is greater than expected day-to-day axial forces. The paddles 76 are sized and configured to yield during proximal passage through tissue in result to such forces, causing minimal tissue trauma, and without breaking or leaving fragments, despite the possible presence of some degree of tissue in-growth. This feature permits the withdrawal of the implanted electrode 16, if desired, by purposeful pulling on the lead 12 at the higher axial force level.

E. Stimulating and Blocking Electrodes

Known high frequency block configurations commonly use one or more cuff electrode configurations. A first cuff (or set of electrodes) is used to provide the block and another cuff (or set of electrodes) is used to evoke the desired (lower frequency) stimulus.

In one embodiment, the two conductive surfaces show in FIGS. 48 through 51 may be configured as one blocking electrode and one stimulating electrode. This configuration would be advantageous over known frequency blocking configurations because of the ease and reduced trauma of implantation, especially when placing the electrode configuration in the pelvic region near a target nerve A and/or a target nerve B, and that a single lead may be implanted to perform both blocking and stimulating, compared to two leads, one for stimulating and one for blocking. Further, it may be difficult to appropriately place two different leads in the desired region when the target region near a target nerve is small (e.g., on order of 1 cm to 2 cm), thus there may only be space for a single lead and not two leads.

As shown and described, there will be an axial spacing between the conductive surfaces in the range of approximately one to five millimeters, and desirably about two millimeters. When the electrodes are used in a stimulating and blocking configuration, the distance between the stimulating electrode and the blocking electrode may need to be increased.

Figure 55:
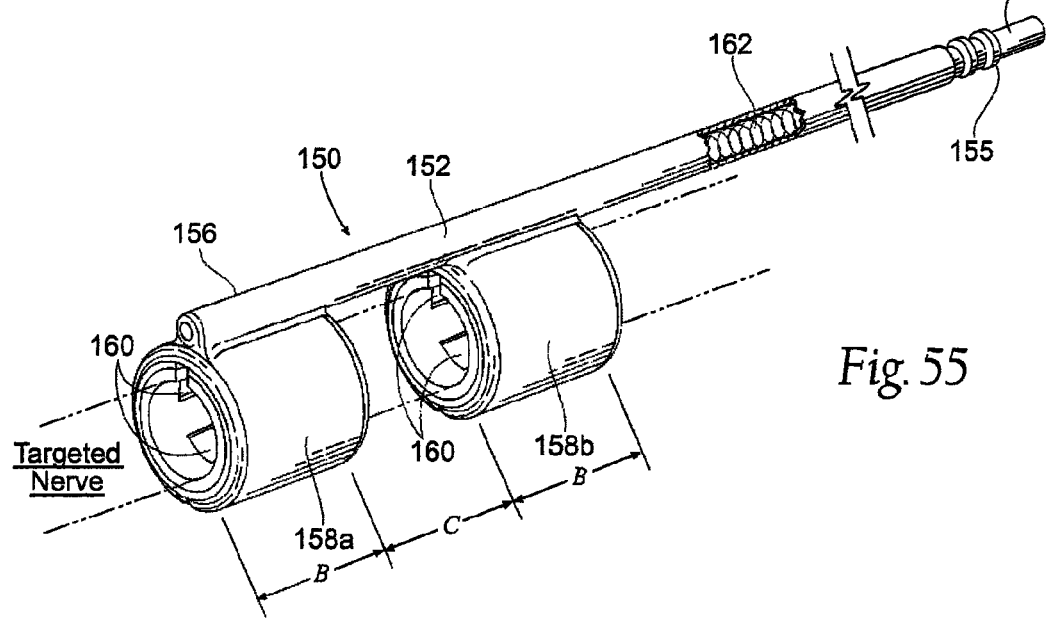
FIG. 55 is a perspective view of an alternative lead and electrode configuration, the lead and electrode being adapted to provide stimulation and/or blocking and/or recording of a target nerve.
Figure 56:
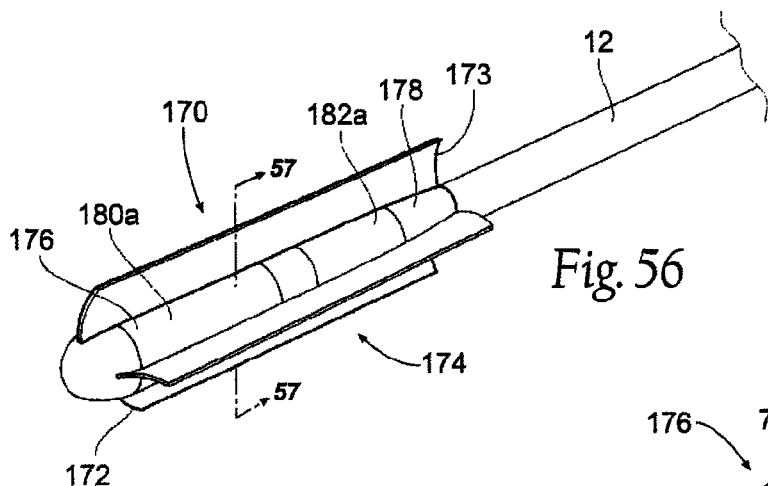
FIG. 56 is a perspective view of an electrode array configuration adapted to provide focused electrical stimulation to a targeted nerve.
Figure 57:
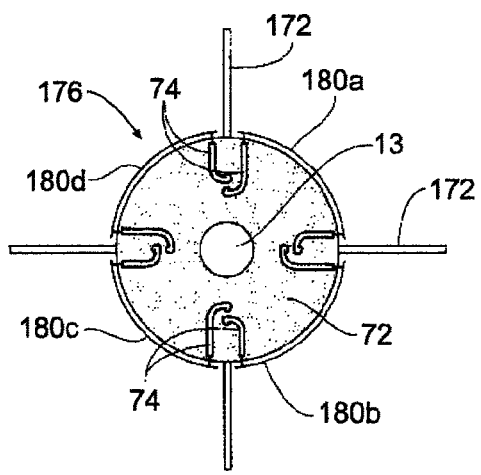
FIG. 57 is a section view of the electrode array taken generally along line 57-57 in FIG. 56.

In an alternative embodiment shown in FIG. 55, a cuff electrode configuration 150 is provided for recording, and/or stimulation, and/or blocking of a target nerve. The cuff electrode configuration 150 may be of the type described in co-pending U.S. patent application Ser. No. 11/653,578, filed Jan. 16, 2007, entitled "Devices, Systems, and Methods Employing a Molded Nerve Cuff Electrode," which is incorporated herein by reference. The cuff electrode 150 includes an implantable lead 152 having a proximal portion 154 and a distal portion 156. The proximal portion includes a connector 155 and the distal portion 156 carries two split cuff segments 158A and 158B. Within each cuff segment 158A, 158B, are positioned one or more electrodes 160. Wire elements 162 electrically couple each electrode 160 to the connector 155. Each cuff segment may include longitudinal lengths "B" ranging about 3 mm to about 5 mm, with a gap "C" ranging about 2 mm to about 4 mm, and in one application, "B" is about 4 mm and "C" is about 3 mm. It is to be appreciated that the cuff electrode configuration 150 may be a continuous cuff in place of the dual cuff configuration as shown.

F. Focused Stimulation Electrode

FIGS. 56 through 59 shows an embodiment of a lead/electrode array configuration 170 that is adapted to provide focused electrical stimulation to a targeted tissue region, i.e., a muscle or nerve, such as target nerve A and/or target nerve B, to help shield a non-targeted nerve or tissue from receiving stimulation intended for a target nerve or tissue located in proximity to the non-targeted nerve or tissue. The non-targeted tissue region in the field of urology generally consists of nerves innervating the urethra, anus, colon, rectum, urethral sphincter, anal sphincter, the dorsal genital nerves and/or its roots and/or branches, and the pelvic nerves and/or its roots and/or branches.

The focused electrode configuration 170 may be similar to the electrode 16 configuration as previously described, with the addition of one or more non-conductive fins 172 having a first end and a second end extending a portion of or the full length or more of the conductive portion(s) 174 of the lead 12.

The fins 172 may range from flexible to rigid depending on the targeted region for deployment, and the fins may include both flexible and rigid fins. In one embodiment the fins 172 assume a collapsed condition against the lead 12 body when within a sleeve 32. In this condition, the fins 172 are shielded from contact with tissue. Once the location is found, the sleeve 32 can be withdrawn, holding the lead 12 and conductive portion 174 stationary. Free of the sleeve 32, the fins 172 spring open to assume their radially deployed condition in tissue, fixing the conductive portion 174 in the desired location. Expansion means 173, such as a protruding tip on the proximal edge of the fin 172, may be included to assist the fins 172 to radially deploy with a slight tug or twist of the lead 12.

In the embodiment shown, the conductive portion is adapted for both monopolar and bipolar operation and includes a distal electrode array 176 spaced apart from a proximal electrode array 178. As can be seen in section view of FIG. 57, an exemplary embodiment of the distal electrode array 176 comprises a quad electrode configuration including electrodes 180A, 180B, 180C, and 180D, although more or less electrodes (and fins) may be provided. Each fin 172 separates an adjacent electrode element 180(A-D). A wire element 74 is coupled to each electrode element 180(A-D) and extends to the connector 62 on the proximal portion of the lead 12. As previously described, the lead comprises a molded or extruded component 72 and may include an inner lumen 13 for use with a guidewire.

Figure 58:
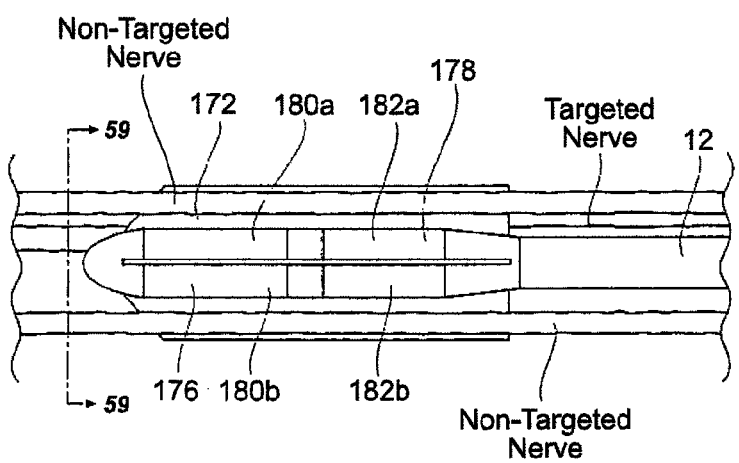
FIG. 58 is side view of the electrode array shown in FIG. 56, the electrode array shown positioned near a target nerve and non-target nerves.
Figure 59:
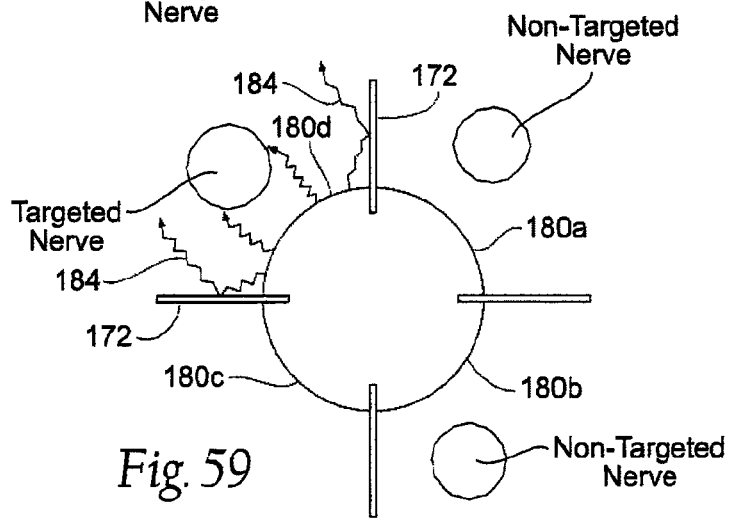
FIG. 59 is a front view of the electrode array taken generally along line 59-59 in FIG. 58, showing the electrical energy being focused (directed) toward the targeted nerve, and away from a non-targeted nerve.
Figure 63:
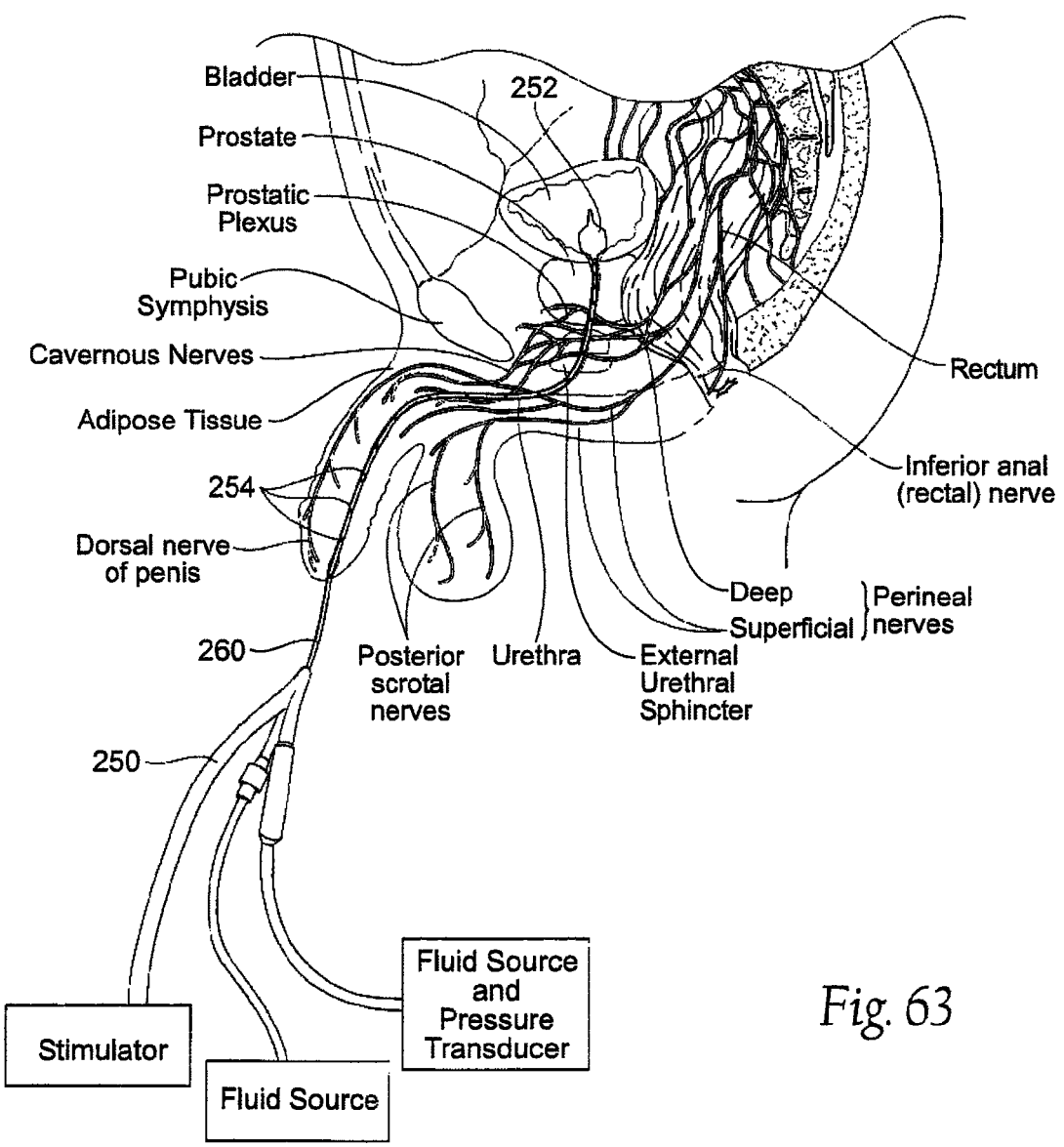
FIG. 63 is a lateral anatomical view showing the stimulating catheter of FIG. 60A positioned within the urethra of a human male to selectively stimulate target nerves near the urethra.

In use, the focused electrode configuration is positioned at the targeted region, as shown in FIGS. 58 and 59. Multiple non-target nerves may be located near the target nerve. The physician may first attempt to tune the electrode array 176 by activation of one or more electrodes 180A through 180D either alone or in combination with one or more electrodes 182(A-D). When the desired response is elicited, the lead implant procedure is continued, as previously described. As shown in FIG. 59, it is likely that the desired response would be accomplished with the activation of at least electrode 180D (and possibly electrode 182D if in bipolar mode) in order to stimulate the target nerve with energy 184, and without any unwanted stimulation of the non-target nerves.

IX. Stimulating Catheter

One or more stimulating catheters may be used as clinical screening tools to identify appropriate candidates for the sexual function restoration system (see FIGS. 60A through 63). If a subject's stimulating catheter test demonstrates that urethral stimulation is able to cause an erection, then a lead 12 or 12' as shown and described would be implanted near the urethra in close proximity to the target nerve (e.g., cavernous nerve) using one of the described approaches. Similarly, another lead 12 or 12' may be placed near the target nerve B (e.g., pudendal nerve). After implantation of one or more leads, the subject would be sent home for a predetermined test period (e.g., two weeks to two months) with the leads 12 or 12' connected to an external pulse generator (as previously described).

If the home trial provides functional results, e.g., restoration of sexual function, then the patient may proceed to receive a fully implanted system, including an implantable pulse generator (IPG) to evaluate restoration of sexual function over a longer period (e.g., 3 to 6 months, or more). In contrast to the more invasive sexual restoration procedures, and/or drug therapies, the present systems and methods will allow urologists to place the lead/electrode(s) near the target nerve(s) easily and reliably because the target nerves are an area in which urologists are comfortable and familiar.

In use, when the subject is ready for sexual activity, they may press a button on their external controller to activate the sexual restoration system 10. When the sexual activity has concluded, they may press the button again, or other button, on the external controller to turn the system off.

The idea of stimulating nerves near the urethra using a stimulating catheter is known, but the stimulating catheter 250 provides a unique combination of features. The stimulating catheter 250 is adapted to remain securely in place and stimulate the nerves near the urethra at the same time. If the catheter does not remain securely in place, it provides less accurate information about the location of stimulation because the stimulating lead can move relative to the urethra.

As can be seen in FIG. 60A, the novel stimulating catheter 250 has a balloon 252 that is inflated in the bladder neck that secures the catheter and one or more stimulating electrodes 254 in place so it does not move within the urethra. The stimulating catheter 250 as shown has multiple electrodes 254 along its length (e.g., 17 electrodes are shown) that can stimulate the nerves near the urethra. This means once the catheter 250 is in place, it does not have to be moved again until it is removed. This is a crucial feature because movement inside the urethra can activate unwanted nerves, which may produce unwanted outcomes (e.g., unwanted elicitation of reflexes such as a reflex bladder spasm or contraction).

Multiple stimulating electrodes 254 placed along the catheter body 260 allow the stimulating catheter 250 to be able to stimulate different portions of the urethra and surrounding nerves without having to move the catheter inside the urethra once the catheter 250 is in place. Each electrode 254 may be secured to the catheter body with an adhesive 255 (see FIG. 60B), which also serves to provide a smooth transition from the catheter body 260 to an edge of an electrode 254. The electrodes 254 near the proximal portion 262 of the catheter body 260 are generally spaced about 1 cm to about 5 cm apart, and more desirably about 1.5 cm to about 2 cm apart, and the electrodes 254 near the distal portion 264 are generally spaced about 0.1 mm to about 2 cm apart, and more desirably about 0.3 cm to about 0.7 cm apart.

The multiple electrodes 254 permit bipolar stimulation and ensure that one electrode will be located within a short distance (e.g. one cm or less) of the portion of the urethra nearest the target nerves and most sensitive to electrical stimulation.

The stimulating catheter 250 may also be used in both men and women. The higher concentration of electrodes 254 near the distal portion 264 of the catheter body 260 serves to most effectively stimulate the shorter urethra in women (generally about two to four cm long), and a large number of electrodes 254 along the length of the catheter body 260 are designed to accommodate urethras of longer lengths, and the higher concentration of electrodes 254 is placed to stimulate the most well innervated portions of the urethra in either a man or a woman.

Additionally, the stimulating catheter may have a coude (curved) tip 258 which enables it to be inserted in men with enlarged prostates (see FIG. 60A), Without the curved tip 258, it would be nearly impossible to place the stimulating catheter in most men with enlarged prostates. The stimulating catheter body 260 may be small in diameter (e.g., twelve Fr), meaning that after the balloon 252 is deflated in the bladder neck, the rest of the catheter body 260 will not obstruct the urethra and will allow for voiding (around the catheter body) to be monitored.

The catheter body 260 is desirably a dual lumen body having a proximal portion 262 and a distal portion 264. The first lumen 266 extends from a fitting 268 near the proximal end 262 to the balloon 252 near the distal end 264, and carries an insulated solid or stranded wire element 270 for each electrode 254 (see FIGS. 61 and 62). The first lumen 266 also serves as a path for fluid flow (i.e., saline, air, or distilled water) to fill and drain the balloon 252. The fitting 268 is adapted to be connected to a fluid pump. Alternatively, a third lumen may be provided to serve as the balloon fill lumen.

The wire elements 270 for each electrode 254 are carried in an extension 276 which extends from the first lumen 266 to a connector 278. The connector 278 then couples to a computer system or external pulse generator, for example, to provide selective stimulation to the multiple electrodes 254.

The second lumen 272 extends from a fitting 274 near the proximal end 262 to an opening 276 near the catheter body tip 258, and serves as a path for fluid flow to fill and/or drain the bladder, and to measure fluid pressure, although this feature may not be needed in a sexual restoration application, but may be used to investigate lower urinary tract functions and reflexes. The fitting 174 is adapted to be connected to a fluid pump and pressure transducer.

Figure 64:
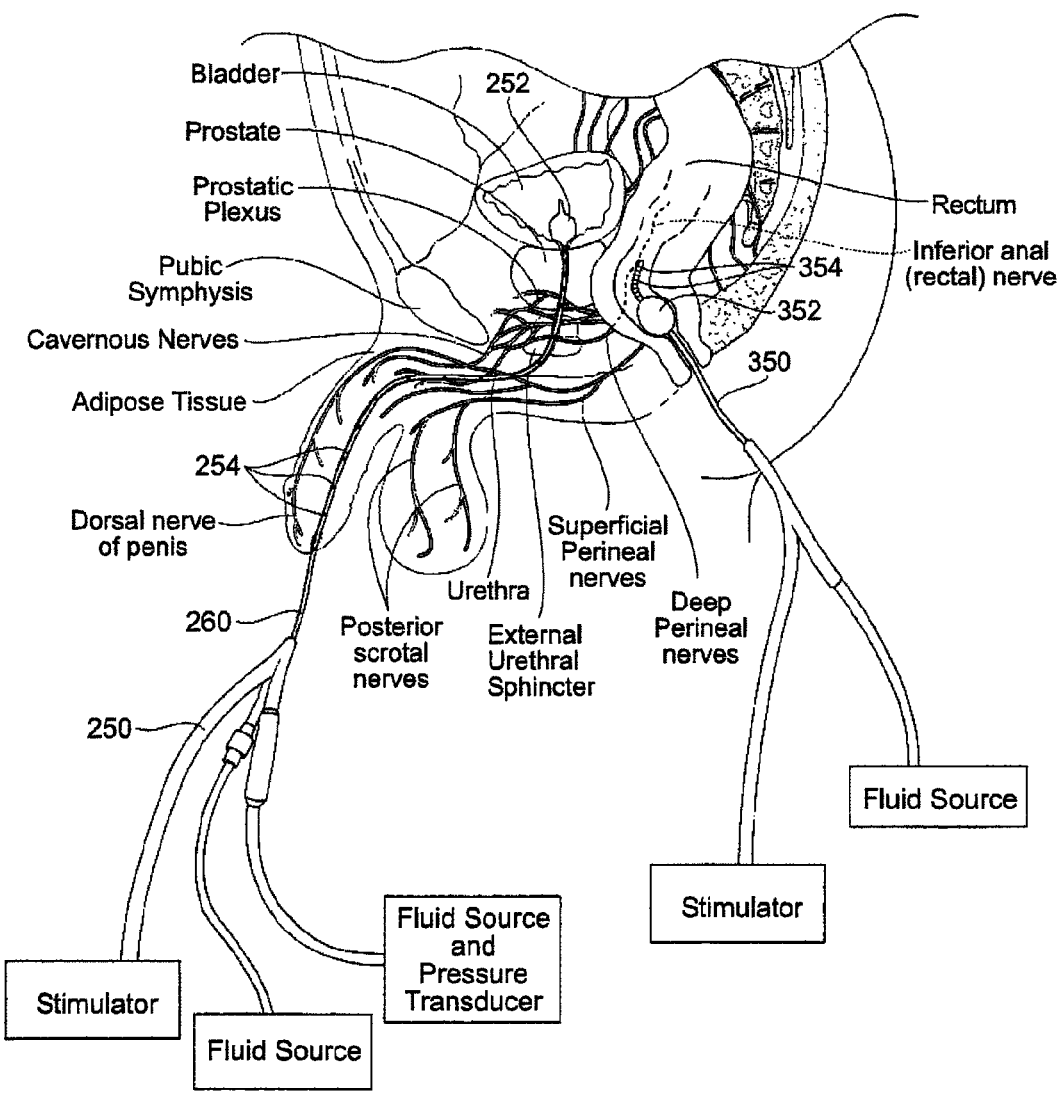
FIG. 64 is a lateral anatomical view similar to FIG. 63, showing an additional stimulating catheter positioned within the rectum of a human mate to selectively stimulate target nerves near the wall of the rectum.

A second stimulating catheter 350 may also be used, either alone, or in conjunction with the urethral stimulating catheter 250 (see FIG. 64). The stimulating catheter 350 would be positioned in the rectum for stimulation of a target nerve. As shown, the catheter 350 may include a balloon 352, and includes an array of electrodes 354. At least one electrode 354 would likely be positioned on the distal tip of the catheter to allow a desired placement of the electrode against the rectal wall. As shown, the catheter 350 would be coupled to a stimulator and a fluid source to expand the balloon.

The diameter of the catheter body 360 is likely larger than the catheter body 260 of the stimulating electrode 250. The catheter body 360 may be malleable, and may be pre-bent in a desired configuration so as to maintain its shape throughout the insertion and stimulation process.

X. Kits

The various tools and devices as just described can be consolidated for use in a functional kit or kits. The kits can take various forms. A single kit may include the necessary components for carrying out a single stage implant procedure as previously described. Alternatively, more than one kit may be constructed for carrying out the two stage implant procedure. Each kit also preferably includes directions for using the contents of the kit to carry out a desired procedure. The instructions for use can also be available through an internet web page.

XI. Representative Indications

Due to its technical features, the implant system 10 can be used to provide beneficial results in diverse therapeutic and functional restorations indications.

Restoration of sexual function pertains to both male and females. Male restoration may include both erection and/or ejaculation actions, for example. Female restoration may include both arousal (engorgement) and/or lubrication, for example.

The implant system 10 can be used for veterinary uses. The ability to control/activates sexual actions such as erection and/or ejaculation actions may be used in animal reproduction technologies, such as artificial insemination. Artificial insemination is commonly used for selective reproduction of bovines, swine, horses, dogs, and cats, as non-limiting examples In the field of urology, for example, possible indications for use of the implant system 10 include the treatment of (i) urinary and fecal incontinence; (ii) micturition/retention; (iii) pelvic floor muscle activity; and/or (iv) pelvic pain; (v) defecation/constipation; and (vi) restoration of sexual function.

The implant system 10 can be used for deep brain stimulation in the treatment of (i) Parkinson's disease; (ii) multiple sclerosis; (iii) essential tremor; (iv) depression; (v) eating disorders; (vi) epilepsy; and/or (vii) minimally conscious state.

The implant system 10 can be used for pain management by interfering with or blocking pain signals from reaching the brain, in the treatment of, e.g., (i) peripheral neuropathy; and/or (ii) cancer.

The implant system 10 can be used for vagal nerve stimulation for control of epilepsy, depression, or other mood/psychiatric disorders.

The implant system 10 can be used for the treatment of obstructive sleep apnea.

The implant system 10 can be used for gastric stimulation to prevent reflux or to reduce appetite or food consumption.

The implant system 10 can be used in functional restorations indications such as the restoration of motor control, to restore (i) impaired gait after stroke or spinal cord injury (SCI); (ii) impaired hand and arm function after stroke or SCI; (iii) respiratory disorders; (iv) swallowing disorders; (v) sleep apnea; and/or (vi) neurotherapeutics, allowing individuals with neurological deficits, such as stroke survivors or those with multiple sclerosis, to recover functionally.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

Various features of the invention are set forth in the following claims.

The invention claimed is:

1. A stimulating catheter system comprising a catheter, the catheter comprising:
   an elongated flexible body having a proximal end and a distal end and at least one lumen extending at least a portion of the body;
   an inflatable balloon disposed at or near the distal end;
   an electrode array disposed along the flexible body, wherein respective electrodes of the electrode array are regularly spaced along the flexible body; and
   an electrical lead coupled to each electrode in the electrode array and extending through the body, wherein the electrical lead is configured to be connected to an electrical source via an external connection,
   wherein the catheter is configured to deliver neuromodulation stimulation to a patient from the electrical source via the electrical lead and the electrode array,
   wherein the at least one lumen includes a first, and
   wherein the first lumen exits the flexible body at or near the distal end and serves as a path for fluid flow in and out of the flexible body at or near the distal end.

2. The catheter system according to claim 1, wherein the electrode array is disposed proximal to the inflatable balloon along the flexible body.

3. The catheter system according to claim 1,
wherein the flexible body is configured to be positioned within the urethra of a male and/or female animal or human.

4. The catheter system according to claim 1,
wherein the flexible body is configured to be positioned within the rectum of a male and/or female animal or human.

5. The catheter system according to claim 1,
wherein the flexible body is configured to be positioned within the vagina of a female animal or human.

6. The catheter system according to claim 1,
wherein at least one electrode is positioned on or near the distal tip of the flexible body.

7. The catheter system according to claim 1,
wherein the electrode array is coupled to the outside of the flexible body.

8. The catheter system according to claim 1,
wherein the flexible body is malleable.

9. The catheter system according to claim 1,
wherein the flexible body is adapted to be bendable while positioned within a body cavity, and is configured to be bendable during removal without causing damage to the body cavity or internal structures.

10. The catheter system according to claim 1,
wherein the flexible body is pre-bent in a desired configuration so as to maintain its shape during insertion and stimulation.

11. The catheter system according to claim 1,
wherein the electrode array comprises a proximal portion and a distal portion, the electrodes of the proximal portion are spaced apart a first distance, and the electrodes of the distal portion are spaced apart at a second distance less than the first distance.

12. The catheter system according to claim 1,
wherein the electrode array comprises a proximal portion and a distal portion, the electrodes of the proximal portion are spaced about 1 cm to about 5 cm apart, and the electrodes of the distal portion are spaced apart about 0.1 mm to about 2 cm apart.

13. The catheter system according to claim 1,
wherein the electrode array comprises a proximal portion and a distal portion, the electrodes of the proximal portion are spaced about 1.5 cm to 2 cm apart, and the electrodes of the distal portion are spaced apart about 0.3 cm to about 0.7 cm apart.

14. The catheter system according to claim 1,
wherein the flexible body includes a coude tip at the distal end.

15. The catheter system according to claim 1, wherein the at least one lumen comprises a second lumen extending at least a portion of the catheter body.

16. The catheter system according to claim 15,
wherein the second lumen carries the electrical lead to the electrode array.

17. The catheter system according to claim 15,
wherein the second lumen is in fluid flow communication with the balloon and serves as a path for fluid flow to fill and drain the balloon.

18. The catheter system according to claim 15,
wherein the at least one lumen includes a third lumen.

19. The catheter system according to claim 18,
wherein the third lumen is in fluid flow communication with the balloon and serves as a path for fluid flow to fill and drain the balloon.

20. The catheter system according to claim 1,
wherein the electrode array is configured to deliver the neuromodulation therapy in a monopolar, bipolar, and/or multi-polar configuration.

21. The catheter system according to claim 1,
wherein the neuromodulation stimulation therapy delivered via the electrode array is configured to cause efferent and/or afferent stimulation of at least one of a target nerve A and a target nerve B, to produce an erection.

22. The catheter system according to claim 21, wherein the target nerve A is selected from the group consisting of the cavernous nerve and/or spinal, sacral, lumbar, and/or thoracic roots and/or branches; the prostatic plexus and/or its spinal, sacral, lumbar, and/or thoracic roots and/or branches; the pelvic nerve and/or its spinal, sacral, lumbar, and/or thoracic roots and/or branches; the hypogastric nerve and/or its spinal, sacral, lumbar, and/or thoracic roots and/or branches; and the splanchnic nerve and/or its spinal, sacral, lumbar, and/or thoracic roots and/or branches, and
wherein the target nerve B is selected from the group consisting of the pudendal nerve and/or its spinal, sacral, lumbar, and/or thoracic roots and/or branches; the perineal nerve and/or its spinal, sacral, lumbar, and/or thoracic roots and/or branches; the nerves that innervate the ischiocavernosus, bulbocavernosus, and/or bulbospongiosus muscles and/or their spinal, sacral, lumbar, and/or thoracic roots and/or branches; and the nerves that innervate the transverse perineal muscles and/or their spinal, sacral, lumbar, and/or thoracic roots and/or branches.

23. The catheter system of claim 1, further comprising the electrical source configured to be connected to the electrical lead via the external connection, wherein the electrical source comprises a neuromodulation stimulation generator configured to generate the neuromodulation stimulation delivered to the patient.

24. The catheter system according to claim 23,
wherein the neuromodulation stimulation delivered via the electrode array is configured to cause afferent stimulation of at least one of a target nerve A and a target nerve B, the afferent stimulation activating central nervous system circuitry that coordinates and/or produces efferent activity in at least one of the target nerve A and the target nerve B, to produce an erection.

25. The catheter system according to claim 23,
wherein the neuromodulation stimulation delivered via the electrode array is configured to cause afferent stimulation of the dorsal genital nerves and/or its roots and/or its branches, the afferent stimulation activating central nervous system circuitry that coordinates and/or produces efferent activity in at least one of a target nerve A and a target nerve B, to produce an erection.

26. The catheter system of claim 1, wherein the at least one lumen includes a second lumen, wherein the second lumen carries the electrical lead to the electrode array, is in fluid flow communication with the balloon, and serves as a path for fluid flow to fill and drain the balloon.

* * * * *

UNITED STATES PATENT AND TRADEMARK OFFICE
CERTIFICATE OF CORRECTION

PATENT NO.        : 8,805,533 B2  
APPLICATION NO.   : 13/031482  
DATED             : August 12, 2014  
INVENTOR(S)       : Joseph W. Boggs, II et al.

Page 1 of 1

It is certified that error appears in the above-identified patent and that said Letters Patent is hereby corrected as shown below:

Claims

Claim 1, col. 38, line 61: "wherein the at least one lumen includes a first, and" should be changed to -- "wherein the at least one lumen includes a first lumen, and" --

Signed and Sealed this
Tenth Day of November, 2015

Michelle K. Lee
*Director of the United States Patent and Trademark Office*